United States Patent
Inoue et al.

(10) Patent No.: US 9,231,217 B2
(45) Date of Patent: Jan. 5, 2016

(54) SYNTHESIS METHOD OF ORGANOMETALLIC COMPLEX, SYNTHESIS METHOD OF PYRAZINE DERIVATIVE, 5,6-DIARYL-2-PYRAZYL TRIFLATE, LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Kanagawa-ken (JP)

(72) Inventors: Hideko Inoue, Kanagawa (JP); Tomohiro Kubota, Kanagawa (JP); Miki Kanamoto, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

(21) Appl. No.: 14/551,712

(22) Filed: Nov. 24, 2014

(65) Prior Publication Data

US 2015/0147840 A1    May 28, 2015

(30) Foreign Application Priority Data

Nov. 28, 2013  (JP) .................................. 2013-245957

(51) Int. Cl.

| | | |
|---|---|---|
| H01L 21/76 | (2006.01) | |
| H01L 51/00 | (2006.01) | |
| C07F 15/00 | (2006.01) | |
| C07D 241/12 | (2006.01) | |
| C09K 11/06 | (2006.01) | |
| H01L 51/50 | (2006.01) | |

(52) U.S. Cl.

CPC .......... *H01L 51/0085* (2013.01); *C07D 241/12* (2013.01); *C07F 15/0033* (2013.01); *C09K 11/06* (2013.01); *C09K 2211/185* (2013.01); *H01L 51/5016* (2013.01); *H01L 2251/308* (2013.01)

(58) Field of Classification Search

CPC ............ H01L 51/0085; H01L 51/5016; C07F 15/003

USPC ........................ 438/46; 544/225, 408; 257/40

See application file for complete search history.

(56) References Cited

U.S. PATENT DOCUMENTS

| | | | | |
|---|---|---|---|---|
| 4,303,689 | A  * | 12/1981 | Winter et al. ................. | 426/537 |
| 6,017,944 | A  * | 1/2000 | Chu et al. ...................... | 514/413 |
| 6,395,916 | B1 * | 5/2002 | Buchwald et al. ............ | 556/413 |
| 6,417,357 | B1 * | 7/2002 | Tinkl et al. .................... | 544/216 |
| 6,448,433 | B1 * | 9/2002 | Marcuccio et al. ................ | 562/7 |
| 6,821,646 | B2 * | 11/2004 | Tsuboyama et al. .......... | 428/690 |

(Continued)

FOREIGN PATENT DOCUMENTS

JP       2011-216903 A      10/2011

*Primary Examiner* — Caleb Henry
(74) *Attorney, Agent, or Firm* — Husch Blackwell LLP

(57) ABSTRACT

Provided is a 5,6-diaryl-2-pyrazyl triflate, its synthetic method, and a method for synthesizing an organometallic complex having a triarylpyrazine ligand from the 5,6-diaryl-2-pyrazyl triflate. The triflate is readily obtained from the corresponding 5,6-diarylpyrazin-2-ol, and the palladium-catalyzed coupling of the 5,6-diaryl-2-pyrazyl triflate with an arylboronic acid derivative leads to a high yield of a triarylpyrazine derivative having high purity. The use of the triarylpyrazine derivative in the reaction with a metal compound such as a metal chloride results in an ortho-metallated organometallic complex with high purity. The high purity of the organometallic complex contributes to the extremely high durability of a light-emitting element.

17 Claims, 14 Drawing Sheets

(56) References Cited

U.S. PATENT DOCUMENTS

| | | | |
|---|---|---|---|
| 7,993,494 B2 * | 8/2011 | Inoue et al. | 204/157.72 |
| 8,084,145 B2 | 12/2011 | Inoue et al. | |
| 8,101,755 B2 | 1/2012 | Inoue et al. | |
| 8,329,903 B2 | 12/2012 | Inoue et al. | |
| 8,426,420 B2 * | 4/2013 | Nazare et al. | 514/253.09 |
| 8,598,179 B2 * | 12/2013 | Nazare et al. | 514/254.02 |
| 8,664,383 B2 * | 3/2014 | Inoue et al. | 544/225 |
| 8,686,158 B2 * | 4/2014 | Furuya et al. | 548/101 |
| 8,889,858 B2 * | 11/2014 | Inoue et al. | 544/225 |
| 8,921,549 B2 * | 12/2014 | Inoue et al. | 544/250 |
| 9,059,414 B2 * | 6/2015 | Inoue et al. | |
| 2001/0019782 A1 | 9/2001 | Igarashi et al. | |
| 2002/0121638 A1 | 9/2002 | Grushin et al. | |
| 2003/0032838 A1 * | 2/2003 | Marcuccio et al. | 562/7 |
| 2003/0059646 A1 | 3/2003 | Kamatani et al. | |
| 2003/0236413 A1 * | 12/2003 | Cellier et al. | 546/290 |
| 2004/0171833 A1 * | 9/2004 | Buchwald et al. | 546/22 |
| 2005/0221123 A1 * | 10/2005 | Inoue et al. | 428/690 |
| 2005/0253135 A1 * | 11/2005 | Stossel et al. | 257/40 |
| 2006/0127696 A1 * | 6/2006 | Stossel et al. | 428/690 |
| 2007/0128658 A1 * | 6/2007 | Blackwell et al. | 435/7.1 |
| 2007/0129545 A1 * | 6/2007 | Inoue et al. | 544/225 |
| 2007/0244320 A1 * | 10/2007 | Inoue et al. | 544/225 |
| 2008/0286604 A1 | 11/2008 | Inoue et al. | |
| 2009/0015143 A1 | 1/2009 | Inoue et al. | |
| 2009/0183982 A1 * | 7/2009 | Inoue et al. | 204/157.72 |
| 2010/0331295 A1 * | 12/2010 | Busch et al. | 514/210.18 |
| 2011/0288292 A1 * | 11/2011 | Parham et al. | 544/35 |
| 2012/0097938 A1 * | 4/2012 | Meyer et al. | 257/40 |
| 2012/0313087 A1 * | 12/2012 | Buchholz et al. | 257/40 |
| 2013/0137866 A1 | 5/2013 | Inoue et al. | |
| 2013/0165653 A1 | 6/2013 | Inoue et al. | |
| 2013/0200359 A1 * | 8/2013 | Stoessel et al. | 257/40 |
| 2013/0277617 A1 * | 10/2013 | Pan et al. | 252/500 |
| 2013/0292665 A1 * | 11/2013 | Ono | 257/40 |
| 2013/0299743 A1 * | 11/2013 | Pan et al. | 252/301.35 |
| 2014/0014930 A1 * | 1/2014 | Hirose et al. | 257/40 |
| 2014/0034938 A1 * | 2/2014 | Ishibashi et al. | 257/40 |
| 2014/0117289 A1 * | 5/2014 | Pan et al. | 252/500 |
| 2014/0246656 A1 * | 9/2014 | Inoue et al. | 257/40 |
| 2015/0191825 A1 * | 7/2015 | Hildreth | 164/57.1 |

* cited by examiner

FIG. 4A
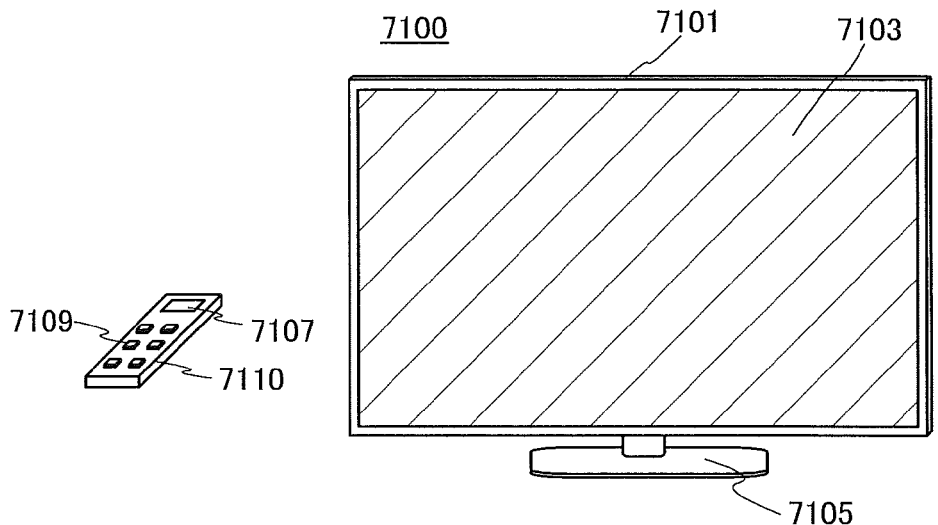
FIG. 4B                FIG. 4C
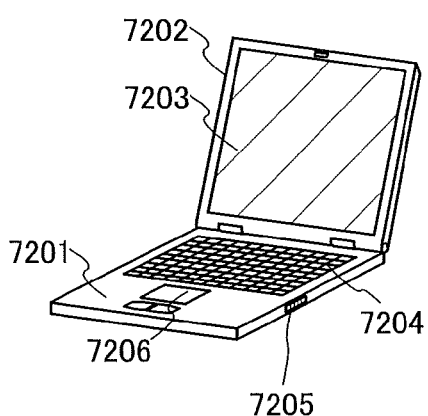   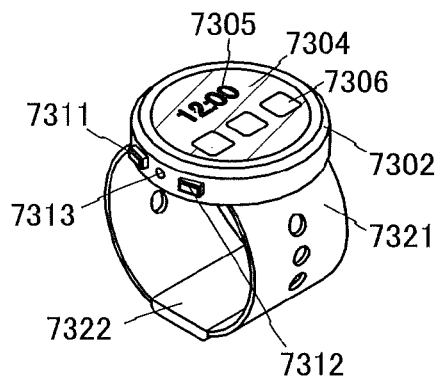
FIG. 4D
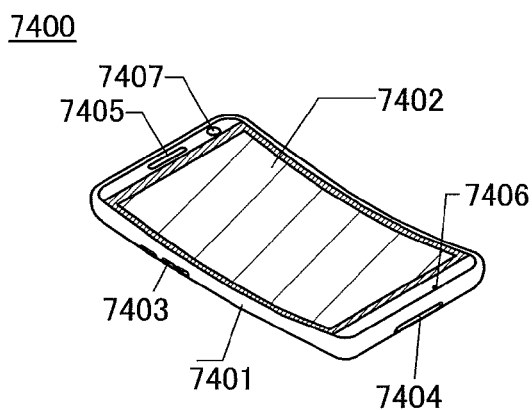

SYNTHESIS METHOD OF ORGANOMETALLIC COMPLEX, SYNTHESIS METHOD OF PYRAZINE DERIVATIVE, 5,6-DIARYL-2-PYRAZYL TRIFLATE, LIGHT-EMITTING ELEMENT, LIGHT-EMITTING DEVICE, ELECTRONIC DEVICE, AND LIGHTING DEVICE

BACKGROUND OF THE INVENTION

1. Field of the Invention

One embodiment of the present invention relates to a novel method for synthesizing an organometallic complex such as an organoiridium complex. Another embodiment of the present invention relates to a novel method for synthesizing a triarylpyrazine derivative. Another embodiment of the present invention relates to 5,6-diaryl-2-pyrazyl triflate used for the above synthesis methods. Another embodiment of the present invention relates to a light-emitting element, a light-emitting device, an electronic device, and a lighting device each including an organometallic complex synthesized by the above synthesis method.

Note that one embodiment of the present invention is not limited to the above technical field. Specifically, examples of the technical field of one embodiment of the present invention disclosed in this specification include a semiconductor device, a display device, a liquid crystal display device, a light-emitting device, a lighting device, and a method for manufacturing any of them.

2. Description of the Related Art

A light-emitting element in which an EL layer is provided between a pair of electrodes is a self-luminous light-emitting element in which carriers (holes and electrons) are injected from the pair of electrodes by application of an electric field and recombined in the EL layer to generate energy, so that light is emitted.

An organic compound is mainly used as an EL material for an EL layer in a light-emitting element and greatly contributes to an improvement in the characteristics of the light-emitting element. For this reason, novel organic compounds improved from various angles have been developed. When the organic compound contains impurities such as a halogen element, the characteristics of the light-emitting element deteriorate. To solve this problem, element characteristics are improved by reducing impurities by purification by sublimation (e.g., Patent Document 1).

REFERENCE

Patent Document

[Patent Document 1] Japanese Published Patent Application No. 2011-216903

SUMMARY OF THE INVENTION

However, purification by sublimation cannot necessarily remove impurities easily in synthesis of organic compounds. When a material used in a synthesis process contains a substance which potentially acts as an impurity, it is sometimes technically difficult to make an end product impurity-free. Thus, to reduce impurities in an organic compound, it is important to establish a synthesis method that does not result in a substance that can be an impurity in a synthesis process.

In view of the above backdrop, one embodiment of the present invention provides a novel 5,6-diaryl-2-pyrazyl triflate as an organic compound that realizes a synthesis method which negligibly gives impurities. Another embodiment of the present invention provides a method for synthesizing an organometallic complex such as an organoiridium complex in which the above 5,6-diaryl-2-pyrazyl triflate is used. Another embodiment of the present invention provides a method for synthesizing a triarylpyrazine derivative in which the above 5,6-diaryl-2-pyrazyl triflate is used. Another embodiment of the present invention provides a light-emitting element, a light-emitting device, an electronic device, or a lighting device using an organometallic complex obtained by the above synthesis method as an EL material. Another embodiment of the present invention provides a novel light-emitting element, a novel light-emitting device, a novel lighting device, or the like. Note that the descriptions of these objects do not disturb the existence of other objects. In one embodiment of the present invention, there is no need to achieve all the objects. Other objects will be apparent from and can be derived from the description of the specification, the drawings, the claims, and the like.

One embodiment of the present invention is a novel synthesis method by which the content of halogen such as chlorine that potentially acts as an impurity is reduced and an organometallic complex can be obtained efficiently. Specifically, in this method, a triarylpyrazine derivative is formed with the use of novel 5,6-diaryl-2-pyrazyl triflate, and then an organometallic complex with reduced halogen content is synthesized.

That is, one embodiment of the present invention is a synthesis method of an organometallic complex which includes the following steps: a step of coupling a 5,6-diaryl-2-pyrazyl triflate and an arylboronic acid to form a 2,3,5-triarylpyrazine derivative that is a triarylpyrazine derivative; a step of reacting the 2,3,5-triarylpyrazine derivative with a metal compound containing halogen to form a dinuclear complex; and a step of reacting the dinuclear complex with a ligand.

Another embodiment of the present invention is a synthesis method of an organometallic complex which includes the following steps: a step of coupling a 5,6-diaryl-2-pyrazyl triflate having a structure represented by General Formula (G0) and an arylboronic acid to form a 2,3,5-triarylpyrazine derivative that is a triarylpyrazine derivative; a step of reacting the 2,3,5-triarylpyrazine derivative with a metal compound containing halogen to form a dinuclear complex; and a step of reacting the dinuclear complex with a ligand. Note that, in the aforementioned embodiments, the organometallic complex is exemplified by an ortho-metallated complex, and iridium, platinum, rhodium, and the like are given as the metal.

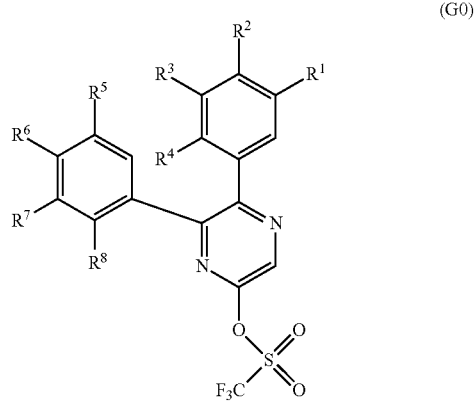

(G0)

In General Formula (G0), $R^1$ to $R^8$ each independently represent any one of hydrogen, an alkyl group having 1 to 6 carbon atoms, a phenyl group, and a phenyl group having, as a substituent, an alkyl group having 1 to 6 carbon atoms.

Note that the above synthesis method enables high-yield synthesis of the organometallic complexes using an inexpensive material and reduces the content of chlorine that potentially acts as an impurity; thus, the synthesis method is suitable for mass synthesis, for example.

Another embodiment of the present invention is a 5,6-diaryl-2-pyrazyl triflate with a structure represented by General Formula (G0) which can be used in the above synthesis method.

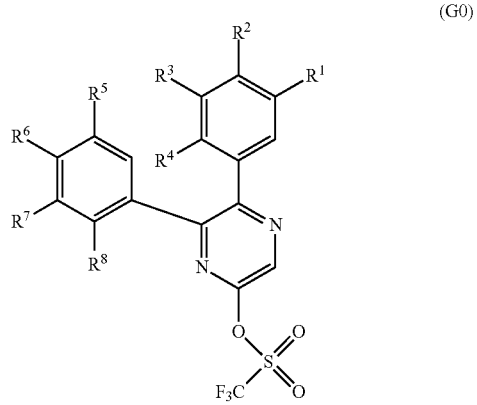

(G0)

In General Formula (G0), $R^1$ to $R^8$ each independently represent any one of hydrogen, an alkyl group having 1 to 6 carbon atoms, a phenyl group, and a phenyl group having, as a substituent, an alkyl group having 1 to 6 carbon atoms.

Other embodiments of the present invention are a light-emitting element using an organometallic complex synthesized by the above synthesis method, and a light-emitting device including the light-emitting element.

Note that one embodiment of the present invention includes not only a light-emitting device including the light-emitting element but also an electronic device and a lighting device each including the light-emitting device. The light-emitting device in this specification refers to an image display device and a light source (e.g., a lighting device). In addition, the light-emitting device includes, in its category, all of a module in which a light-emitting device is connected to a connector such as a flexible printed circuit (FPC), a tape carrier package (TCP), a module in which a printed wiring board is provided on the tip of a TCP, and a module in which an integrated circuit (IC) is directly mounted on a light-emitting element by a chip on glass (COG) method.

One embodiment of the present invention makes it possible to provide a novel method for synthesizing an organometallic complex in which a 5,6-diaryl-2-pyrazyl triflate that is a novel organic compound is used. Another embodiment of the present invention enables the production of a 5,6-diaryl-2-pyrazyl triflate that is a novel organic compound. Note that this novel organic compound does not contain a substance that can be an impurity during the synthesis by the above synthesis method, thereby reducing impurities in the organometallic complex that is an end product. Another embodiment of the present invention allows the formation of a highly reliable light-emitting element, a highly reliable light-emitting device, a highly reliable electronic device, or a highly reliable lighting device using an organometallic complex synthesized by the above synthesis method as an EL material. Another embodiment of the present invention is capable of providing a novel light-emitting element, a novel light-emitting device, a novel lighting device, or the like. Note that the description of these effects does not disturb the existence of other effects. In one embodiment of the present invention, there is no need to obtain all the effects. Other effects will be apparent from and can be derived from the description of the specification, the drawings, the claims, and the like.

BRIEF DESCRIPTION OF THE DRAWINGS

FIGS. 4A to 4D illustrate electronic devices.

DETAILED DESCRIPTION OF THE INVENTION

Figure 1:
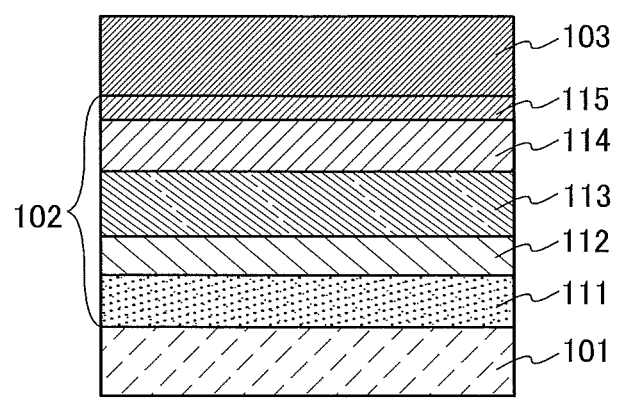
FIG. 1 illustrates a structure of a light-emitting element.

Hereinafter, embodiments of the present invention will be described with reference to the accompanying drawings. Note that the present invention is not limited to the following description, and various changes and modifications can be made without departing from the spirit and scope of the present invention. Therefore, the present invention should not be construed as being limited to the description in the following embodiments.

Embodiment 1

In this embodiment, a method for synthesizing an organometallic complex that is one embodiment of the present invention is described. Hereinafter, the explanation is mainly given to a synthetic method of an organoiridium complex. However, the embodiment is not limited to the synthetic method of an organoiridium complex but includes those of an organoplatinum complex, an organorhodium complex, and the like.

One embodiment of the present invention is a synthesis method that includes a synthetic pathway to a novel 5,6-diaryl-2-pyrazyl triflate, which is a synthetic intermediate, thereby producing an organometallic complex with reduced chlorine content in a high yield.

<<Synthesis Method of 5,6-Diaryl-2-Pyrazyl Triflate Represented by General Formula (G0)>>

First, a synthesis method of 5,6-diaryl-2-pyrazyl triflate represented by General Formula (G0) is described.

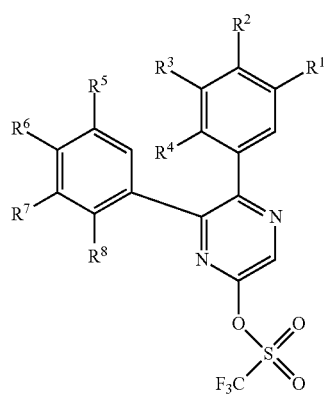

(G0)

The novel 5,6-diaryl-2-pyrazyl triflate (General Formula (G0)) is synthesized in the following manner. As shown in Synthesis Scheme (A-1) below, a 1,2-diaryl diketone (General Formula (a1)) and glycinamide hydrochloride are reacted to obtain a compound represented by General Formula (a2); then, a hydroxyl group of the compound represented by General Formula (a2) is transformed to a triflate group using trifluoromethanesulfonic anhydride (abbreviation: Tf$_2$O) in the presence of a weak base.

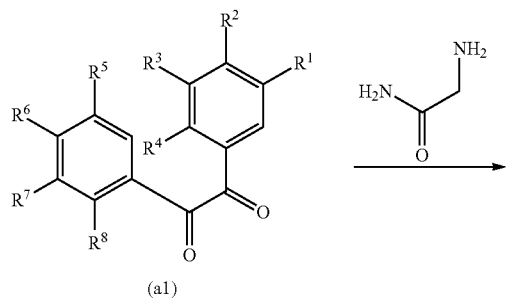

(A-1)

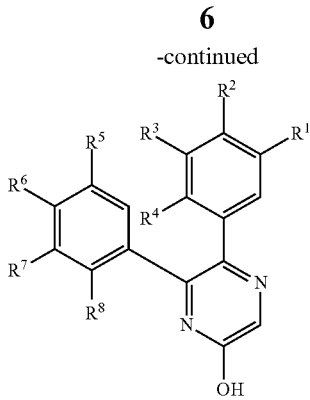

(a2)

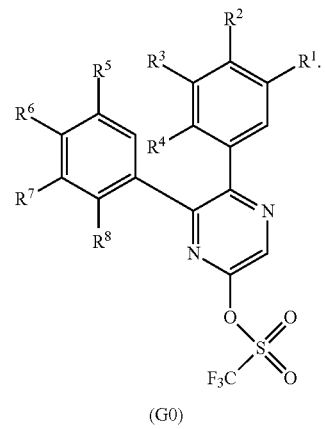

(G0)

In Synthesis Scheme (A-1), $R^1$ to $R^8$ each independently represent any one of hydrogen, an alkyl group having 1 to 6 carbon atoms, a phenyl group, and a phenyl group having, as a substituent, an alkyl group having 1 to 6 carbon atoms.

Note that the above 5,6-diaryl-2-pyrazyl triflate is a novel compound of one embodiment of the present invention that is useful in synthesizing organometallic complexes. Since a wide variety of the compounds (General Formula (a1) and General Formula (a2)) used in Synthesis Scheme (A-1) are commercially available or can be readily synthesized, many kinds of the 5,6-diaryl-2-pyrazyl triflate (General Formula (G0)) can be synthesized by the above synthesis method. Shown below are specific structural formulae of the 5,6-diaryl-2-pyrazyl triflate represented by General Formula (G0) (Structural Formulae (100) to (111)). Note that one embodiment of the present invention is not limited thereto.

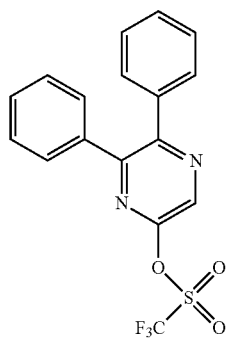

(100)

(101) 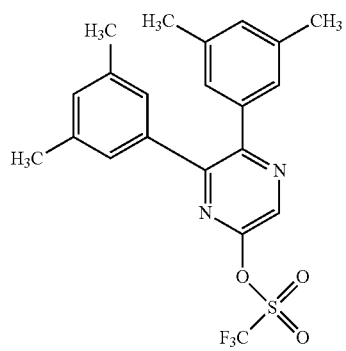
(102) 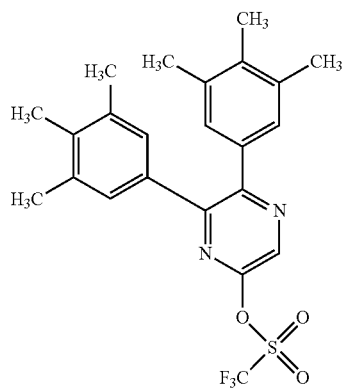
(103) 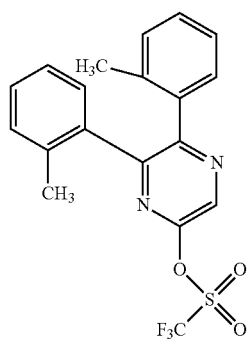
(104) 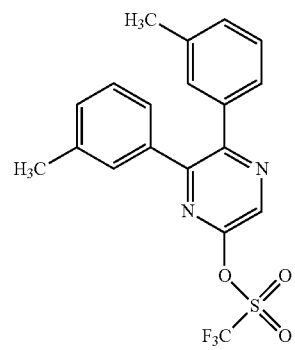
(105) 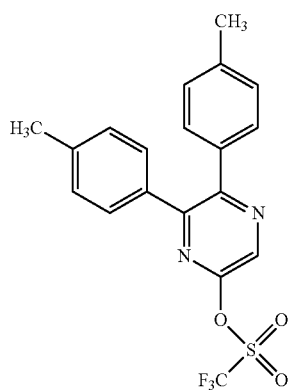
(106) 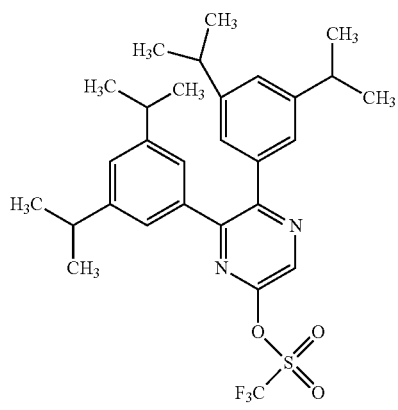
(107) 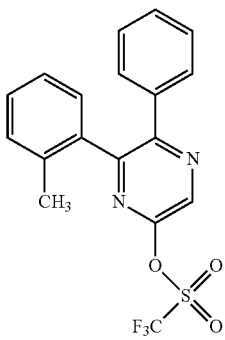
(108) 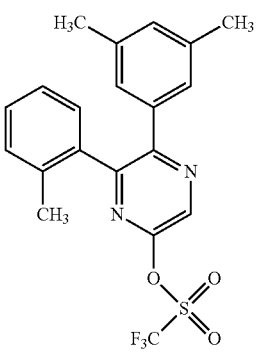

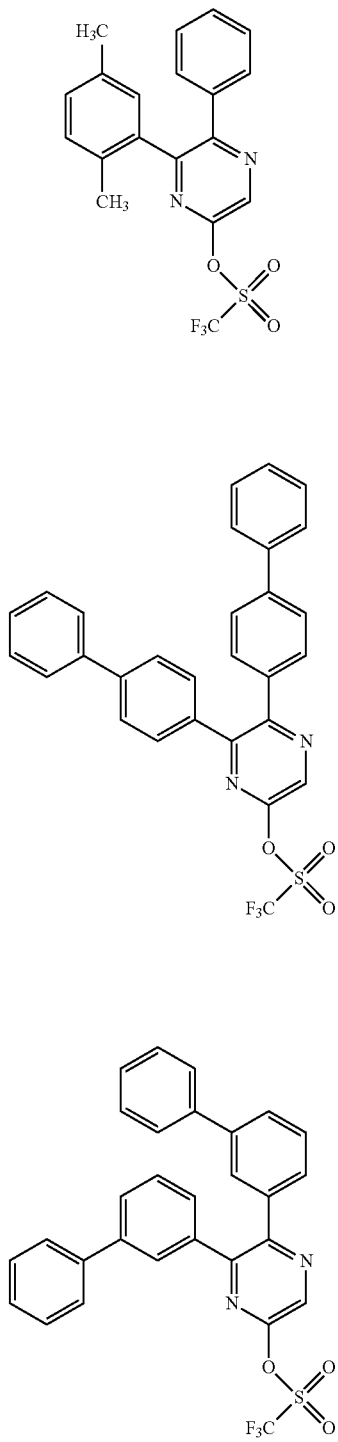

(109)

(110)

(111)

<<Synthesis Method of Triarylpyrazine Derivative Represented by General Formula (G1)>>

Then, as illustrated in Synthesis Scheme (A-2), the 5,6-diaryl-2-pyrazyl triflate (General Formula (G0)) and an arylboronic acid (General Formula (a3)) are coupled with each other, whereby a triarylpyrazine derivative having an aryl group as a substituent (General Formula (G1)) is synthesized.

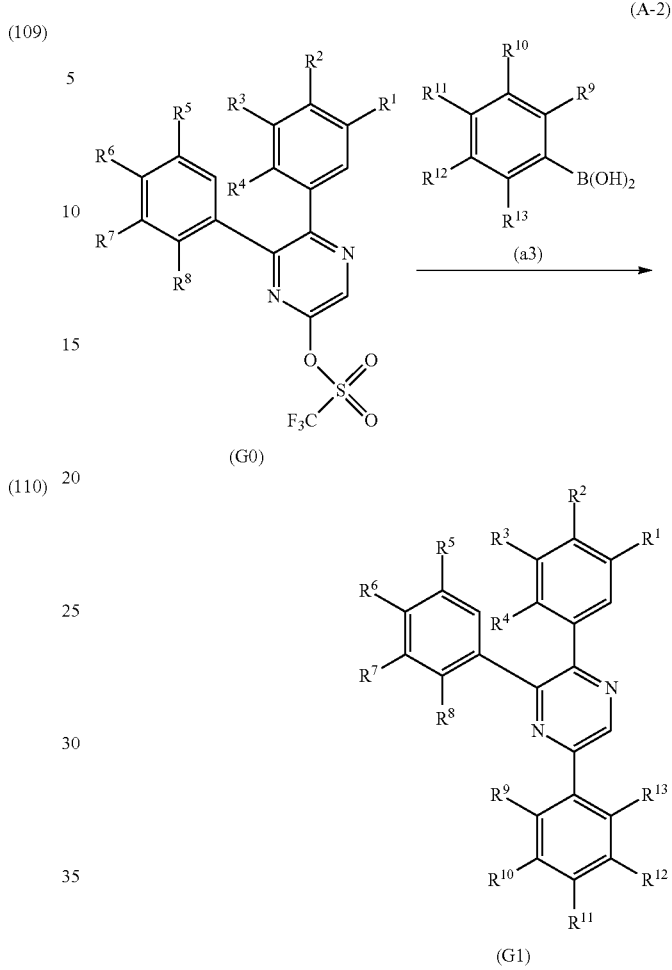

(A-2)

(G0)

(G1)

In Synthesis Scheme (A-2), $R^1$ to $R^{13}$ each independently represent any one of hydrogen, an alkyl group having 1 to 6 carbon atoms, a phenyl group, and a phenyl group having, as a substituent, an alkyl group having 1 to 6 carbon atoms.

Shown below are specific structural formulae of the triarylpyrazine derivative represented by General Formula (G1) and synthesized under Synthesis Scheme (A-2) (Structural Formulae (200) to (213)). Note that one embodiment of the present invention is not limited thereto.

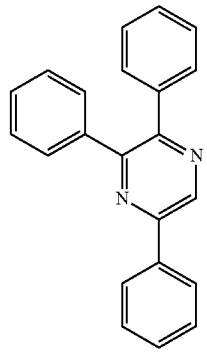

(200)

(201)
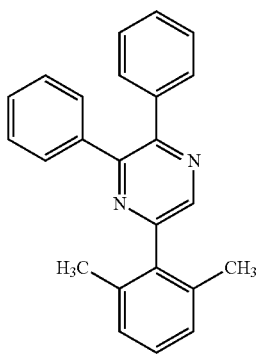
(202)
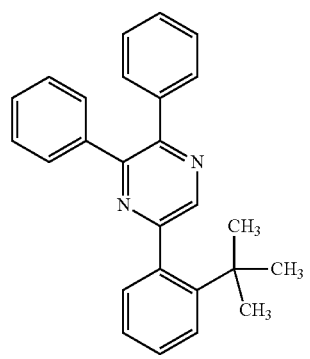
(203)
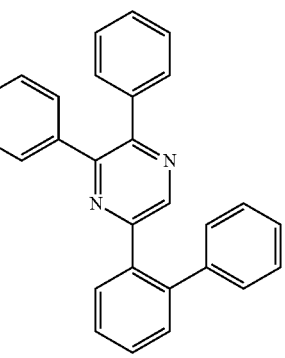
(204)
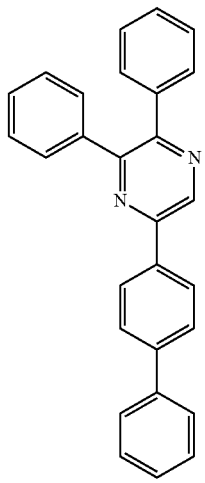
(205)
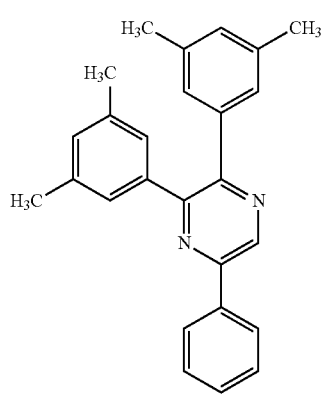
(206)
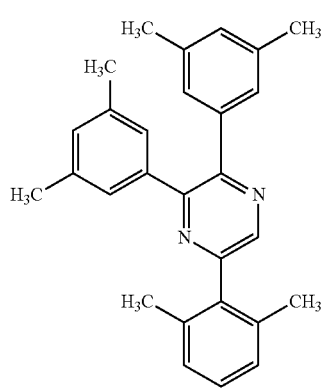
(207)
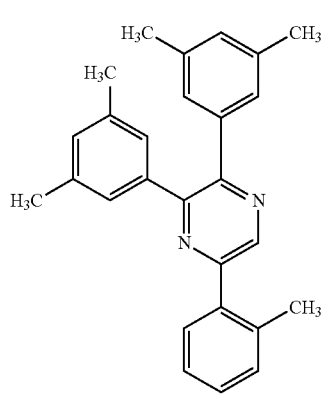
(208)

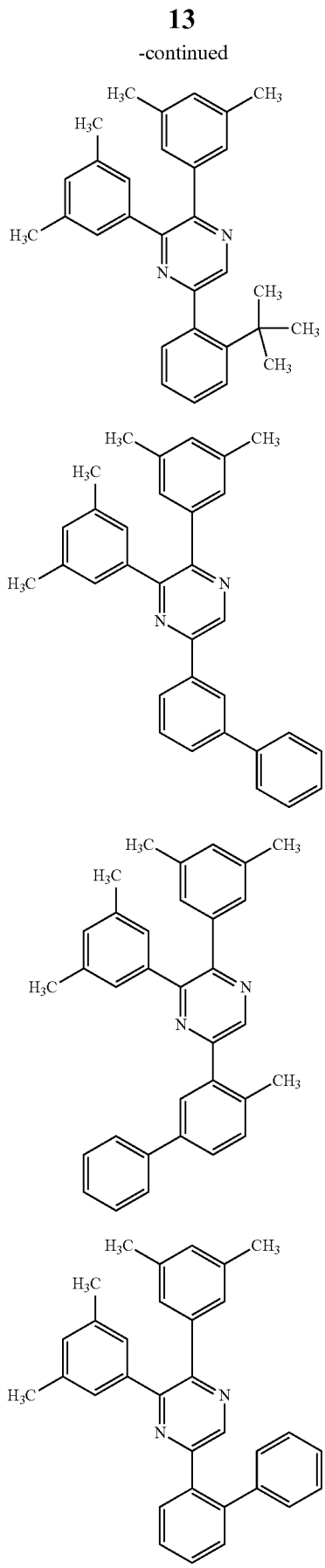

(209)

(210)

(211)

(212)

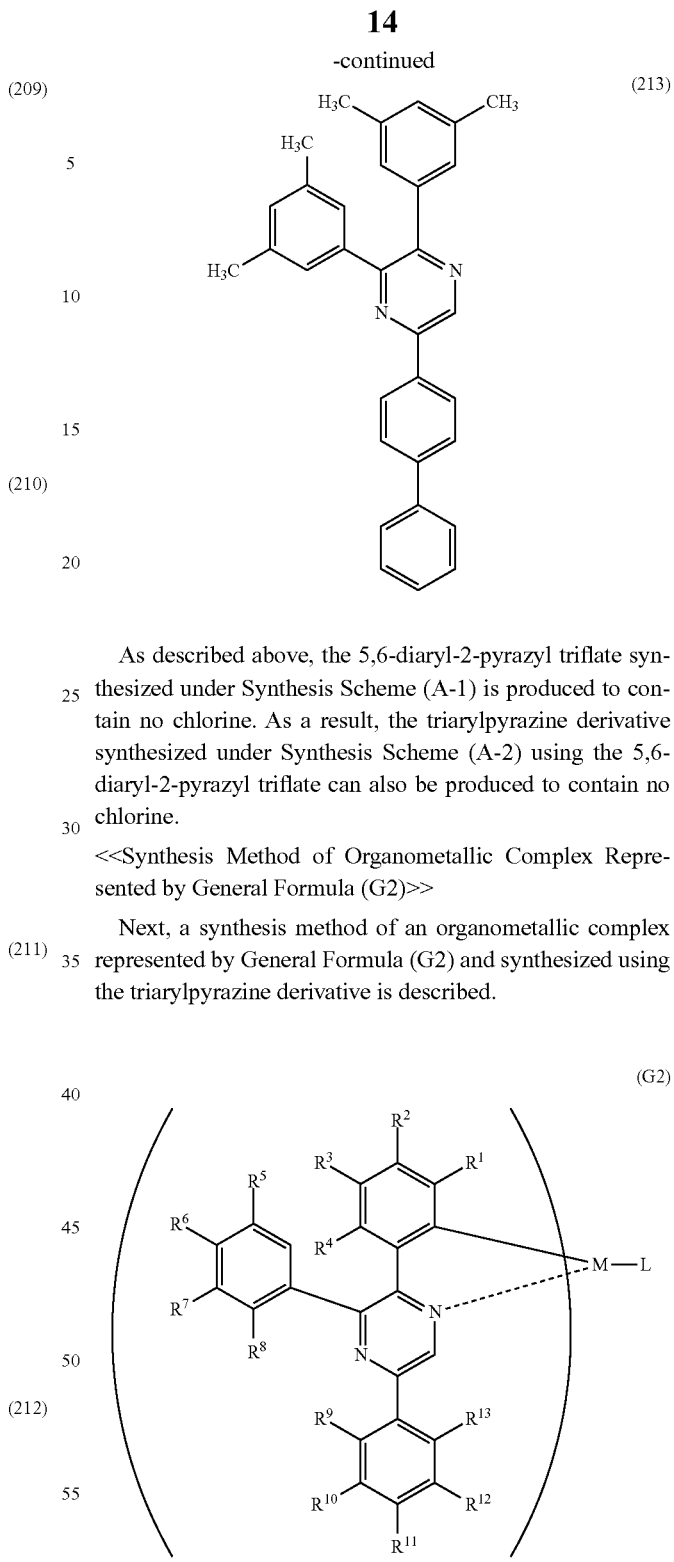

(213)

As described above, the 5,6-diaryl-2-pyrazyl triflate synthesized under Synthesis Scheme (A-1) is produced to contain no chlorine. As a result, the triarylpyrazine derivative synthesized under Synthesis Scheme (A-2) using the 5,6-diaryl-2-pyrazyl triflate can also be produced to contain no chlorine.

<<Synthesis Method of Organometallic Complex Represented by General Formula (G2)>>

Next, a synthesis method of an organometallic complex represented by General Formula (G2) and synthesized using the triarylpyrazine derivative is described.

In General Formula (G2), $R^1$ to $R^{13}$ each independently represent any one of hydrogen, an alkyl group having 1 to 6 carbon atoms, a phenyl group, and a phenyl group having, as a substituent, an alkyl group having 1 to 6 carbon atoms. Further, L represents a monoanionic ligand, and M represents iridium, platinum, or rhodium. Hereinafter, explanation is given to the case where M is iridium.

First, as shown in Synthesis Scheme (A-3-1), the pyrazine derivative represented by General Formula (G1) and an iridium compound which contains halogen (e.g., iridium chloride, iridium bromide, or iridium iodide) are reacted under an inert gas atmosphere in the absence of a solvent or in an alcoholic solvent (e.g., glycerol, ethylene glycol, 2-methoxyethanol, or 2-ethoxyethanol) alone, or a mixed solvent of water and an alcoholic solvent, whereby a dinuclear complex (P), which is one type of an organoiridium complex including a halogen-bridged structure, is obtained.

having, as a substituent, an alkyl group having 1 to 6 carbon atoms. In addition, Y represents halogen.

There is no particular limitation on the temperature of the reaction of Synthesis Scheme (A-3-1), and the reaction can be conducted under heating. When heating is conducted, an oil bath, a sand bath, or an aluminum block may be used. Alternatively, microwaves can be used as a heating source.

Then, as shown in Synthesis Scheme (A-3-2), the dinuclear complex (P) obtained under Synthesis Scheme (A-3-1) is reacted with a ligand HL in an inert gas atmosphere, whereby a proton of the ligand HL is dissociated and a monoanionic

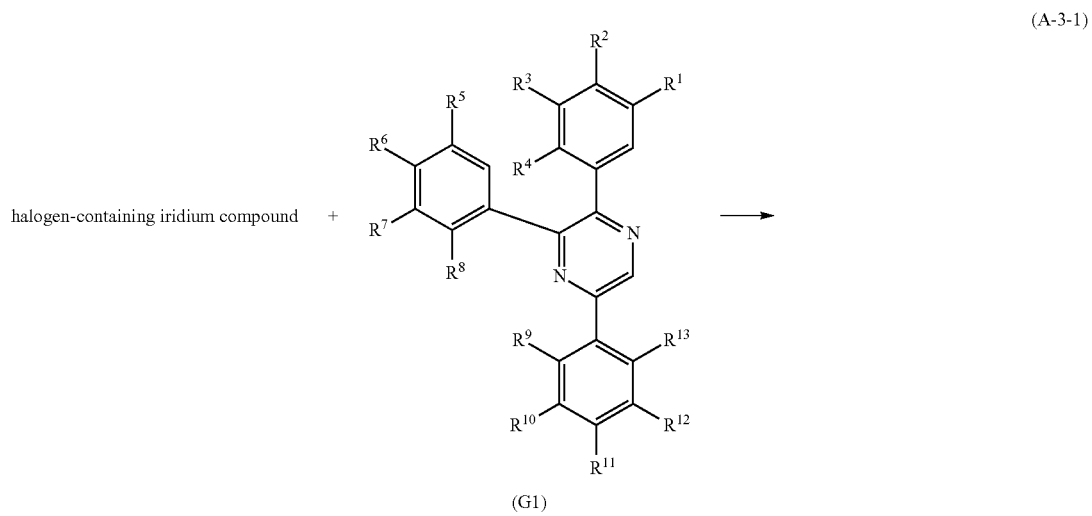

(A-3-1)

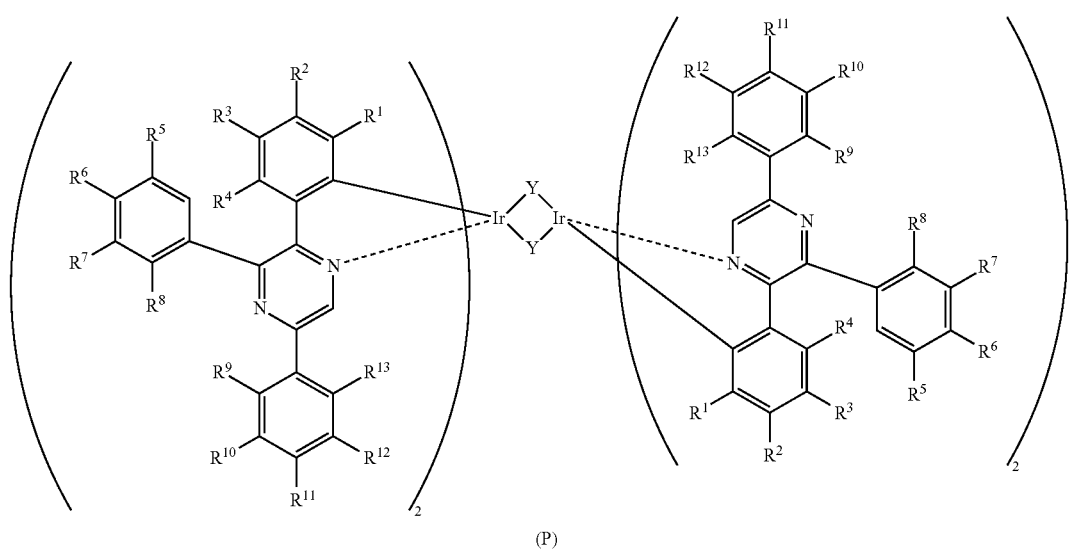

(P)

In Synthesis Scheme (A-3-1), $R^1$ to $R^{13}$ each independently represent any one of hydrogen, an alkyl group having 1 to 6 carbon atoms, a phenyl group, and a phenyl group ligand L coordinates to the iridium. Thus, the organoiridium complex represented by General Formula (G3) can be obtained.

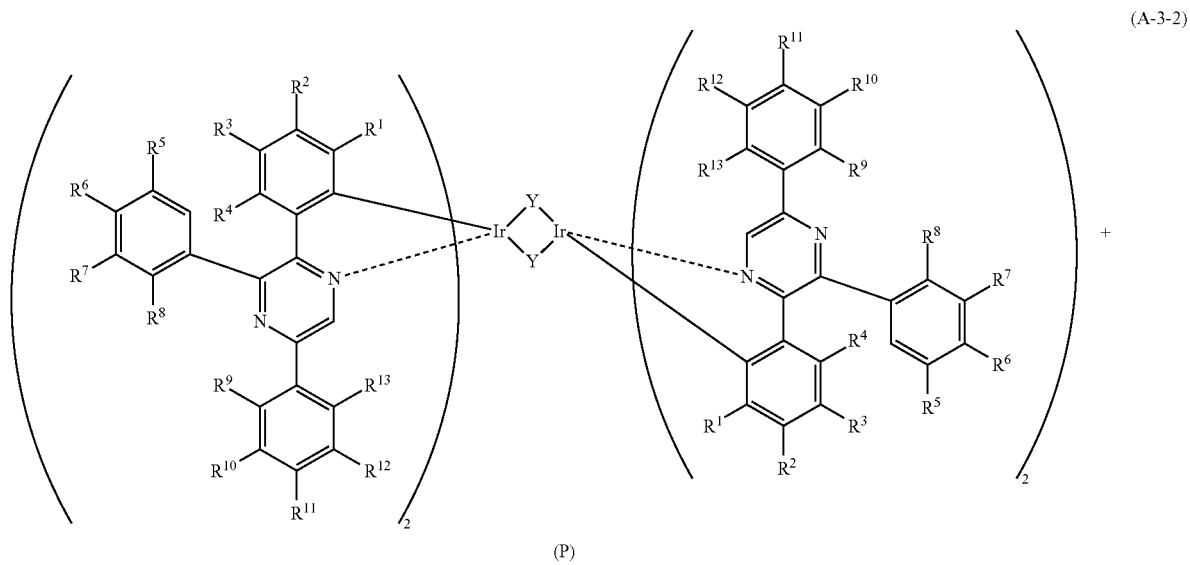

(A-3-2)

(P)

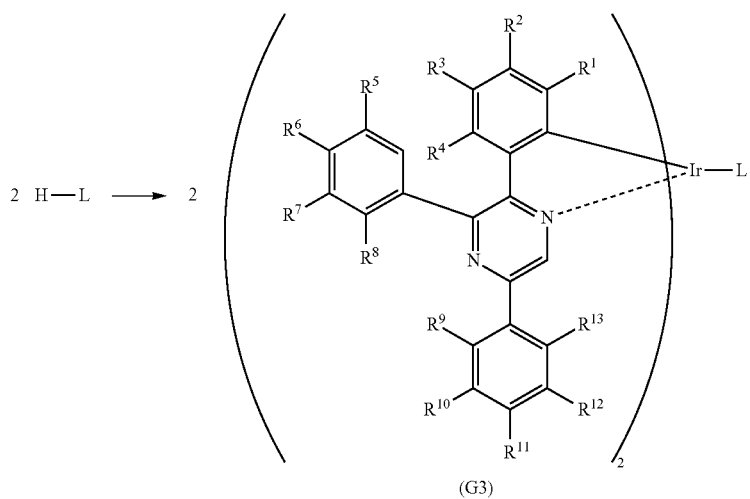

(G3)

In Synthesis Scheme (A-3-2), $R^1$ to $R^{13}$ each independently represent any one of hydrogen, an alkyl group having 1 to 6 carbon atoms, a phenyl group, and a phenyl group having, as a substituent, an alkyl group having 1 to 6 carbon atoms. Further, L represents a monoanionic ligand.

There is no particular limitation on the temperature of the reaction of Synthesis Scheme (A-3-2), and the reaction can be conducted under heating. When heating is conducted, an oil bath, a sand bath, or an aluminum block may be used. Alternatively, microwaves can be used as a heating source.

Shown below are specific structural formulae of the organoiridium complex represented by General Formula (G2) and synthesized under Synthesis Scheme (A-3-2) (Structural Formulae (300) to (315)). Note that one embodiment of the present invention is not limited thereto.

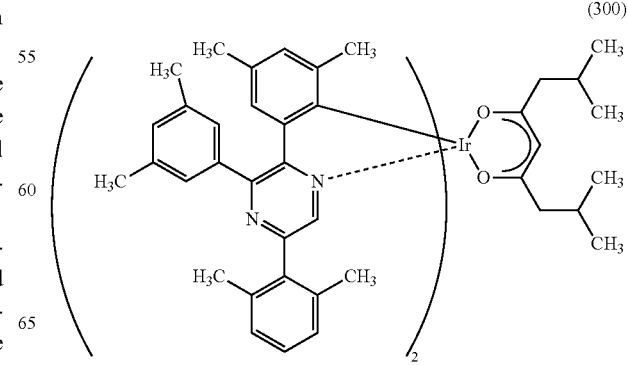

(300)

-continued
(301)
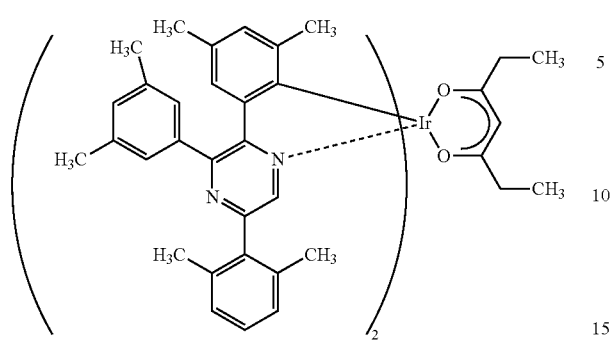
(302)
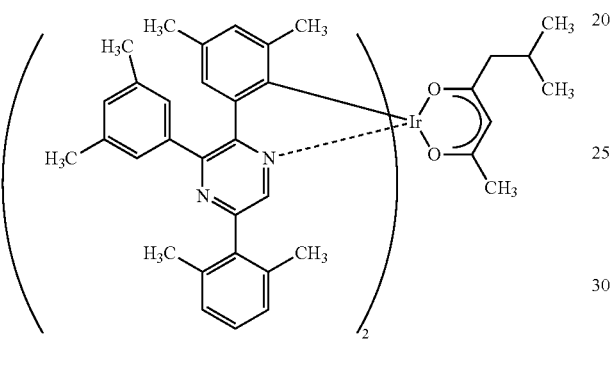
(303)
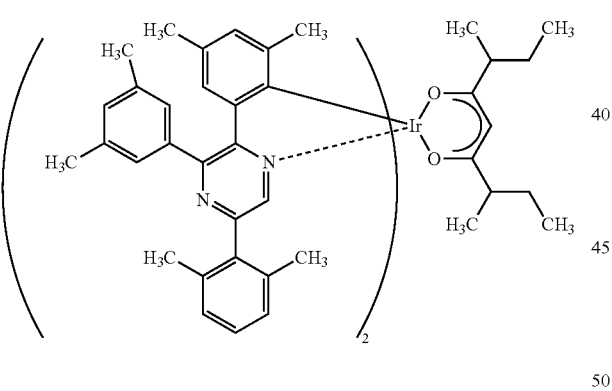
(304)
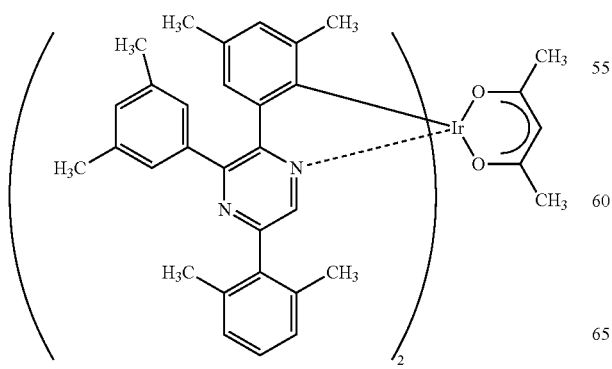
-continued
(305)
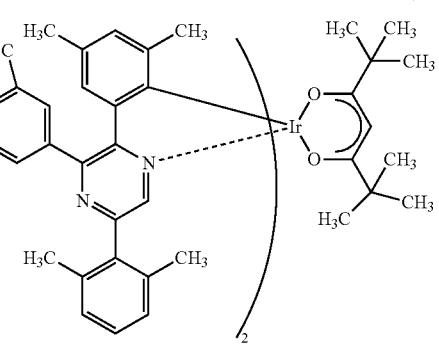
(306)
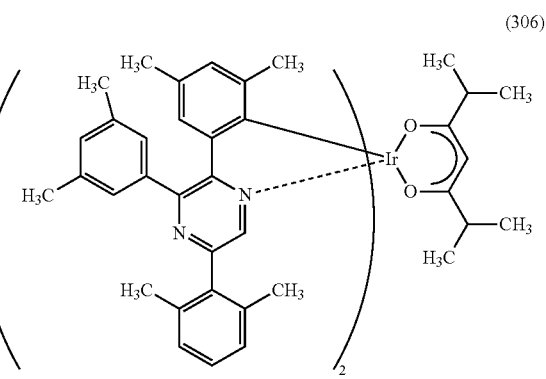
(307)
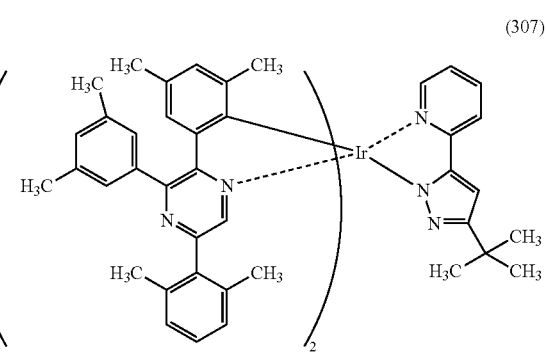
(308)
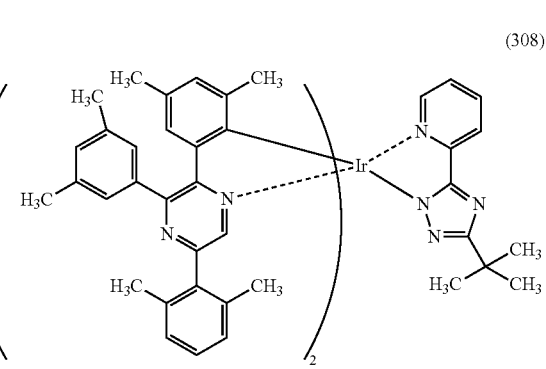

(309)
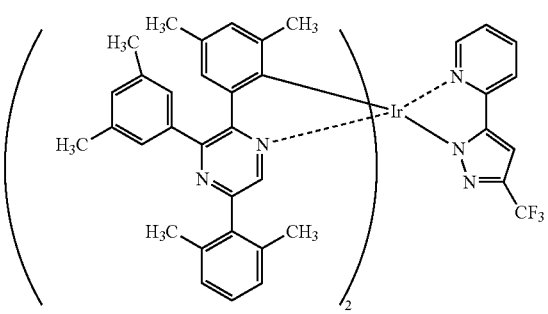

(310)
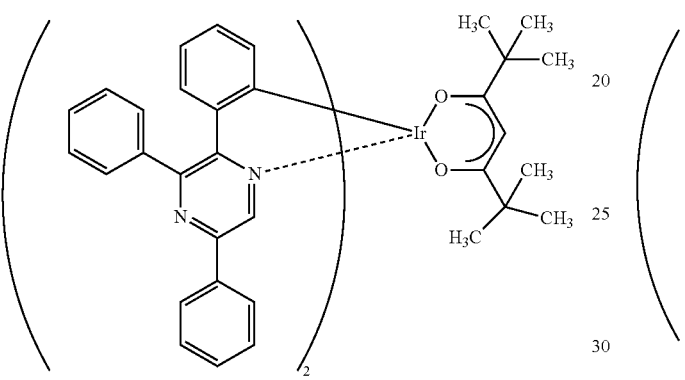

(311)
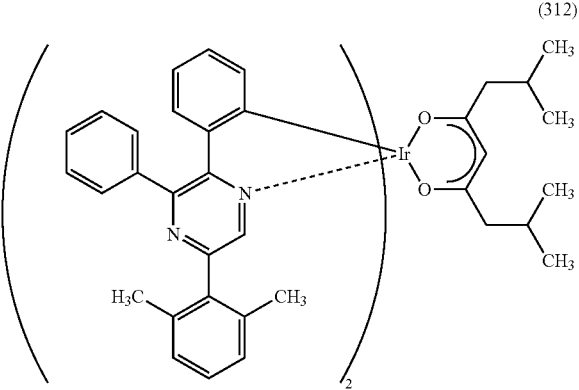

(312)
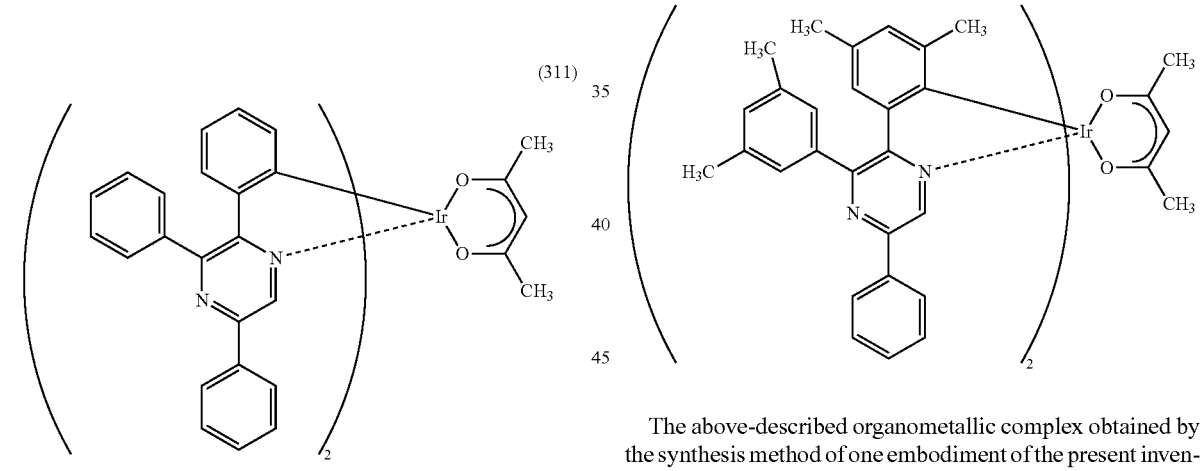

(313)
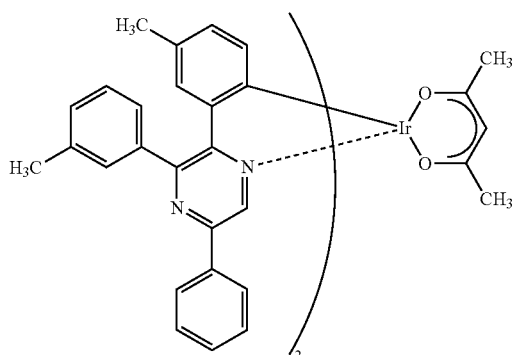

(314)
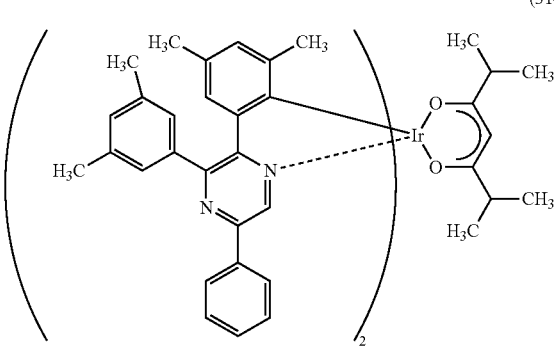

(315)
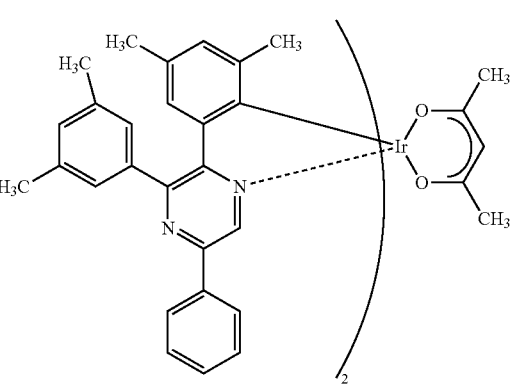

The above-described organometallic complex obtained by the synthesis method of one embodiment of the present invention can emit phosphorescence and thus can be used as a light-emitting material or a light-emitting substance of a light-emitting element.

An organometallic complex with reduced impurities can be synthesized by the synthesis method of one embodiment of the present invention. Thus, by using the organometallic complex as an EL material, a light-emitting element, a light-emitting device, an electronic device, or a lighting device having high emission efficiency and high reliability can be provided. Furthermore, an organometallic complex can be synthesized in a high yield by the synthesis method of one embodiment of the present invention, which enables stable supply of the material and a reduction in cost of a light-emitting element, a light-emitting device, an electronic device, a lighting device, or the like that includes the material.

Note that the structure described in this embodiment can be combined as appropriate with any of the structures described in the other embodiments.

Embodiment 2

In this embodiment, a light-emitting element in which the organometallic complex obtained by the synthesis method of one embodiment of the present invention is used as an EL material is described with reference to FIG. 1.

In a light-emitting element described in this embodiment, as illustrated in FIG. 1, an EL layer 102 including a light-emitting layer 113 is interposed between a pair of electrodes (a first electrode (anode) 101 and a second electrode (cathode) 103), and the EL layer 102 includes a hole-injection layer 111, a hole-transport layer 112, an electron-transport layer 114, an electron-injection layer 115, and the like in addition to the light-emitting layer 113.

When voltage is applied to such a light-emitting element, holes injected from the first electrode 101 side and electrons injected from the second electrode 103 side recombine in the light-emitting layer 113 to lead a light-emitting substance contained in the light-emitting layer 113 to an excited state. The light-emitting substance in the excited state emits light when it returns to the ground state.

Although the organometallic complex synthesized by the synthesis method of one embodiment of the present invention can be used for any one or more layers in the EL layer 102 described in this embodiment, the organometallic complex is preferably used for the light-emitting layer 113. In other words, the organometallic complex is used in part of a light-emitting element having a structure described below.

A specific example for fabricating the light-emitting element described in this embodiment is described below.

As the first electrode 101 and the second electrode 103, a metal, an alloy, an electrically conductive compound, a mixture thereof, and the like can be used. Specific examples are indium oxide-tin oxide (indium tin oxide (ITO)), indium oxide-tin oxide containing silicon or silicon oxide, indium oxide-zinc oxide (indium zinc oxide), indium oxide containing tungsten oxide and zinc oxide, gold (Au), platinum (Pt), nickel (Ni), tungsten (W), chromium (Cr), molybdenum (Mo), iron (Fe), cobalt (Co), copper (Cu), palladium (Pd), and titanium (Ii). In addition, an element belonging to Group 1 or Group 2 of the periodic table, for example, an alkali metal such as lithium (Li) or cesium (Cs), an alkaline earth metal such as calcium (Ca) or strontium (Sr), magnesium (Mg), an alloy containing such an element (MgAg, AlLi), a rare earth metal such as europium (Eu) or ytterbium (Yb), an alloy containing such an element, graphene, and the like can be used. The first electrode 101 and the second electrode 103 can be formed by, for example, a sputtering method or an evaporation method (including a vacuum evaporation method).

The hole-injection layer 111 injects holes into the light-emitting layer 113 through the hole-transport layer 112 with a high hole-transport property. The hole-injection layer 111 contains a substance with a high hole-transport property and an acceptor substance, so that electrons are extracted from the substance with a high hole-transport property by the acceptor substance to generate holes and the holes are injected into the light-emitting layer 113 through the hole-transport layer 112. The hole-transport layer 112 is formed using a substance with a high hole-transport property.

Specific examples of the substance with a high hole-transport property, which is used for the hole-injection layer 111 and the hole-transport layer 112, include aromatic amine compounds such as 4,4'-bis[N-(1-naphthyl)-N-phenylamino] biphenyl (abbreviation: NPB or α-NPD), N,N'-bis(3-methylphenyl)-N,N'-diphenyl-[1,1'-biphenyl]-4,4'-diamine (abbreviation: TPD), 4,4',4"-tris(carbazol-9-yl)triphenylamine (abbreviation: TCTA), 4,4',4"-tris(N,N-diphenylamino) triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB); 3-[N-(9-phenylcarbazol-3-yl)-N-phenylamino]-9-phenylcarbazole (abbreviation: PCzPCA1); 3,6-bis[N-(9-phenylcarbazol-3-yl)-N-phenylamino]-9-phenylcarbazole (abbreviation: PCzPCA2); and 3-[N-(1-naphthyl)-N-(9-phenylcarbazol-3-yl) amino]-9-phenylcarbazole (abbreviation: PCzPCN1). Other examples include carbazole derivatives such as 4,4'-di(N-carbazolyl)biphenyl (abbreviation: CBP), 1,3,5-tris[4-(N-carbazolyl)phenyl]benzene (abbreviation: TCPB), and 9-[4-(10-phenyl-9-anthracenyl)phenyl]-9H-carbazole (abbreviation: CzPA). The substances listed here are mainly ones that have a hole mobility of $10^{-6}$ cm$^2$/Vs or higher. Note that any substance other than the substances listed here may be used as long as the hole-transport property is higher than the electron-transport property.

A high molecular compound such as poly(N-vinylcarbazole) (abbreviation: PVK), poly(4-vinyltriphenylamine) (abbreviation: PVTPA), poly[N-(4-{N'-[4-(4-diphenylamino) phenyl]phenyl-N'-phenylamino}phenyl)methacrylamide] (abbreviation: PTPDMA), or poly[N,N'-bis(4-butylphenyl)-N,N'-bis(phenyl)benzidine](abbreviation: Poly-TPD) can also be used.

Examples of the acceptor substance that is used for the hole-injection layer 111 include oxides of metals belonging to Groups 4 to 8 of the periodic table. Specifically, molybdenum oxide is particularly preferable.

The light-emitting layer 113 is a layer containing a light-emitting substance. The light-emitting layer 113 may contain only a light-emitting substance; alternatively, a light-emitting substance (guest material) may be dispersed in a host material in the light-emitting layer 113. Note that a substance that has high triplet excitation energy is preferably used as the host material. As a light-emitting substance, the organometallic complexes shown in Embodiment 1 can be used.

The material that can be used as the light-emitting substance in the light-emitting layer 113 is exemplified by, in addition to the aforementioned organometallic complex, a light-emitting substance converting singlet excitation energy into luminescence or a light-emitting substance converting triplet excitation energy into luminescence. In this case, the light-emitting substance may be located in the same layer as or in a different layer from the organometallic complex. Examples of the light-emitting substance are given below.

As an example of the light-emitting substance converting singlet excitation energy into luminescence, a substance emitting fluorescence can be given.

Examples of the substance emitting fluorescence include N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(10-phenyl-9-anthryl)-4'-(9-phenyl-9H-carbazol-3-yl)triphenylamine (abbreviation: PCBAPA), N,N'''-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl) phenyl]-N,N',N'-triphenyl-1,4-phenylenediamine (abbreviation: 2DPAPPA), N,N,N',N',N",N",N"',N"'-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), {2-isopropyl-6-[2-(1,1,7,7-tetramethyl-2,3,6,7-tetrahydro-1H,5H-benzo[i]quinolizin-9-yl)ethenyl]-4H-pyran-4-ylidene}propanedinitrile (abbreviation: DCJTI), {2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), and 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM).

Examples of the light-emitting substance converting triplet excitation energy into luminescence include a substance emitting phosphorescence and a thermally activated delayed fluorescence (TADF) material. Note that "delayed fluorescence" exhibited by the TADF material refers to light emission having the same spectrum as normal fluorescence but an extremely long lifetime. The lifetime is $10^{-6}$ seconds or longer, preferably $10^{-3}$ seconds or longer.

Examples of the substance emitting phosphorescence include bis{2-[3',5'-bis(trifluoromethyl)phenyl]pyridinato-N,C$^{2'}$}iridium(III) picolinate (abbreviation: Ir(CF$_3$ppy)$_2$(pic)), bis[2-(4',6'-difluorophenyl)pyridinato-N,C$^{2'}$]iridium (III) acetylacetonate (abbreviation: FIracac), tris(2-phenylpyridinato)iridium(III) (abbreviation: Ir(ppy)$_3$), bis(2-phenylpyridinato)iridium(III) acetylacetonate (abbreviation: Ir(ppy)$_2$(acac)), tris(acetylacetonato)(monophenanthroline)terbium(II) (abbreviation: Tb(acac)$_3$(Phen)), bis(benzo[h]quinolinato)iridium(III) acetylacetonate (abbreviation: Ir(bzq)$_2$(acac)), bis(2,4-diphenyl-1,3-oxazolato-N,C$^{2'}$)iridium(III) acetylacetonate (abbreviation: Ir(dpo)$_2$(acac)), bis{2-[4'-(perfluorophenyl)phenyl]pyridinato-N,C$^{2'}$}iridium (II) acetylacetonate (abbreviation: Ir(p-PF-ph)$_2$(acac)), bis (2-phenylbenzothiazolato-N,C$^{2'}$)iridium(III) acetylacetonate (abbreviation: Ir(bt)$_2$(acac)), bis[2-(2'-benzo[4,5-a]thienyl)pyridinato-N,C$^{3'}$]iridium(III) acetylacetonate (abbreviation: Ir(btp)$_2$(acac)), bis(1-phenylisoquinolinato-N,C$^{2'}$)iridium (III) acetylacetonate (abbreviation: Ir(piq)$_2$(acac)), (acetylacetonato)bis[2,3-bis(4-fluorophenyl)quinoxalinato]iridium (III) (abbreviation: Ir(Fdpq)z(acac)), (acetylacetonato)bis(3,5-dimethyl-2-phenylpyrazinato)iridium(III) (abbreviation: [Ir(mppr-Me)$_2$(acac)]), (acetylacetonato)bis(5-isopropyl-3-methyl-2-phenylpyrazinato)iridium(III) (abbreviation: [Ir(mppr-iPrh(acac)]), (acetylacetonato)bis(6-tert-butyl-4-phenylpyrimidinato)iridium(III) (abbreviation: [Ir(tBuppm)$_2$(acac)]), (acetylacetonato)bis(4,6-diphenylpyrimidinato)iridium(III) (abbreviation: [Ir(dppm)$_2$(acac)]), 2,3,7,8,12,13,17,18-octaethyl-21H,23H-porphyrin platinum(II) (abbreviation: PtOEP), tris(1,3-diphenyl-1,3-propanedionato) (monophenanthroline)europium(III) (abbreviation: Eu(DBM)$_3$(Phen)), and tris[1-(2-thenoyl)-3,3,3-trifluoroacetonato](monophenanthroline)europium(III) (abbreviation: Eu(TA)$_3$(Phen)).

Preferable examples of the substance (i.e., host material) used for dispersing the light-emitting substance converting triplet excitation energy into luminescence include compounds having an arylamine skeleton, such as 2,3-bis(4-diphenylaminophenyl)quinoxaline (abbreviation: TPAQn) and NPB, carbazole derivatives such as CBP and 4,4',4''-tris(carbazol-9-yl)triphenylamine (abbreviation: TCTA), and metal complexes such as bis[2-(2-hydroxyphenyl)pyridinato]zinc (abbreviation: Znpp$_2$), bis[2-(2-hydroxyphenyl)benzoxazolato]zinc (abbreviation: Zn(BOX)$_2$), bis(2-methyl-8-quinolinolato)(4-phenylphenolato)aluminum (abbreviation: BAlq), and tris(8-quinolinolato)aluminum (abbreviation: Alq$_3$). Alternatively, a high molecular compound such as PVK can be used.

Examples of the TADF material include a fullerene, a derivative thereof, an acridine derivative such as proflavine, and eosin. Other examples include a metal-containing porphyrin, such as a porphyrin containing magnesium (Mg), zinc (Zn), cadmium (Cd), tin (Sn), platinum (Pt), indium (In), or palladium (Pd). Examples of the metal-containing porphyrin include a protoporphyrin-tin fluoride complex (SnF$_2$(Proto IX)), a mesoporphyrin-tin fluoride complex (SnF$_2$(Meso IX)), a hematoporphyrin-tin fluoride complex (SnF$_2$(Hemato IX)), a coproporphyrin tetramethyl ester-tin fluoride complex (SnF$_2$(Copro III-4Me)), an octaethylporphyrin-tin fluoride complex (SnF$_2$(OEP)), an etioporphyrin-tin fluoride complex (SnF$_2$(Etio I)), and an octaethylporphyrin-platinum chloride complex (PtCl$_2$OEP). Alternatively, a heterocyclic compound including a π-electron rich heteroaromatic ring and a π-electron deficient heteroaromatic ring can be used, such as 2-(biphenyl-4-yl)-4,6-bis(12-phenylindolo[2,3-a]carbazol-11-yl)-1,3,5-triazine (PIC-TRZ). Note that a material in which the π-electron rich heteroaromatic ring is directly bonded to the π-electron deficient heteroaromatic ring is particularly preferably used because both the donor property of the π-electron rich heteroaromatic ring and the acceptor property of the π-electron deficient heteroaromatic ring are increased and the energy difference between the S$_1$ level and the T$_1$ level is decreased.

When a host material and the organometallic complex described in Embodiment 1 are included in the light-emitting layer 113 in the presence or absence of any of the light-emitting substances converting singlet excitation energy into luminescence or any of the light-emitting substances converting triplet excitation energy into luminescence (i.e., a guest material), light emission with high emission efficiency can be obtained from the light-emitting layer 113.

The electron-transport layer 114 is a layer containing a substance with a high electron-transport property. For the electron-transport layer 114, a metal complex such as Alq$_3$, tris(4-methyl-8-quinolinolato)aluminum (abbreviation: Almq$_3$), bis(10-hydroxybenzo[h]quinolinato)beryllium (abbreviation: BeBq$_2$), BAlq, Zn(BOX)$_2$, or bis[2-(2-hydroxyphenyl)benzothiazolato]zinc (abbreviation: Zn(BTZ)$_2$) can be used. A heteroaromatic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4'-tert-butylphenyl)-4-phenyl-5-(4''-biphenyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: Bphen), bathocuproine (abbreviation: BCP), or 4,4'-bis(5-methylbenzoxazol-2-yl)stilbene (abbreviation: BzOs) can also be used. A high molecular compound such as poly(2,5-pyridinediyl) (abbreviation: PPy), poly[(9,9-dihexylfluorene-2,7-diyl)-co-(pyridine-3,5-diyl)](abbreviation: PF-Py) or poly[(9,9-dioctylfluorene-2,7-diyl)-co-(2,2'-bipyridine-6,6'-diyl)](abbreviation: PF-BPy) can also be used. The substances listed here are mainly ones that have an electron mobility of $1\times10^{-6}$ cm$^2$/Vs or higher. Note that any substance other than the substances listed here may be used for the electron-transport layer 114 as long as the electron-transport property is higher than the hole-transport property.

The electron-transport layer 114 is not limited to a single layer, but may be a stack of two or more layers each containing any of the substances listed above.

The electron-injection layer 115 is a layer containing a substance with a high electron-injection property. For the electron-injection layer 115, an alkali metal, an alkaline earth metal, or a compound thereof, such as lithium fluoride (LiF), cesium fluoride (CsF), calcium fluoride (CaF$_2$), or lithium oxide (LiO$_x$) can be used. A rare earth metal compound like erbium fluoride (ErF$_3$) can also be used. An electride may also be used for the electron-injection layer 115. Examples of the electride include a substance in which electrons are added at high concentration to calcium oxide-aluminum oxide. Any of the substances for forming the electron-transport layer 114, which are given above, can be used.

A composite material in which an organic compound and an electron donor (donor) are mixed may also be used for the electron-injection layer 115. Such a composite material is excellent in an electron-injection property and an electron-transport property because electrons are generated in the organic compound by the electron donor. In this case, the organic compound is preferably a material that is excellent in transporting the generated electrons. Specifically, for example, the substances for forming the electron-transport layer 114 (e.g., a metal complex or a heteroaromatic compound), which are given above, can be used. As the electron donor, a substance showing an electron-donating property with respect to the organic compound may be used. Preferable examples are an alkali metal, an alkaline earth metal, and a rare earth metal. Specifically, lithium, cesium, magnesium, calcium, erbium, ytterbium, and the like can be used. In addition, an alkali metal oxide or an alkaline earth metal oxide is preferable, and lithium oxide, calcium oxide, and barium oxide are given. A Lewis base such as magnesium oxide can also be used. An organic compound such as tetrathiafulvalene (abbreviation: TTF) can also be used.

Note that each of the above-described hole-injection layer 111, hole-transport layer 112, light-emitting layer 113, electron-transport layer 114, and electron-injection layer 115 can be formed by a method such as an evaporation method (e.g., a vacuum evaporation method), an ink-jet method, or a coating method.

In the above-described light-emitting element, current flows because of a potential difference applied between the first electrode 101 and the second electrode 103 and holes and electrons are recombined in the EL layer 102, whereby light is emitted. Then, the emitted light is extracted outside through one or both of the first electrode 101 and the second electrode 103. Thus, one or both of the first electrode 101 and the second electrode 103 are electrodes having light-transmitting properties.

Note that the light-emitting element described in this embodiment is an example of a light-emitting element in which the organometallic complex obtained by the synthesis method of one embodiment of the present invention is used as an EL material. As a light-emitting device including the above-described light-emitting element, a passive matrix light-emitting device and an active matrix light-emitting device can be fabricated. It is also possible to fabricate a light-emitting device including a light-emitting element having a microcavity structure. Each of the light-emitting devices is one embodiment of the present invention.

The active-matrix type light-emitting device is explained in Embodiment 4.

Note that the structure described in this embodiment can be combined as appropriate with any of the structures described in the other embodiments.

Embodiment 3

Described in this embodiment is a case of fabricating a light-emitting element (hereinafter, a tandem light-emitting element) that has a structure in which a charge-generation layer is provided between a plurality of EL layers and the organometallic complex obtained by the synthesis method of one embodiment of the present invention is used as an EL material in the EL layers.

Figure 2A:
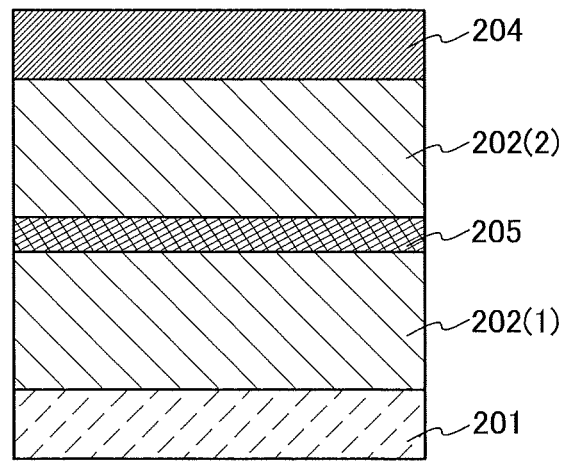
FIGS. 2A and 2B each illustrate a structure of a light-emitting element.

A light-emitting element described in this embodiment is a tandem light-emitting element including a plurality of EL layers (a first EL layer 202(1) and a second EL layer 202(2)) between a pair of electrodes (a first electrode 201 and a second electrode 204) as illustrated in FIG. 2A.

In this embodiment, the first electrode 201 functions as an anode, and the second electrode 204 functions as a cathode. Note that the first electrode 201 and the second electrode 204 can have structures similar to those described in Embodiment 2. In addition, all or any of the plurality of EL layers (the first EL layer 202(1) and the second EL layer 202(2)) may have structures similar to those described in Embodiment 2. In other words, the structures of the first EL layer 202(1) and the second EL layer 202(2) may be the same or different from each other and can be similar to those of the EL layers described in Embodiment 2.

A charge-generation layer 205 is provided between the plurality of EL layers (the first EL layer 202(1) and the second EL layer 202(2)). The charge-generation layer 205 has a function of injecting electrons into one of the EL layers and injecting holes into the other of the EL layers when voltage is applied between the first electrode 201 and the second electrode 204. In this embodiment, when voltage is applied such that the potential of the first electrode 201 is higher than that of the second electrode 204, the charge-generation layer 205 injects electrons into the first EL layer 202(1) and injects holes into the second EL layer 202(2).

Note that in terms of light extraction efficiency, the charge-generation layer 205 preferably has a property of transmitting visible light (specifically, the charge-generation layer 205 has a visible light transmittance of 40% or more). The charge-generation layer 205 functions even when it has lower conductivity than the first electrode 201 or the second electrode 204.

The charge-generation layer 205 may have either a structure in which an electron acceptor (acceptor) is added to an organic compound having a high hole-transport property or a structure in which an electron donor (donor) is added to an organic compound having a high electron-transport property. Alternatively, both of these structures may be stacked.

In the case of the structure in which an electron acceptor is added to an organic compound having a high hole-transport property, as the organic compound having a high hole-transport property, for example, an aromatic amine compound such as NPB, TPD, TDATA, MTDATA, or 4,4'-bis[N-(spiro-9,9'-bifluoren-2-yl)-N-phenylamino]biphenyl (abbreviation: BSPB), or the like can be used. The substances listed here are mainly ones that have a hole mobility of $10^{-6}$ cm$^2$/Vs or higher. Note that any organic compound other than the compounds listed here may be used as long as the hole-transport property is higher than the electron-transport property.

As the electron acceptor, 7,7,8,8-tetracyano-2,3,5,6-tetrafluoroquinodimethane (abbreviation: F$_4$TCNQ), chloranil, and the like can be given. Oxides of metals belonging to Groups 4 to 8 of the periodic table can also be given. Specifically, vanadium oxide, niobium oxide, tantalum oxide, chromium oxide, molybdenum oxide, tungsten oxide, manganese oxide, and rhenium oxide are preferable because of their high electron-accepting properties. Among these, molybdenum oxide is especially preferable because it is stable in the air, has a low hygroscopic property, and is easy to handle.

On the other hand, in the case of the structure in which an electron donor is added to an organic compound having a high electron-transport property, as the organic compound having a high electron-transport property, for example, a metal complex having a quinoline skeleton or a benzoquinoline skeleton, such as Alq, Almq$_3$, BeBq$_2$, or BAlq, or the like can be used. Alternatively, a metal complex having an oxazole-based ligand or a thiazole-based ligand, such as ZnPBO or ZnBTZ can be used. Alternatively, in addition to such a metal complex, PBD, OXD-7, TAZ, Bphen, BCP, or the like can be used. The substances listed here are mainly ones that have an electron mobility of $10^{-6}$ cm$^2$/Vs or higher. Note that any organic compound other than the compounds listed here may be used as long as the electron-transport property is higher than the hole-transport property.

As the electron donor, it is possible to use an alkali metal, a rare earth metal, metals belonging to Groups 2, 3 and 13 of the periodic table, or an oxide or carbonate thereof. Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may be used as the electron donor.

Figure 2B:
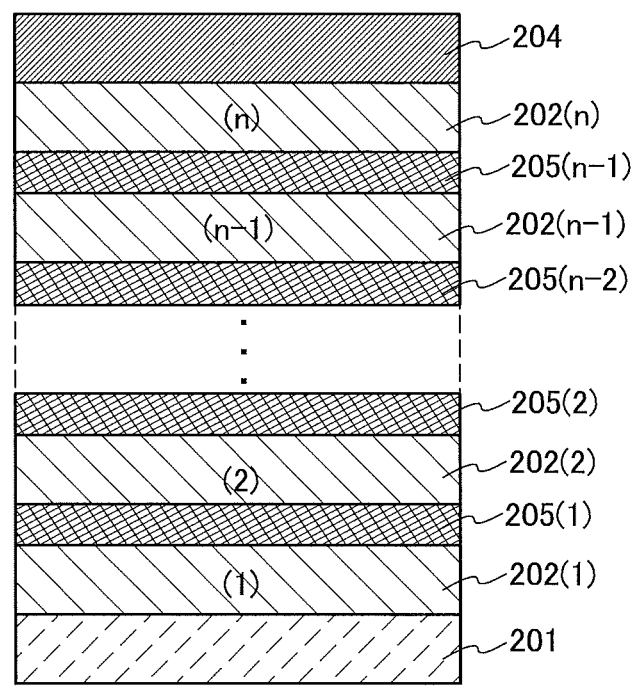

Although the light-emitting element including two EL layers is described in this embodiment, the present invention can be similarly applied to a light-emitting element in which n EL layers (202(1) to 202(n)) (n is three or more) are stacked as illustrated in FIG. 2B. In the case where a plurality of EL layers are included between a pair of electrodes as in the light-emitting element according to this embodiment, by providing charge-generation layers (205(1) to 205(n−1)) between the EL layers, light emission in a high luminance region can be obtained with current density kept low. Since the current density can be kept low, the element can have a long lifetime.

When the EL layers have different emission colors, a desired emission color can be obtained from the whole light-emitting element. For example, in the light-emitting element having two EL layers, when an emission color of the first EL layer and an emission color of the second EL layer are made to be complementary colors, a light-emitting element emitting white light as a whole light-emitting element can also be obtained. Note that "complementary colors" refer to colors that can produce an achromatic color when mixed. In other words, emission of white light can be obtained by mixture of light emitted from substances whose emission colors are complementary colors.

The same can be applied to a light-emitting element having three EL layers. For example, the light-emitting element as a whole can provide white light emission when the emission color of the first EL layer is red, the emission color of the second EL layer is green, and the emission color of the third EL layer is blue.

Note that the structure described in this embodiment can be combined as appropriate with any of the structures described in the other embodiments.

Embodiment 4

Described in this embodiment is a light-emitting device that includes a light-emitting element in which the organometallic complex obtained by the synthesis method of one embodiment of the present invention is used as an EL material in a light-emitting layer.

The light-emitting device may be either a passive matrix type light-emitting device or an active matrix type light-emitting device. Note that any of the light-emitting elements described in the other embodiments can be used for the light-emitting device described in this embodiment.

In this embodiment, an active matrix light-emitting device is described with reference to FIGS. 3A and 3B.

Figure 3A:
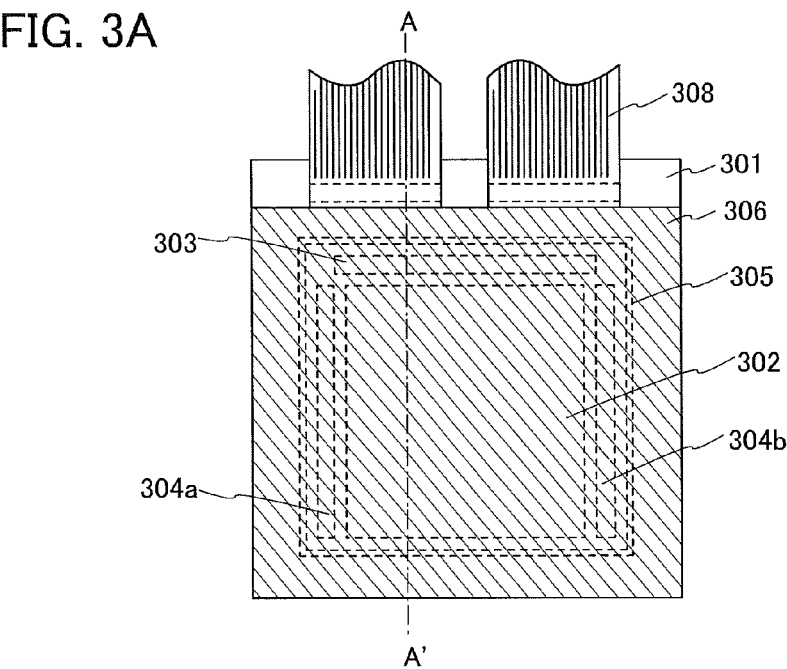
FIGS. 3A and 3B illustrate a light-emitting device.
Figure 3B:
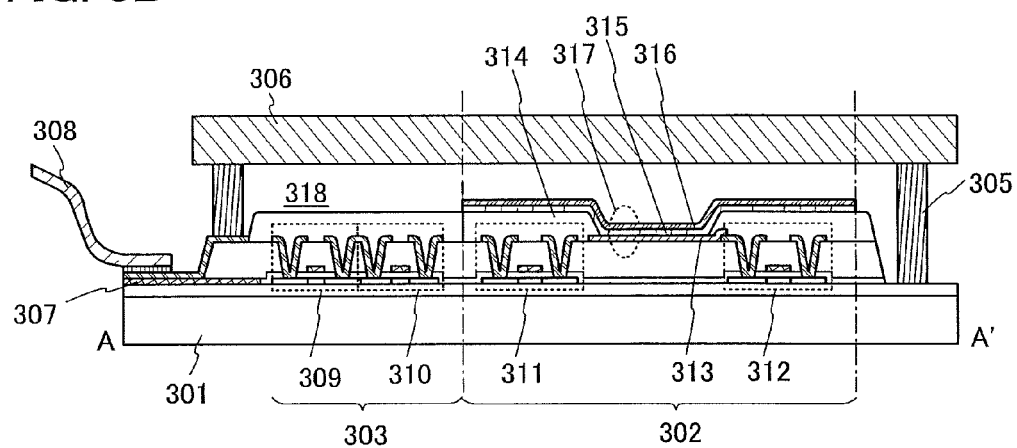

Note that FIG. 3A is a top view illustrating a light-emitting device and FIG. 3B is a cross-sectional view taken along the chain line A-A' in FIG. 3A. The active matrix light-emitting device according to this embodiment includes a pixel portion 302 provided over an element substrate 301, a driver circuit portion (a source line driver circuit) 303, and driver circuit portions (gate line driver circuits) 304a and 304b. The pixel portion 302, the driver circuit portion 303, and the driver circuit portions 304a and 304b are sealed between the element substrate 301 and a sealing substrate 306 with a sealant 305.

Over the element substrate 301, a lead wiring 307 for connecting an external input terminal, through which a signal (e.g., a video signal, a clock signal, a start signal, a reset signal, or the like) or electric potential from the outside is transmitted to the driver circuit portion 303 and the driver circuit portions 304a and 304b, is provided. Here, an example is described in which a flexible printed circuit (FPC) 308 is provided as the external input terminal. Although only the FPC is illustrated here, the FPC may be provided with a printed wiring board (PWB). The light-emitting device in this specification includes, in its category, not only the light-emitting device itself but also the light-emitting device provided with the FPC or the PWB.

Next, a cross-sectional structure is described with reference to FIG. 3B. The driver circuit portion and the pixel portion are formed over the element substrate 301; the driver circuit portion 303 that is the source line driver circuit and the pixel portion 302 are illustrated here.

The driver circuit portion 303 is an example in which an FET 309 and an FET 310 are combined. Note that the driver circuit portion 303 may be formed with a circuit including transistors having the same conductivity type (either an n-channel transistor or a p-channel transistor) or a CMOS circuit including an n-channel transistor and a p-channel transistor. Although this embodiment shows a driver integrated type in which the driver circuit is formed over the substrate, the driver circuit is not necessarily formed over the substrate, and may be formed outside the substrate.

The pixel portion 302 includes a plurality of pixels each of which includes a switching FET 311, a current control FET 312, and a first electrode (anode) 313 that is electrically connected to a wiring (a source electrode or a drain electrode) of the current control FET 312. Although the pixel portion 302 includes two FETs, the switching FET 311 and the current control FET 312, in this embodiment, one embodiment of the present invention is not limited thereto. The pixel portion 302 may include, for example, three or more FETs and a capacitor in combination.

As the FETs 309, 310, 311, and 312, for example, a staggered transistor or an inverted staggered transistor can be used. Examples of a semiconductor material that can be used for the FETs 309, 310, 311, and 312 include Group IV semiconductors (e.g., silicon), Group II semiconductors (e.g., gallium), compound semiconductors, oxide semiconductors, and organic semiconductors. There is no particular limitation on the crystallinity of the semiconductor material, and an amorphous semiconductor or a crystalline semiconductor can be used. An oxide semiconductor is preferably used for the FETs 309, 310, 311, and 312. Examples of the oxide semiconductor include an In—Ga oxide and an In-M-Zn oxide (M is Al, Ga, Y, Zr, La, Ce, or Nd). For example, an oxide semiconductor that has an energy gap of 2 eV or more, preferably 2.5 eV or more, further preferably 3 eV or more is used for the FETs 309, 310, 311, and 312, so that the off-state current of the transistors can be reduced.

An insulator 314 is formed to cover end portions of the first electrode 313. In this embodiment, the insulator 314 is formed using a positive photosensitive acrylic resin. The first electrode 313 is used as an anode in this embodiment.

The insulator 314 preferably has a curved surface with curvature at an upper end portion or a lower end portion thereof. This enables the favorable coverage with a film to be formed over the insulator 314. The insulator 314 can be formed using, for example, either a negative photosensitive resin or a positive photosensitive resin. The material of the insulator 314 is not limited to an organic compound and an inorganic compound such as silicon oxide, silicon oxynitride, or silicon nitride can also be used.

An EL layer 315 and a second electrode (cathode) 316 are stacked over the first electrode (anode) 313. In the EL layer 315, at least a light-emitting layer is provided. In the EL layer 315, a hole-injection layer, a hole-transport layer, an electron-transport layer, an electron-injection layer, a charge-generation layer, and the like can be provided as appropriate in addition to the light-emitting layer.

A light-emitting element 317 is formed of a stack of the first electrode (anode) 313, the EL layer 315, and the second electrode (cathode) 316. For the first electrode (anode) 313, the EL layer 315, and the second electrode (cathode) 316, any of the materials given in Embodiment 2 can be used. Although not illustrated, the second electrode (cathode) 316 is electrically connected to the FPC 308 which is an external input terminal.

Although the cross-sectional view of FIG. 3B illustrates only one light-emitting element 317, a plurality of light-emitting elements are arranged in matrix in the pixel portion 302. Light-emitting elements that emit light of three kinds of colors (R, G, and B) are selectively formed in the pixel portion 302, whereby a light-emitting device capable of full color display can be obtained. In addition to the light-emitting elements that emit light of three kinds of colors (R, G, and B), for example, light-emitting elements that emit light of white (W), yellow (Y), magenta (M), cyan (C), and the like may be formed. For example, the light-emitting elements that emit light of a plurality of kinds of colors are used in combination with the light-emitting elements that emit light of three kinds of colors (R, G, and B), whereby color purity and a reduction in power consumption can be improved. Alternatively, a light-emitting device that is capable of full color display may be fabricated by combination with color filters.

The sealing substrate 306 is attached to the element substrate 301 with the sealant 305, whereby a light-emitting element 317 is provided in a space 318 surrounded by the element substrate 301, the sealing substrate 306, and the sealant 305. Note that the space 318 may be filled with an inert gas (such as nitrogen and argon) or the sealant 305.

An epoxy-based resin or glass frit is preferably used for the sealant 305. The material preferably allows as little moisture and oxygen as possible to penetrate. As the sealing substrate 306, a glass substrate, a quartz substrate, or a plastic substrate formed of fiber-reinforced plastic (FRP), poly(vinyl fluoride) (PVF), a polyester, an acrylic resin, or the like can be used. In the case where glass frit is used as the sealant, the element substrate 301 and the sealing substrate 306 are preferably glass substrates for high adhesion.

As described above, an active matrix light-emitting device can be obtained.

Note that the structure described in this embodiment can be combined as appropriate with any of the structures described in the other embodiments.

Embodiment 5

In this embodiment, examples of an electronic device manufactured using a light-emitting device in which the organometallic complex obtained by the synthesis method of one embodiment of the present invention is used as an EL material are described with reference to FIGS. 4A to 4D.

Examples of electronic devices including the light-emitting device include television devices (also referred to as TV or television receivers), monitors for computers and the like, cameras such as digital cameras and digital video cameras, digital photo frames, mobile phones (also referred to as portable telephone devices), portable game machines, portable information terminals, audio playback devices, and stationary game machines such as pachinko machines. Specific examples of the electronic devices are illustrated in FIGS. 4A to 4D.

FIG. 4A illustrates an example of a television device. In the television device 7100, a display portion 7103 is incorporated in a housing 7101. Images can be displayed by the display portion 7103, and the light-emitting device can be used for the display portion 7103. Here, the housing 7101 is supported by a stand 7105.

The television device 7100 can be operated by an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device 7100 is provided with a receiver, a modem, and the like. With the use of the receiver, general television broadcasts can be received. Moreover, when the television device is connected to a communication network with or without wires via the modem, one-way (from a sender to a receiver) or two-way (between a sender and a receiver or between receivers) information communication can be performed.

FIG. 4B illustrates a computer, which includes a main body 7201, a housing 7202, a display portion 7203, a keyboard 7204, an external connection port 7205, a pointing device 7206, and the like. Note that this computer can be manufactured using the light-emitting device for the display portion 7203.

FIG. 4C illustrates a smart watch, which includes a housing 7302, a display panel 7304, operation buttons 7311 and 7312, a connection terminal 7313, a band 7321, a clasp 7322, and the like.

The display panel 7304 mounted in the housing 7302 serving as a bezel includes a non-rectangular display region. The display panel 7304 can display an icon 7305 indicating time, another icon 7306, and the like.

The smart watch illustrated in FIG. 4C has a variety of functions, for example, a function of displaying a variety of information (e.g., a still image, a moving image; and a text image) on a display portion, a touch panel function, a function of controlling processing with a variety of software (programs), a wireless communication function, and a function of storing data.

The housing 7302 can include a speaker, a sensor (a sensor having a function of measuring or sensing force, displacement, position, speed, acceleration, angular velocity, rotational frequency, distance, light, liquid, magnetism, temperature, chemical substance, sound, hardness, electric field, current, voltage, electric power, radiation, humidity, gradient, oscillation, odor, or infrared rays), a microphone, and the like. Note that the smart watch can be manufactured using the light-emitting device for the display panel 7304.

FIG. 4D illustrates an example of a mobile phone. A mobile phone 7400 includes a housing 7401 provided with a display portion 7402, a microphone 7406, a speaker 7405, a camera 7407, an external connection portion 7404, an operation button 7403, and the like. In the case where the light-emitting element of one embodiment of the present invention is formed over a flexible substrate, the light-emitting element can be used for the display portion 7402 having a curved surface as illustrated in FIG. 4D.

When the display portion 7402 of the mobile phone 7400 illustrated in FIG. 4D is touched with a finger or the like, data can be input to the mobile phone 7400. Operations such as making a call and composing e-mail can be performed by touch on the display portion 7402 with a finger or the like.

There are mainly three screen modes of the display portion 7402. The first mode is a display mode mainly for displaying an image. The second mode is an input mode mainly for inputting data such as characters. The third mode is a display-and-input mode in which two modes of the display mode and the input mode are combined.

For example, in the case of making a call or composing e-mail, a character input mode mainly for inputting characters is selected for the display portion 7402 so that characters displayed on the screen can be input. In this case, it is preferable to display a keyboard or number buttons on almost the entire screen of the display portion 7402.

When a detection device such as a gyro sensor or an acceleration sensor is provided inside the mobile phone 7400, display on the screen of the display portion 7402 can be automatically changed by determining the orientation of the mobile phone 7400 (whether the mobile phone is placed horizontally or vertically).

The screen modes are changed by touch on the display portion 7402 or operation with the button 7403 of the housing 7401. The screen modes can be switched depending on the kind of images displayed on the display portion 7402. For example, when a signal of an image displayed on the display portion is a signal of moving image data, the screen mode is switched to the display mode. When the signal is a signal of text data, the screen mode is switched to the input mode.

In the input mode, when it is determined that input by touch on the display portion 7402 is not performed within a specified period on the basis of a signal detected by an optical sensor in the display portion 7402, the screen mode may be controlled so as to be switched from the input mode to the display mode.

The display portion 7402 may function as an image sensor. For example, an image of a palm print, a fingerprint, or the like is taken by touch on the display portion 7402 with the palm or the finger, whereby personal authentication can be performed. When a sensing light source that emits near-infrared light is provided in the display portion, an image of a finger vein, a palm vein, or the like can be taken.

As described above, the electronic devices can be obtained using the light-emitting device that includes the light-emitting element of one embodiment of the present invention. Note that the light-emitting device can be used for electronic devices in a variety of fields without being limited to the electronic devices described in this embodiment.

Note that the structure described in this embodiment can be combined as appropriate with any of the structures described in the other embodiments.

Embodiment 6

In this embodiment, examples of a lighting device that includes a light-emitting device containing the organometallic complex obtained by the synthesis method of one embodiment of the present invention are described with reference to FIG. 5.

Figure 5:
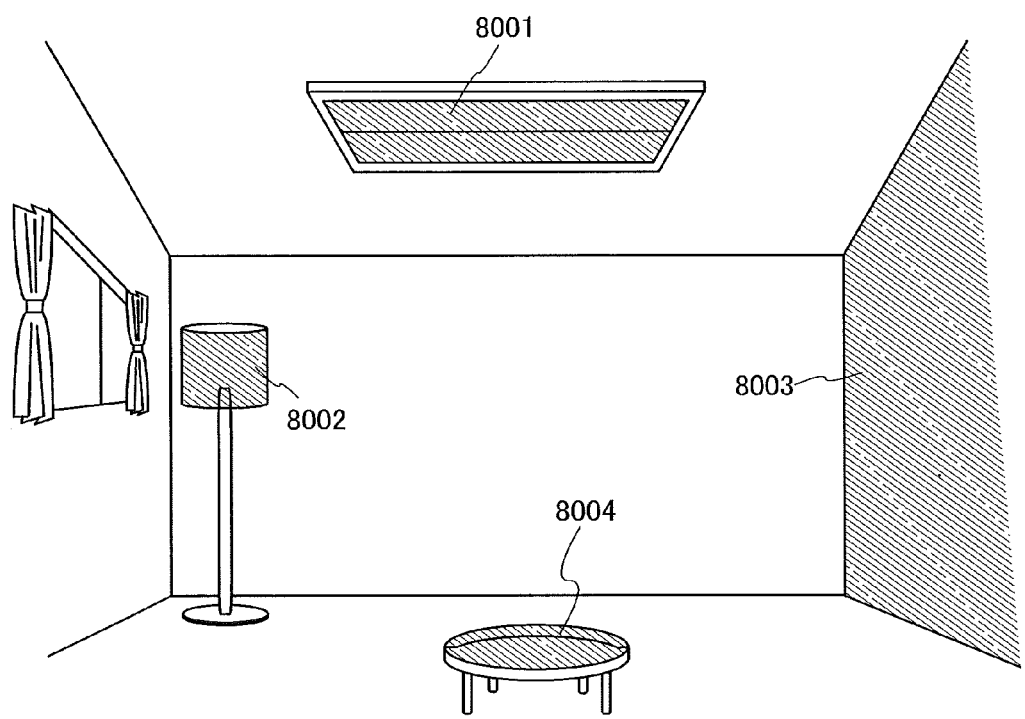
FIG. 5 illustrates lighting devices.

FIG. 5 illustrates an example in which the light-emitting device is used as an indoor lighting device 8001. Since the light-emitting device can have a large area, it can be used for a lighting device having a large area. A lighting device 8002 in which a light-emitting region has a curved surface can also be obtained with the use of a housing with a curved surface. A light-emitting element included in the light-emitting device described in this embodiment can be in a thin film form, which allows the housing to be designed more freely. Thus, the lighting device can be elaborately designed in a variety of ways. A wall of the room may be provided with a large-sized lighting device 8003.

When the light-emitting device is used at a surface of a table, a lighting device 8004 that has a function as a table can be obtained. When the light-emitting device is used as part of other furniture, a lighting device that functions as the furniture can be obtained.

As described above, a variety of lighting devices that include the light-emitting device can be obtained. Note that these lighting devices are also embodiments of the present invention.

Note that the structure described in this embodiment can be combined as appropriate with any of the structures described in the other embodiments.

Example 1

Synthesis Example 1

Described in this example is a synthetic method according to an embodiment of the present invention, leading to an organometallic complex, bis{4,6-dimethyl-2-[5-(2,6-dimethylphenyl)-3-(3,5-dimethylphenyl)-2-pyrazinyl-κN]phenyl-κC}(2,8-dimethyl-4,6-nonanedionato-$κ^2$O,O')iridium (III) (abbreviation: [Ir(dmdppr-dmp)$_2$(divm)]), represented by Structural Formula (300). The structure of [Ir(dmdppr-dmp)$_2$(divm)] is shown below.

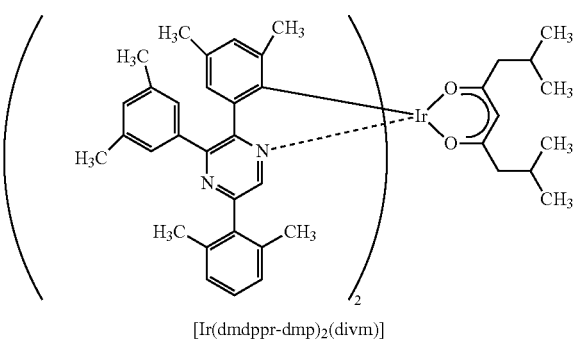

[Ir(dmdppr-dmp)₂(divm)]

Step 1: Synthesis of 5,6-bis(3,5-dimethylphenyl)pyrazin-2-ol

First, 5.33 g (20 mmol) of 3,3',5,5'-tetramethylbenzil, 2.65 g (24 mmol) of glycinamide hydrochloride, 1.92 g (48 mmol) of sodium hydroxide, and 50 mL of methanol were put into a 1-L three-neck flask, and the air in the flask was replaced with nitrogen. This mixture was heated for reflux for approximately 3 hours.

Then, the temperature of the flask was returned to room temperature, 2.5 mL of 12 M concentrated hydrochloric acid was added to this mixture, and stirring was performed for approximately 30 minutes. After that, 2 g of potassium bicarbonate and 25 mL of water were added. Filtration was performed to give a solid and the solid was washed with water and methanol in this order. The resulting residue was dried at 100° C. under reduced pressure and recrystallized with 50 mL of toluene to give 4.83 g of a yellow solid, which was an objective substance, in a yield of 79%.

The synthesis scheme of Step 1 is shown in (a-1).

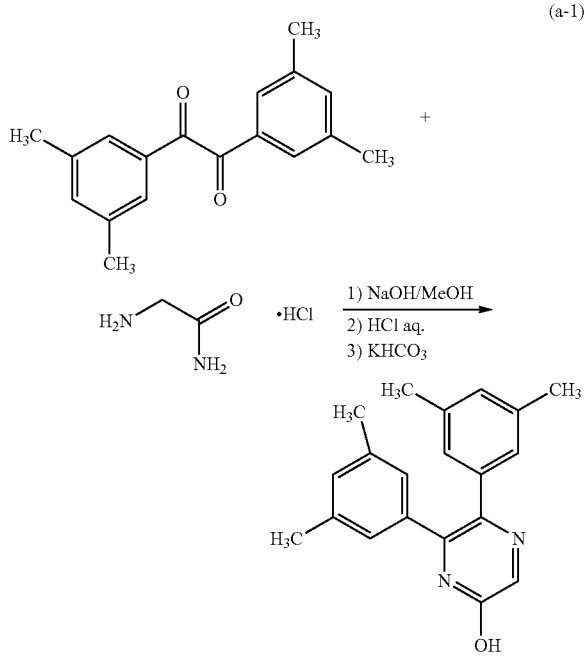

Step 2: Synthesis of 5,6-bis(3,5-dimethylphenyl)-2-pyrazyl triflate

Into a 200-mL three-neck flask was put 3.96 g (13 mmol) of 5,6-bis(3,5-dimethylphenyl)pyrazin-2-ol obtained in Step 1, and the air in the flask was replaced with nitrogen. Then, 65 mL of dichloromethane (abbreviation: DCM) and 3.6 mL of triethylamine (abbreviation: NEt₃) were added under a nitrogen atmosphere. Then, to this solution, 2.8 mL (16.9 mmol) of trifluoromethanesulfonic anhydride (abbreviation: Tf₂O) was added dropwise at 0° C., and the mixture was stirred at 0° C. for 30 minutes and at room temperature for 12 hours.

The flask was cooled again with ice, 30 mL of water was added, and the mixture was separated into an organic layer and an aqueous layer. The aqueous layer was subjected to extraction with dichloromethane. The organic layer and the extract solution were combined, washed with 1 M hydrochloric acid and then a saturated aqueous solution of sodium bicarbonate, added with magnesium sulfate, and subjected to gravity filtration. The solvent in the filtrate was distilled off, and purification was conducted by column chromatography using a mixed solvent of hexane, ethyl acetate, and toluene as a mobile phase; thus, 5.7 g of a yellow-brown oily substance, which was an objective substance, was obtained in a yield of 99%.

The synthesis scheme of Step 2 is shown in (a-2).

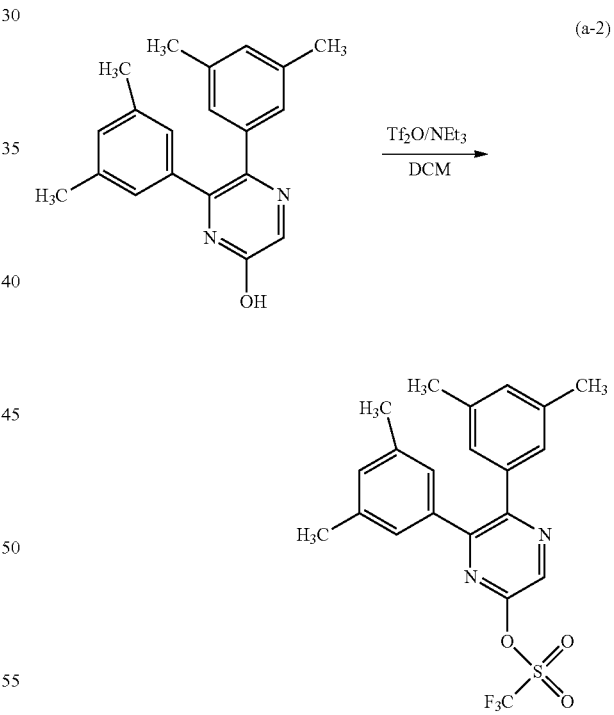

Figure 6:
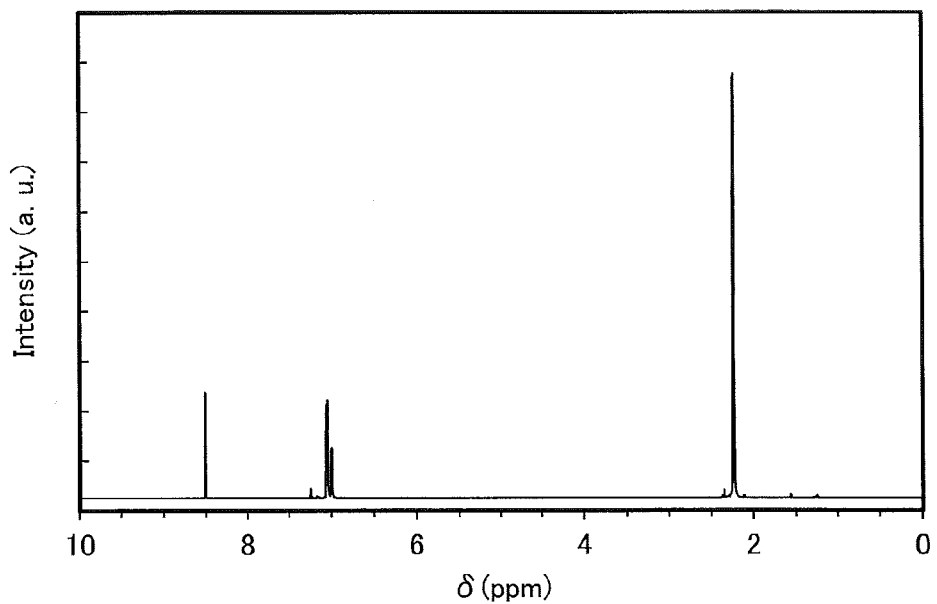
FIG. 6 is a $^1$H-NMR chart of 5,6-bis(3,5-dimethylphenyl)-2-pyrazyl triflate obtained in Step 2 in Example 1.

Results of analysis of the yellow-brown oily substance obtained in Step 2 by nuclear magnetic resonance spectrometry ($^1$H-NMR) are shown below. A $^1$H-NMR chart is shown in FIG. 6. These results show that 5,6-bis(3,5-dimethylphenyl)-2-pyrazyl triflate that is one embodiment of the present invention was synthesized in Step 2.

$^1$H NMR (CDCl₃, 500 MHz): δ (ppm)=2.23 (s, 6H), 2.25 (s, 6H), 7.00 (d, J=5.5 Hz, 2H), 7.06 (d, J=6 Hz, 4H), 8.51 (s, 1H).

Step 3: Synthesis of 5-(2,6-dimethylphenyl)-2,3-bis (3,5-dimethylphenyl)pyrazine (abbreviation: Hdmdppr-dmp)

Next, 2.18 g (5.0 mmol) of 5,6-bis(3,5-dimethylphenyl)-2-pyrazyl triflate obtained in Step 2, 0.90 g (6.0 mmol) of 2,6-dimethylphenylboronic acid, 3.82 g (18 mmol) of tripotassium phosphate, 37 mL of toluene, and 4 mL of water were put into a 200-mL three-neck flask, degassing was performed under reduced pressure, and then the air in the flask was replaced with nitrogen. Then, 46 mg (0.05 mmol) of tris(dibenzylideneacetone)dipalladium(0) (abbreviation: $Pd_2(dba)_3$) and 88 mg (0.20 mmol) of tris(2,6-dimethoxyphenyl)phosphine were added, and the mixture was heated for reflux for 2 hours.

Water and toluene were added to the mixture, and the resulting mixture was separated into an organic layer and an aqueous layer. The aqueous layer was subjected to extraction with toluene. The organic layer and the extract solution were combined, the mixture was washed with water, and then the solvent was distilled off. The resulting residue was purified by column chromatography using a mixed solvent of hexane, ethyl acetate, and toluene as a mobile phase, so that 1.96 g of Hdmdppr-dmp, which was an objective substance, was obtained as a yellowish white solid in a yield of 99%.

The synthesis scheme of Step 3 is shown in (a-3).

Figure 7:
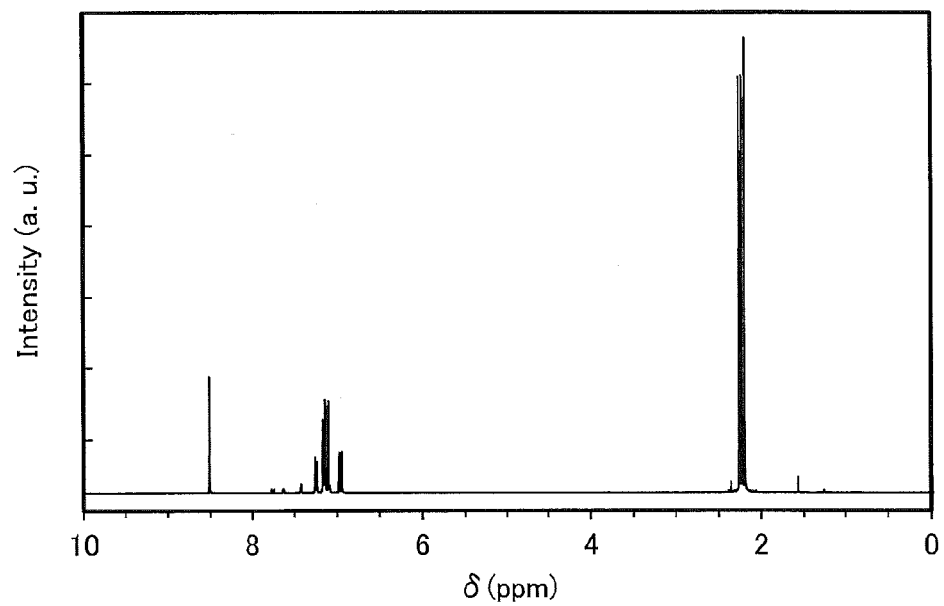
FIG. 7 is a $^1$H-NMR chart of 5-(2,6-dimethylphenyl)-2,3-bis(3,5-dimethylphenyl)pyrazine (Hdmdppr-dmp) obtained in Step 3 in Example 1.

Results of analysis of the yellowish white solid obtained in Step 3 by $^1$H-NMR are shown below. A $^1$H-NMR chart is shown in FIG. 7. These results show that Hdmdppr-dmp, which was a 2,3,5-triarylpyrazine derivative of one embodiment of the present invention, was synthesized in Step 3.

$^1$H NMR ($CDCl_3$, 500 MHz): δ (ppm)=2.19 (s, 6H), 2.23 (s, 6H), 2.26 (s, 6H), 6.96 (d, J=15 Hz, 2H), 7.10 (s, 2H), 7.12-7.18 (m, 4H), 7.22-7.27 (m, 1H), 8.51 (s, 1H).

Step 4: Synthesis of di-μ-chloro-tetrakis{4,6-dimethyl-2-[5-(2,6-dimethylphenyl)-3-(3,5-dimethylphenyl)-2-pyrazinyl-κN]phenyl-κC}diiridium(III) (abbreviation: [Ir(dmdppr-dmp)$_2$Cl]$_2$)

Next, 1.77 g (4.5 mmol) of Hdmdppr-dmp obtained in Step 3, 0.71 g (2.25 mmol) of iridium(III) chloride hydrate, 45 mL of 2-ethoxyethanol, and 15 mL of water were put into a round-bottom flask. The mixture was bubbled with argon for approximately 10 minutes to replace the air in the flask with argon, and heating by irradiation with microwaves (2.45 GHz, 100 W) was performed for 2 hours. Note that in the specification, the irradiation with microwaves was performed using a microwave synthesis system (Discover, manufactured by CEM Corporation).

The solvent in the obtained mixture was distilled off, the residue was suspended in ethanol and filtered, and the resulting solid was washed with ethanol. The resulting solid was dried at 100° C. under reduced pressure, so that 1.84 g of a dinuclear complex [Ir(dmdppr-dmp)$_2$Cl]$_2$, which was an objective substance, was obtained as a red solid in a yield of 81%.

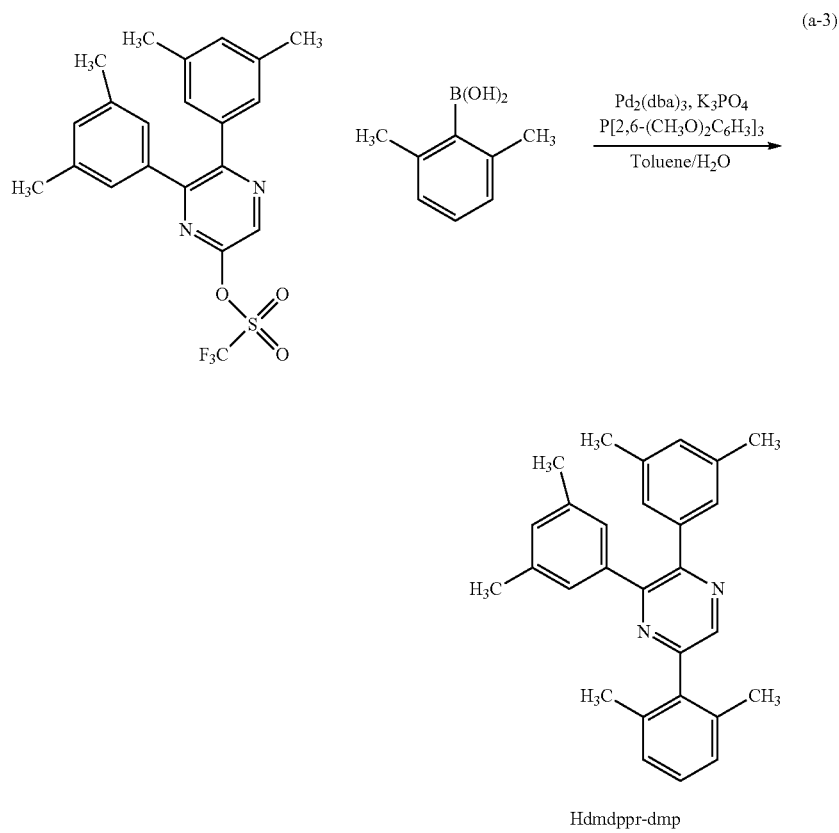

(a-3)

Hdmdppr-dmp

The synthesis scheme of Step 4 is shown in (a-4).

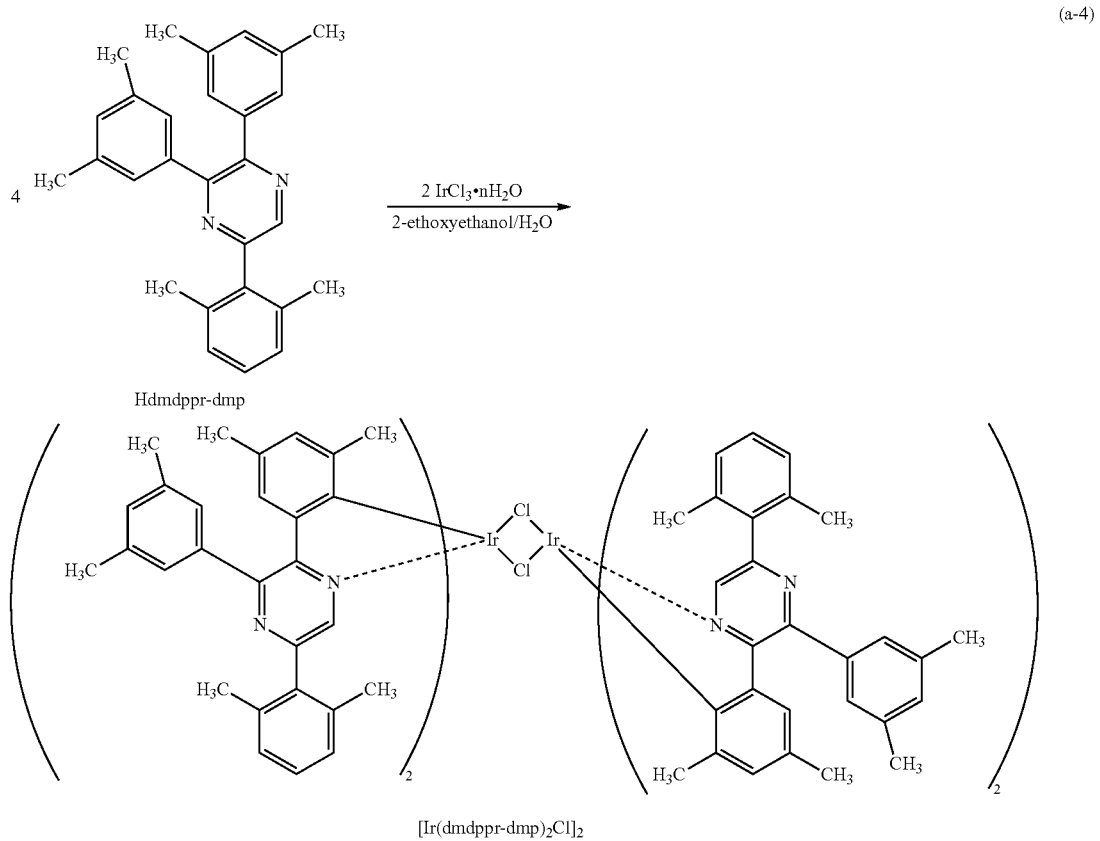

Step 5: Synthesis of [Ir(dmdppr-dmp)₂(divm)]

Then, 1.72 g of [Ir(dmdppr-dmp)₂Cl]₂ obtained in Step 4, 0.47 g of 2,8-dimethyl-4,6-nonanedione (abbreviation: Hdivm), 0.90 g of sodium carbonate, and 9 mL of 2-ethoxyethanol were put into a round-bottom flask, and the mixture was bubbled with argon for approximately 10 minutes to replace the air in the flask with argon. After that, irradiation with microwaves (2.45 GHz, 120 W) was performed for 2 hours. The solvent was distilled off from the obtained mixture, and the resulting residue was suspended in methanol, filtered, and washed with water and methanol.

The obtained solid was dissolved in dichloromethane, and filtered through a filter aid in which Celite, alumina, and Celite were stacked in this order. The solvent in the filtrate was distilled off, recrystallization was performed using dichloromethane and methanol, and the resulting solid was dried by heating at 100° C. under reduced pressure, so that 1.42 g of the organometallic complex [Ir(dmdppr-dmp)₂(divm)] was obtained as a dark red powder in a yield of 72%.

The synthesis scheme of Step 5 is shown in (a-5) below.

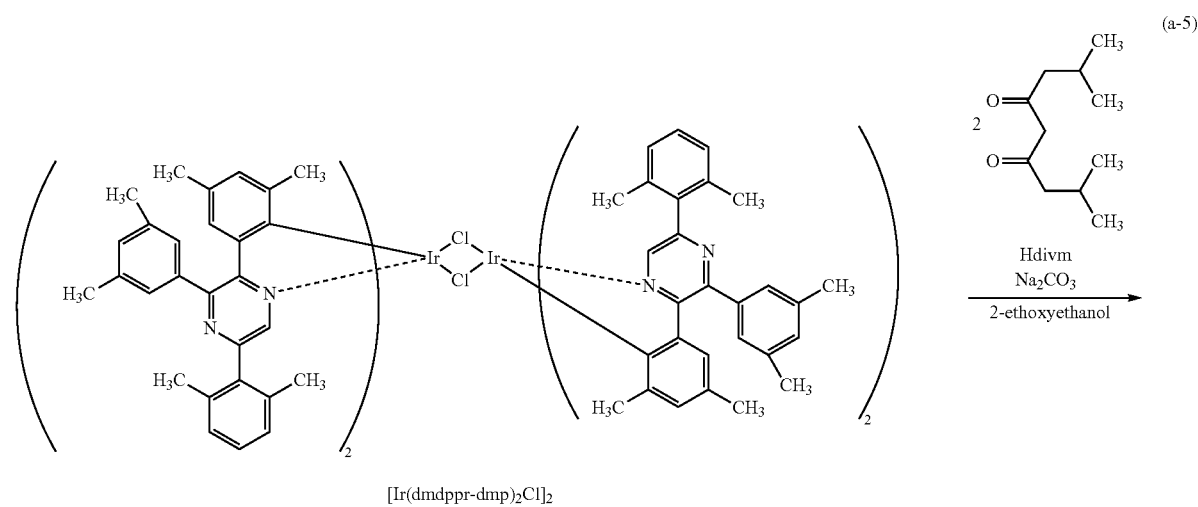

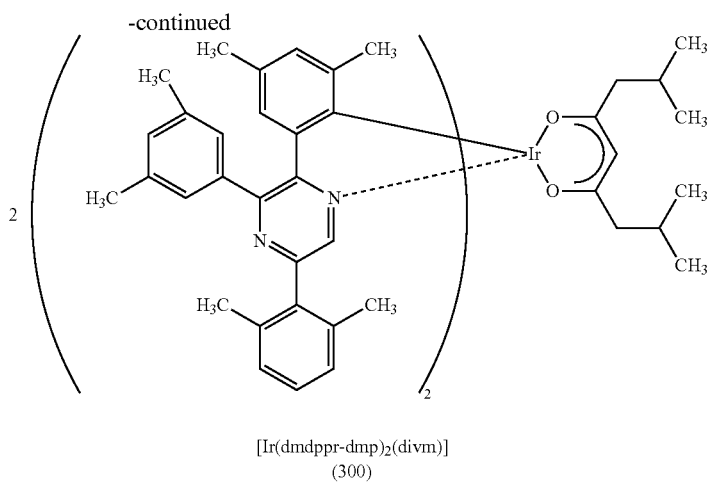

[Ir(dmdppr-dmp)₂(divm)]
(300)

Figure 8:
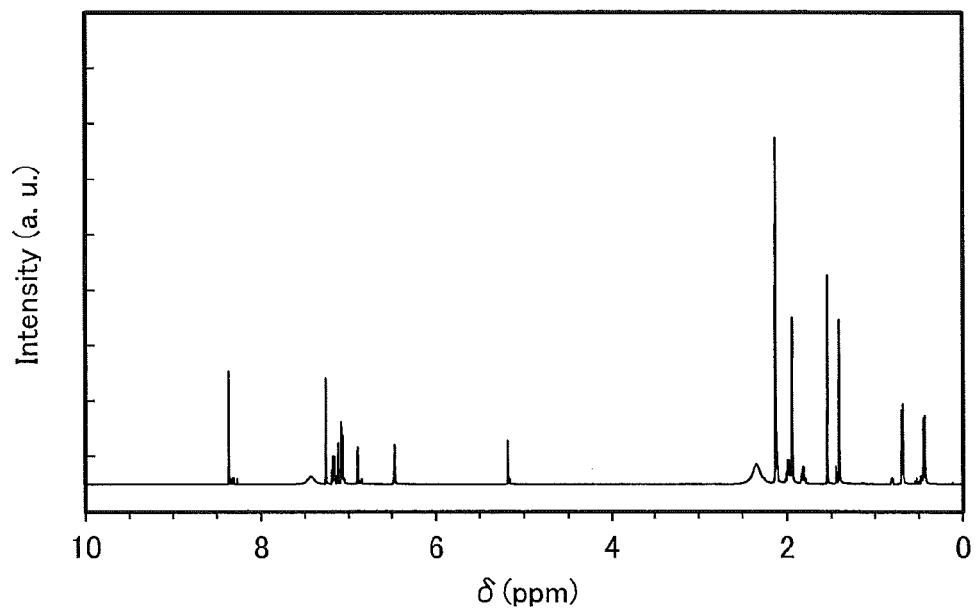
FIG. 8 is a $^1$H-NMR chart of an organometallic complex represented by Structural Formula (300).

Results of analysis of the dark red powder obtained in Step 5 by ¹H-NMR are shown below. A ¹H-NMR chart is shown in FIG. 8. These results show that an organometallic complex [Ir(dmdppr-dmp)₂(divm)](Structural Formula (300)) was synthesized in Step 5.

¹H NMR (CDCl₃, 500 MHz): δ (ppm)=0.56-0.63 (dd, 121H), 1.79-1.84 (m, 2H), 1.92 (s, 4H), 2.22 (s, 12H), 5.19 (s, 1H), 6.46-6.47 (d, 2H), 6.52-6.55 (dt, 2H), 6.65-6.68 (t, 2H), 6.93-6.95 (d, 2H), 7.12-7.14 (d, 4H), 7.20-7.22 (d, 2H), 7.51 (s, 6H), 7.73 (s, 4H), 8.48 (s, 2H).

Example 2

Synthesis Example 2

Described in this example is a synthetic method according to an embodiment of the present invention, leading to an organometallic complex, bis[2-(3,5-diphenyl-2-pyrazinyl-κN)-phenyl-κC](2,2,6,6-tetramethyl-3,5-heptanedionato-κ²O,O')iridium(III) (abbreviation: [Ir(tppr)₂(dpm)]), represented by Structural Formula (310). The structure of [Ir(tppr(dpm)] is shown below.

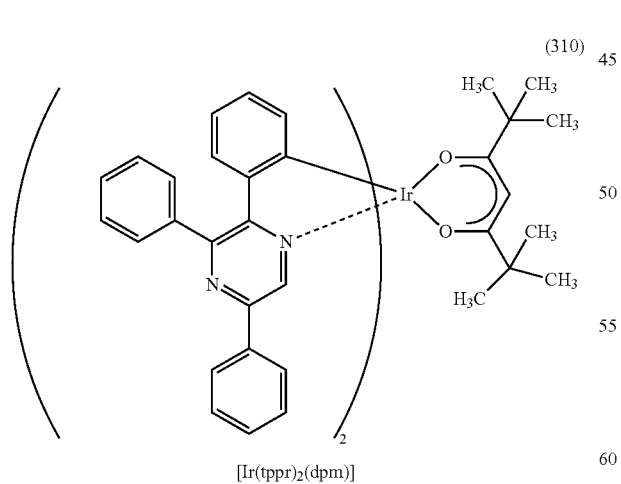

[Ir(tppr)₂(dpm)]

Step 1: Synthesis of 5,6-diphenylpyrazin-2-ol

First, 21.0 g (100 mmol) of benzil, 13.3 g (120 mmol) of glycinamide hydrochloride, 9.6 g (240 mmol) of sodium hydroxide, and 500 mL of methanol were put into a 1-L three-neck flask, and the air in the flask was replaced with nitrogen. This mixture was heated for reflux for approximately 3 hours.

Then, the temperature of the flask was returned to room temperature, 12.5 mL of 12 M concentrated hydrochloric acid was added to this mixture, and stirring was performed for approximately 30 minutes. Then, 10 g of potassium bicarbonate and 125 mL of water were added. Filtration was performed to give a solid, and the solid was washed with water and methanol in this order. The resulting residue was dried at 100° C. under reduced pressure and recrystallized with 50 mL of toluene to give 19.5 g of a yellow solid, which was an objective substance, in a yield of 79%.

The synthesis scheme of Step 1 is shown in (b-1).

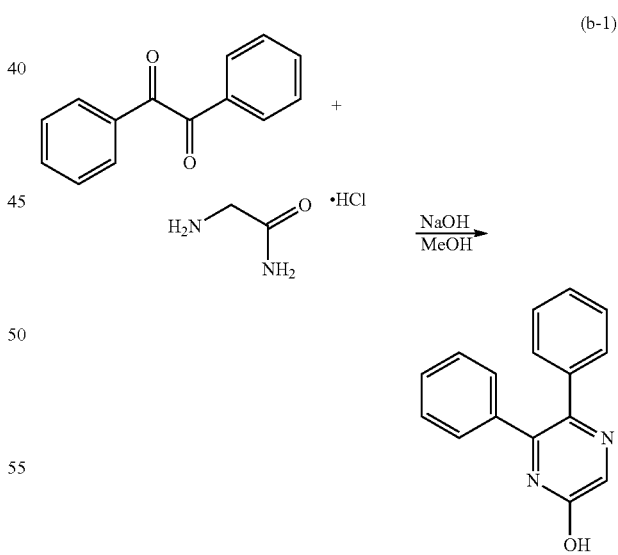

Step 2: Synthesis of 5,6-diphenyl-2-pyrazyl triflate

Into a 2-L three-neck flask was put 18.6 g (75 mmol) of 5,6-diphenylpyrazin-2-ol obtained in Step 1, and the air in the flask was replaced with nitrogen. Then, 750 mL of dichloromethane and 21 mL of triethylamine were added under a nitrogen atmosphere, 16.4 mL (97.5 mmol) of trifluoromethanesulfonic anhydride was added dropwise to this solution at 0° C., and the mixture was stirred at 0° C. for 30 minutes and at room temperature for 12 hours.

The flask was cooled again with ice, 250 mL of water was added, and the mixture was separated into an organic layer and an aqueous layer. The aqueous layer was subjected to extraction with dichloromethane. The organic layer and the extract solution were combined, washed with 1 M hydrochloric acid and then a saturated aqueous solution of sodium bicarbonate, added with magnesium sulfate, and subjected to gravity filtration. The solvent in the filtrate was distilled off, and the obtained residue was purified by column chromatography using a mixed solvent of hexane, ethyl acetate, and toluene as a mobile phase; thus, 27.8 g of a yellow-brown oily substance, which was an objective substance, was obtained in a yield of 97%.

The synthesis scheme of Step 2 is shown in (b-2).

combined, the mixture was washed with water, and then the solvent was distilled off. The resulting residue was purified by column chromatography using a mixed solvent of hexane, ethyl acetate, and toluene as a mobile phase, so that 10.0 g of Htppr, which was an objective substance, was obtained as a yellowish white solid in a yield of 93%.

The synthesis scheme of Step 3 is shown in (b-3).

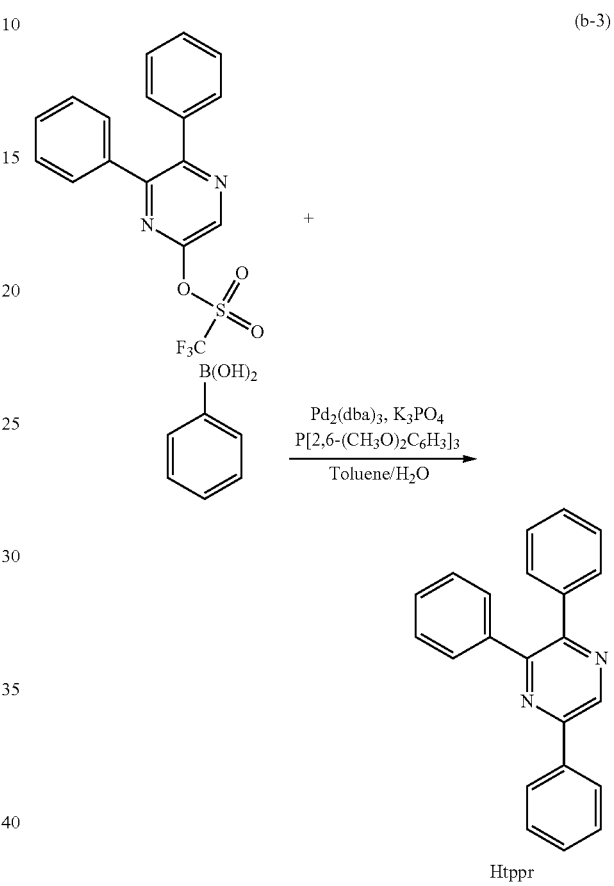

(b-3)

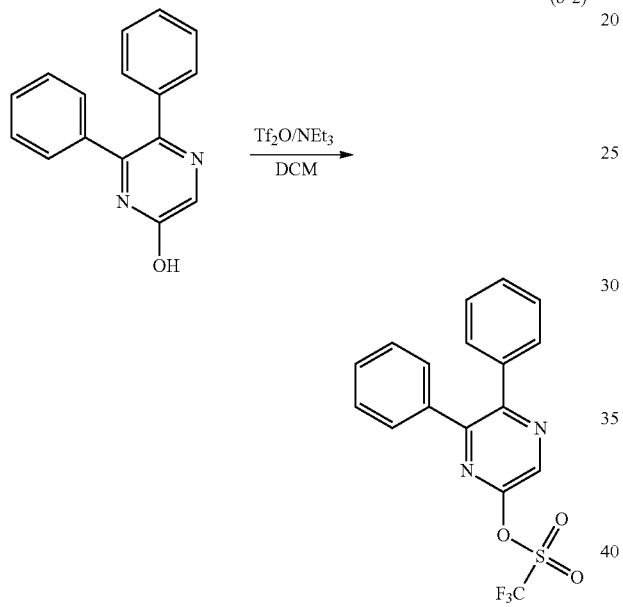

(b-2)

Figure 9:
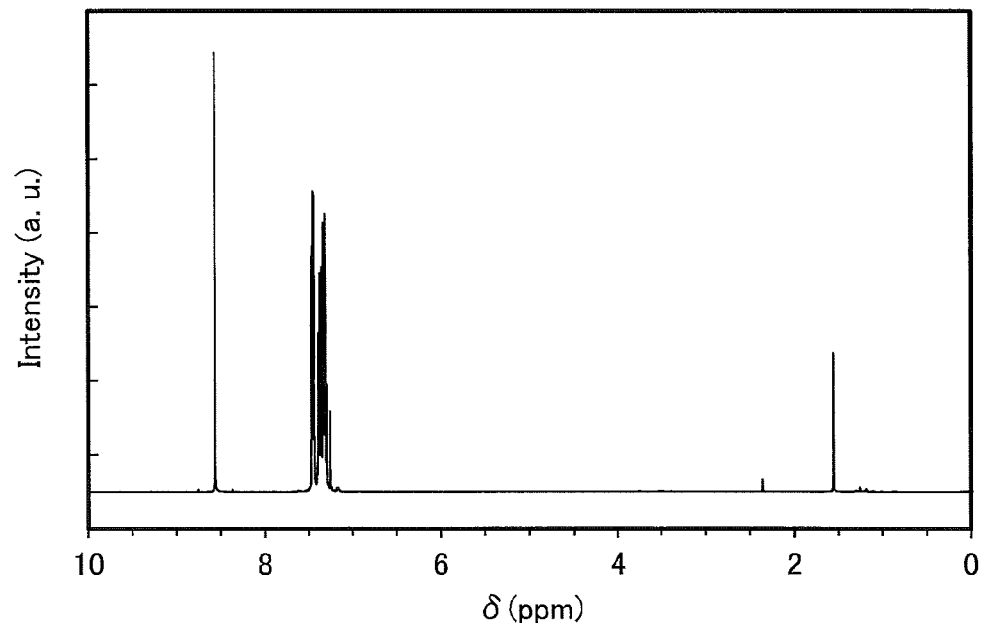
FIG. 9 is a $^1$H-NMR chart of 5,6-diphenyl-2-pyrazyl triflate obtained in Step 2 in Example 2.

Results of analysis of the yellow-brown oily substance obtained in Step 2 by $^1$H-NMR are shown below. A $^1$H-NMR chart is shown in FIG. 9. These results show that 5,6-diphenyl-2-pyrazyl triflate that is one embodiment of the present invention was synthesized in Step 2.

$^1$H NMR (CDCl$_3$, 500 MHz): δ (ppm)=7.28-7.41 (m, 6H), 7.42-7.48 (m, 4H), 8.56 (s, 1H).

Step 3: Synthesis of 2,3,5-triphenylpyrazine (abbreviation: Htppr)

Next, 13.3 g (35 mmol) of 5,6-diphenyl-2-pyrazyl triflate obtained in Step 2, 5.12 g (42 mmol) of phenylboronic acid, 26.8 g (126 mmol) of tripotassium phosphate, 260 mL of toluene, and 26 mL of water were put into a 500-mL three-neck flask, degassing was performed under reduced pressure, and then the air in the flask was replaced with nitrogen. Then, 321 mg (0.35 mmol) of tris(dibenzylideneacetone)dipalladium(0) (abbreviation: Pd$_2$(dba)$_3$) and 619 mg (1.40 mmol) of tris(2,6-dimethoxyphenyl)phosphine were added, and the mixture was heated for reflux for 2 hours.

Figure 10:
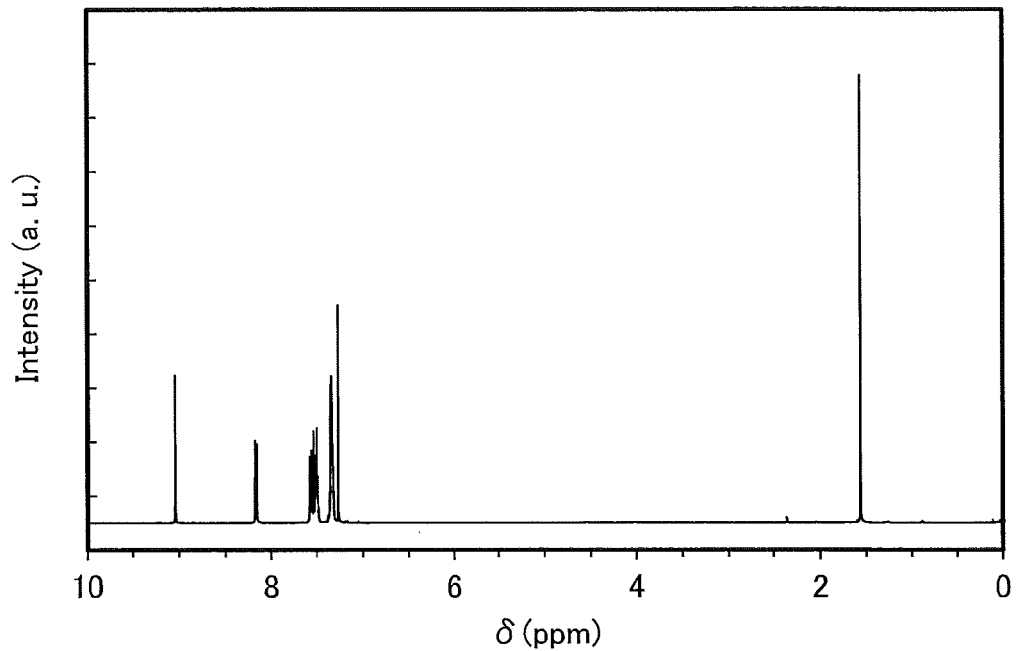
FIG. 10 is a $^1$H-NMR chart of 2,3,5-triphenylpyrazine (Htppr) obtained in Step 3 in Example 2.

Water and toluene were added to the mixture, and the resulting mixture was separated into an organic layer and an aqueous layer. The aqueous layer was subjected to extraction with toluene. The organic layer and the extract solution were Results of analysis of the yellowish white solid obtained in Step 3 by $^1$H-NMR are shown below. A $^1$H-NMR chart is shown in FIG. 10. These results show that Htppr, which was a 2,3,5-triarylpyrazine derivative of one embodiment of the present invention, was synthesized in Step 3.

$^1$H NMR (CDCl$_3$, 500 MHz): δ (ppm)=7.28-7.38 (m, 6H), 7.46-7.59 (m, 7H), 8.17 (d, J=7.5 Hz, 2H), 9.04 (s, 1H).

Step 4: Synthesis of di-μ-chloro-tetrakis[2-(3,5-diphenyl-2-pyrazinyl-κN)phenyl-κC]diiridium(III) (abbreviation: [Ir(tppr)$_2$Cl]$_2$)

Next, 9.25 g (30 mmol) of Htppr obtained in Step 3, 4.75 g (15 mmol) of iridium(III) chloride hydrate, 300 mL of 2-ethoxyethanol, and 100 mL of water were put into a 1-L three-neck flask. The mixture was bubbled with argon for approximately 10 minutes to replace the air in the flask with argon, and heating by irradiation with microwaves (2.45 GHz, 400 W) was performed for 3 hours.

The obtained mixture was filtered, and the residue was washed with ethanol. The resulting solid was dried at 100° C. under reduced pressure, so that 10.3 g of a dinuclear complex [Ir(tppr)$_2$Cl]$_2$, which was an objective substance, was obtained as a red solid in a yield of 82%.

The synthesis scheme of Step 4 is shown in (b-4).

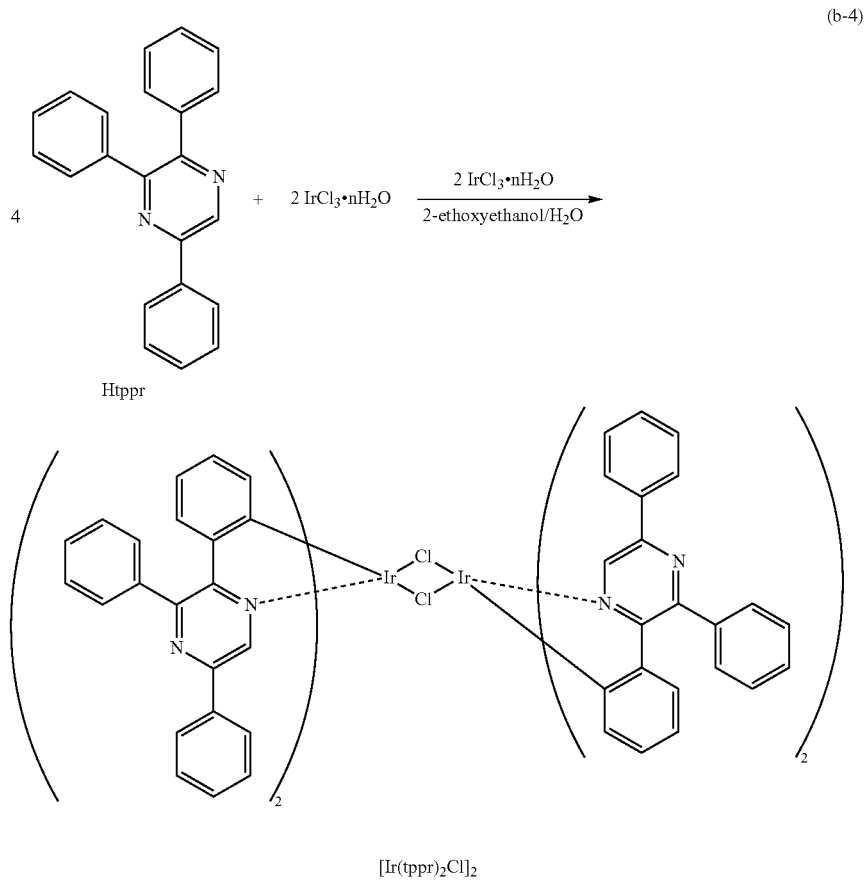

Step 5: Synthesis of [Ir(tppr)$_2$(dpm)]

Then, 10.1 g of [Ir(tppr)$_2$Cl]$_2$ obtained in Step 4, 3.32 g of 2,2,6,6-tetramethyl-3,5-heptanedione (abbreviation: Hdpm), 6.36 g of sodium carbonate, and 60 mL of 2-ethoxyethanol were put into a 300-mL three-neck flask, and the mixture was bubbled with argon for approximately 10 minutes to replace the air in the flask with argon. After that, irradiation with microwaves (2.45 GHz, 400 W) was performed for 1 hour. The obtained mixture was filtered, and the resulting solid was washed with ethanol, water, and ethanol in this order.

The obtained solid was dissolved in dichloromethane, and filtered through a filter aid in which Celite, alumina, and Celite were stacked in this order. The solvent in the filtrate was distilled off, recrystallization was performed using dichloromethane and methanol, and the resulting solid was dried by being heated at 100° C. under reduced pressure, so that 11.1 g of the organometallic complex [Ir(tppr)$_2$(dpm)] was obtained as a dark red powder in a yield of 93%.

The synthesis scheme of Step 5 is shown in (b-5) below.

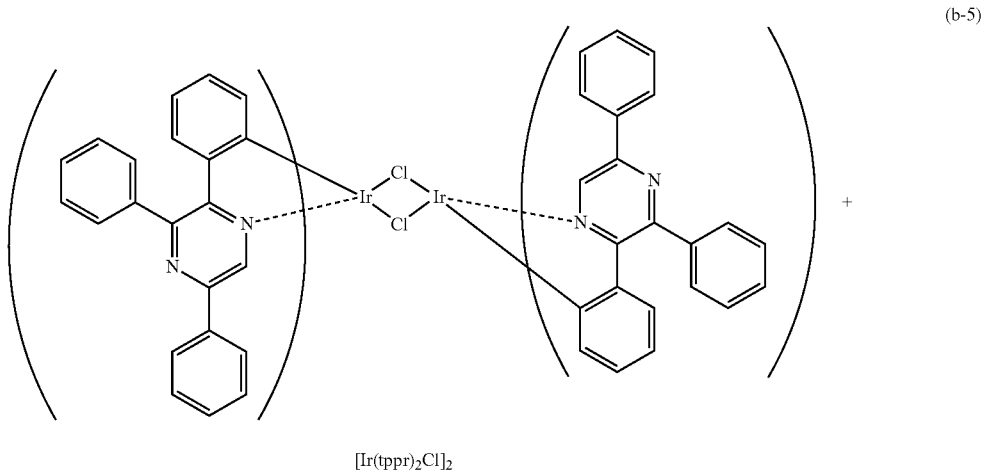

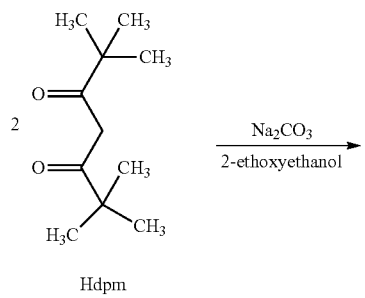

Hdpm

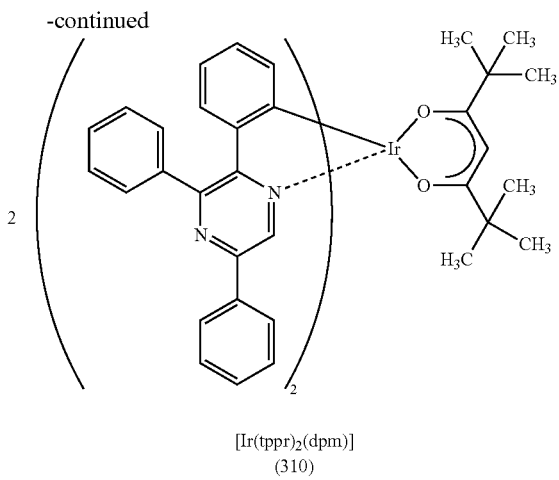

[Ir(tppr)₂(dpm)]
(310)

Figure 11:
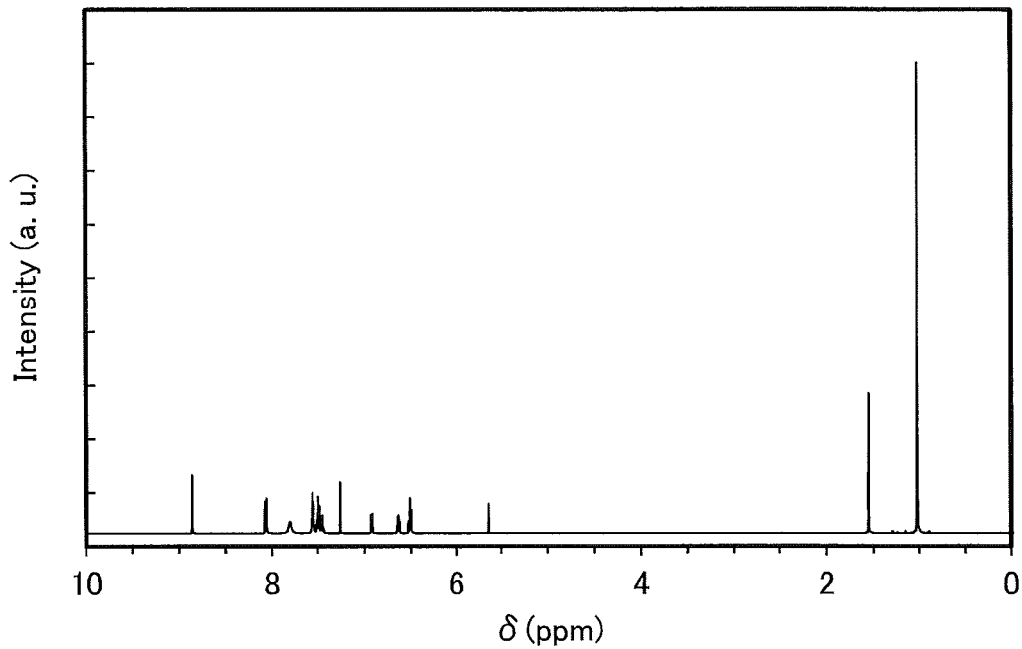
FIG. 11 is a $^1$H-NMR chart of an organometallic complex represented by Structural Formula (310).

Results of analysis of the dark red powder obtained in Step 5 by $^1$H-NMR are shown below. A $^1$H-NMR chart is shown in FIG. 11. These results show that an organometallic complex [Ir(tppr)₂(dpm)](Structural Formula (310)) was synthesized in Step 5.

$^1$H NMR (CDC$_3$, 500 MHz): δ (ppm)=1.02 (s, 18H), 5.63 (s, 1H), 6.51 (t, J=7.5 Hz, 4H), 6.64 (t, J=7.5 Hz, 2H), 6.92 (d, J=8.0 Hz, 2H), 7.42-7.53 (m, 6H), 7.54-7.59 (br, 6H), 7.76-7.85 (br, 4H), 8.07 (d, J=6.5 Hz, 4H), 8.86 (s, 2H).

Example 3

Synthesis Example 3

Described in this example is a synthetic method according to an embodiment of the present invention, leading to an organometallic complex, bis{2-[5-(2,6-dimethylphenyl)-3-phenyl-2-pyrazinyl-κN]-phenyl-κC}(2,8-dimethyl-4,6-nonanedionato-κ$^2$O,O')iridium(III) (abbreviation: [Ir(dppr-dmp)₂(divm)]), represented by Structural Formula (312). The structure of [Ir(dppr-dmp)₂(divm)] is shown below.

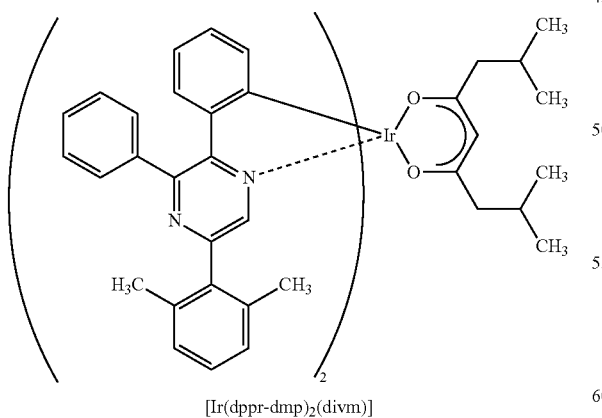

[Ir(dppr-dmp)₂(divm)]

Step 1: Synthesis of 5,6-diphenylpyrazin-2-ol

First, 4.2 g (20 mmol) of benzil, 2.21 g (20 mmol) of glycinamide hydrochloride, and 40 mL of methanol were put into a three-neck flask equipped with a reflux pipe, the air in the flask was replaced with nitrogen, the mixture was refluxed, an aqueous solution of 1.6 g (40 mmol) of sodium hydroxide in 3.2 mL of water was added, and the reflux was continued for 3 hours. Then, stirring was performed until the temperature of the flask was returned to room temperature. After that, 2.5 mL of 12M concentrated hydrochloric acid, 2 g of potassium bicarbonate, and 25 mL of water were added to this mixture, and filtration was performed.

The obtained residue was dried at 100° C. under reduced pressure and purified by silica gel column chromatography using chloroform and ethyl acetate in a 5:2 ratio as a developing solvent. The solvent in the solution was distilled off and the resulting residue was recrystallized with hexane; thus, 3.04 g of a yellow solid, which was an objective substance, was obtained in a yield of 89%.

The synthesis scheme of Step 1 is shown in (c-1) below.

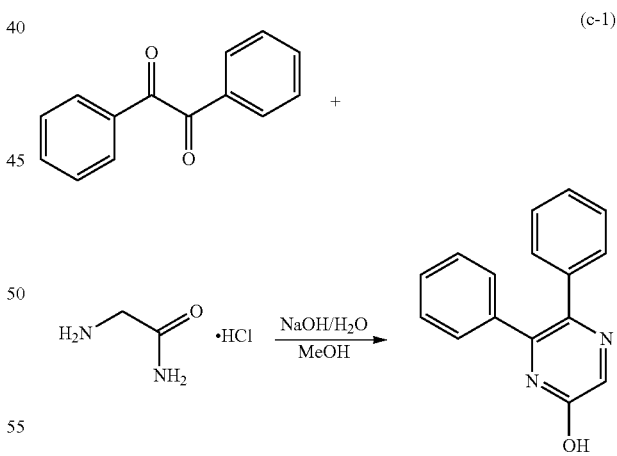

(c-1)

Step 2: Synthesis of 5,6-diphenyl-2-pyrazyl triflate

Into a three-neck flask were put 2.48 g (10 mmol) of 5,6-diphenylpyrazin-2-ol obtained in Step 1, 100 mL of dichloromethane, and 2.8 mL of triethylamine. The air in the flask was replaced with nitrogen, and 2.4 mL of trifluoromethanesulfonic anhydride was added dropwise at 0° C. The mixture was stirred at 0° C. for 1.5 hours and at room temperature for 12 hours.

After the reaction, while the flask was cooled with ice, 30 mL of water was added to the mixture, and the organic layer was extracted with dichloromethane. The extract was washed with a saturated aqueous solution of sodium bicarbonate. Magnesium sulfate was added and gravity filtration was performed. The solvent in the filtrate was distilled off and the resulting residue was purified by silica gel column chromatography using hexane, ethyl acetate, and toluene in a 20:2:10 ratio as a developing solvent. Thus, 3.73 g of a yellow-brown oily substance, which was an objective substance, was obtained in a yield of 98%.

A synthesis scheme of Step 2 is shown in (c-2) below.

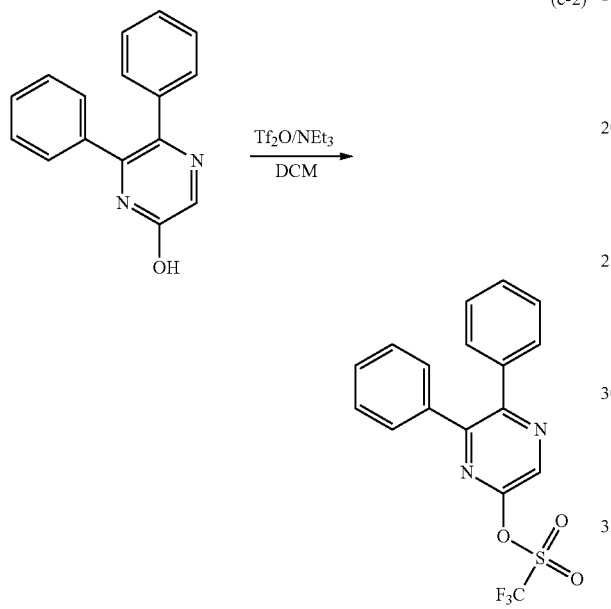

The result of the $^1$H-NMR analysis of the yellow-brown oily substance obtained in Step 2 was the same as that obtained in Step 2 of Example 2. That is, 5,6-diphenyl-2-pyrazyl triflate that is one embodiment of the present invention was also synthesized in Step 2 of Example 3.

Step 3: Synthesis of
2-(2,6-dimethylphenyl)-5,6-diphenylpyrazine
(abbreviation: Hdppr-dmp)

Next, 2.66 g (7.0 mmol) of 5,6-diphenyl-2-pyrazyl triflate obtained in Step 2, 2.10 g (14 mmol) of 2,6-dimethylphenylboronic acid, 2.23 g (21.0 mmol) of sodium carbonate, 24 mL of N,N-dimethylformamide (abbreviation: DMF), and 24 mL of water were put into a round-bottom flask equipped with a reflux pipe, the air in the flask was replaced with nitrogen, 49.1 mg (0.07 mmol) of bis(triphenylphosphine)palladium (II) dichloride (abbreviation: PdCl$_2$(PPh$_3$)$_2$) was added, and irradiation with microwaves (2.45 GHz, 100 W) was performed for 2 hours.

To the resulting mixture, 25 mg (0.035 mmol) of PdCl$_2$(PPh$_3$)$_2$ was added again, and the mixture was irradiated with microwaves (2.45 GHz, 100 W) for 2 hours. Furthermore, 25 mg (0.035 mmol) of PdCl$_2$(PPh$_3$)$_2$ and 1.1 g (7.0 mmol) of 2,6-dimethylphenylboronic acid were added and irradiation with microwaves (2.45 GHz, 100 W) was performed for 2 hours. Water was added to the resulting mixture, and the organic layer was extracted with toluene. The extract solution was washed with water, and the solvent was distilled off. The resulting residue was purified by silica gel column chromatography using hexane, ethyl acetate, and toluene in a 20:2:10 ratio as a developing solvent, so that Hdppr-dmp, which was an objective pyrazine derivative, was obtained as a yellowish white solid in a yield of 38%.

A synthesis scheme of Step 3 is shown in (c-3) below.

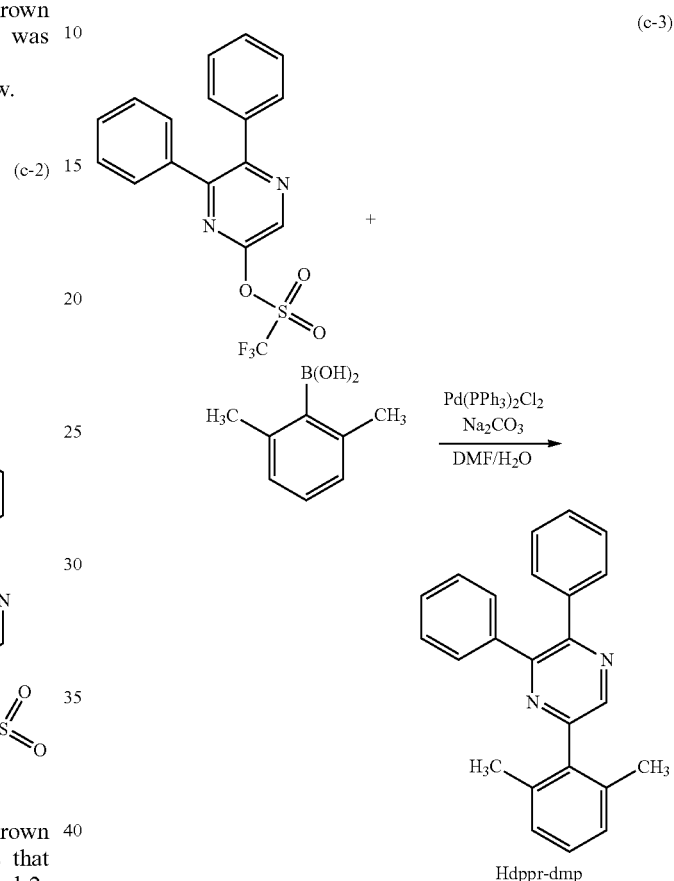

Figure 12:
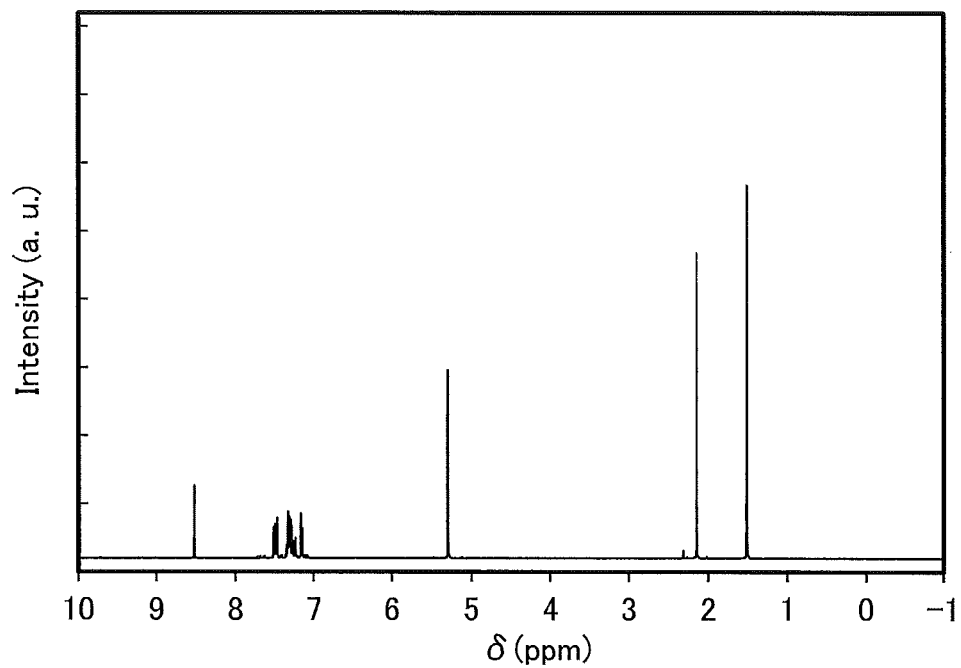
FIG. 12 is a $^1$H-NMR chart of 5,6-diphenyl-2-pyrazyl triflate obtained in Step 3 in Example 3.

Results of analysis of the yellowish white solid obtained in Step 3 by $^1$H-NMR are shown below. A $^1$H-NMR chart is shown in FIG. 12. These results show that Hdppr-dmp, which was a synthetic intermediate and a 2,3,5-triarylpyrazine derivative of one embodiment of the present invention, was synthesized in Step 3.

$^1$H NMR (CDCl$_3$, 500 MHz): δ (ppm)=2.15 (s, 6H), 7.16 (d, 2H), 7.26-7.34 (m, 7H), 7.47 (d, 2H), 7.50 (d, 2H), 8.52 (s, 1H).

Step 4: Synthesis of di-µ-chloro-tetrakis{2-[5-(2,6-dimethylphenyl)-3-phenyl-2-pyrazinyl-κN]-phenyl-κC}diiridium(III) (abbreviation: [Ir(dppr-dmp)$_2$Cl]$_2$)

Next, 0.84 g (2.5 mmol) of Hdppr-dmp obtained in Step 3, 0.38 g (1.2 mmol) of iridium(III) chloride hydrate, 30 mL of 2-ethoxyethanol, and 10 mL of water were put into a round-bottom flask equipped with a reflux pipe. The air in the flask was replaced with argon, and heating by irradiation with microwaves (2.45 GHz, 100 W) was performed for 2 hours.

The solvent in the resulting mixture was distilled off and the resulting residue was washed with methanol; thus, 0.46 g of a dinuclear complex [Ir(dppr-dmp)$_2$Cl]$_2$, which was an objective substance, was obtained as a dark red powder solid in a yield of 41%.

The synthesis scheme of Step 4 is shown in (c-4) below.

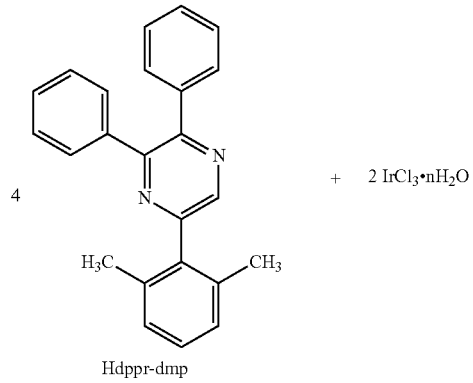

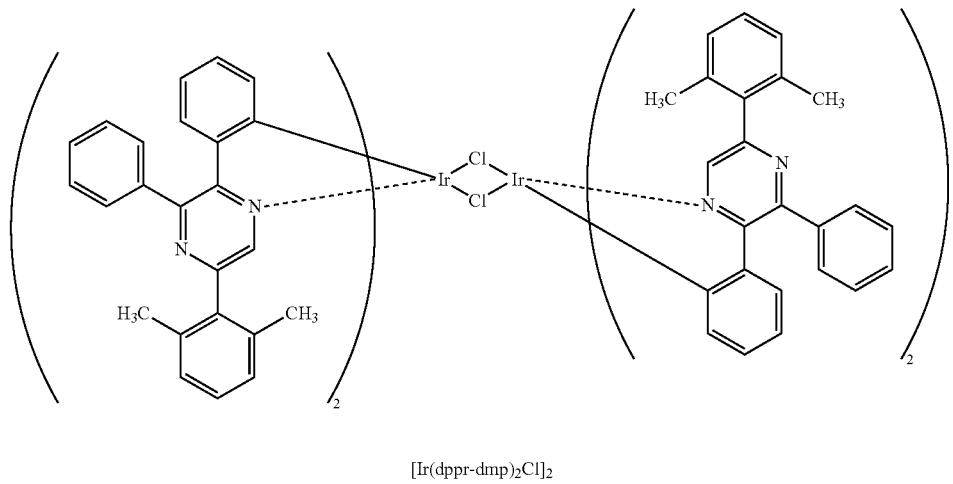

(c-4)

Step 5: Synthesis of [Ir(dppr-dmp)$_2$(divm)]

Then, 0.46 g (0.26 mmol) of [Ir(dppr-dmp)$_2$Cl]$_2$ obtained in Step 4, 0.14 g (0.78 mmol) of 2,8-dimethyl-4,6-nonanedione (abbreviation: Hdivm), 0.28 g (2.6 mmol) of sodium carbonate, and 20 mL of 2-ethoxyethanol were put into a round-bottom flask equipped with a reflux pipe, and the air in the flask was replaced with argon. After that, irradiation with microwaves (2.45 GHz, 120 W) was performed for 1 hour. The solvent was distilled off, and the resulting residue was suction-filtered and washed with methanol.

The obtained solid was dissolved in dichloromethane, and filtered through a filter aid in which Celite, alumina, and Celite were stacked in this order. The solvent in the filtrate was distilled off, recrystallization was performed using a mixed solvent of dichloromethane and methanol, and drying was performed by heating at 200° C.; thus, 0.20 g of the organometallic complex [Ir(dppr-dmp)$_2$(divm)] was obtained as a dark red powder in a yield of 37%.

The synthesis scheme of Step 5 is shown in (c-5) below.

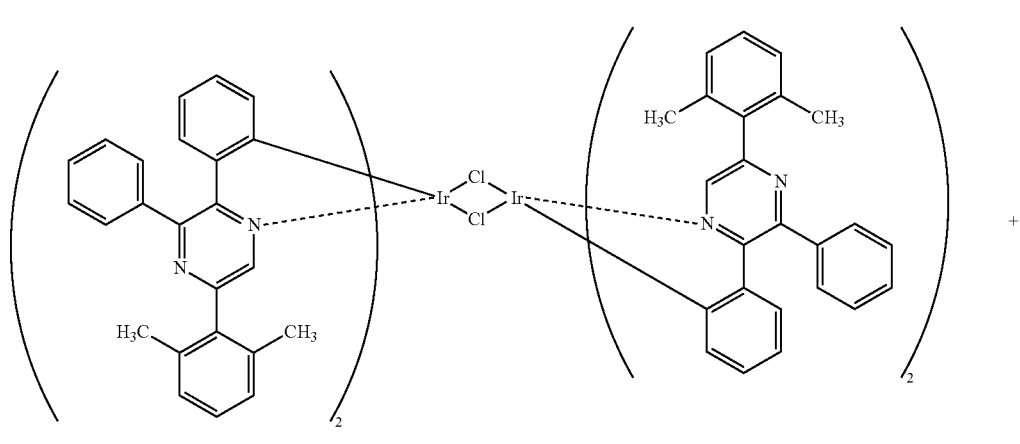

(c-5)

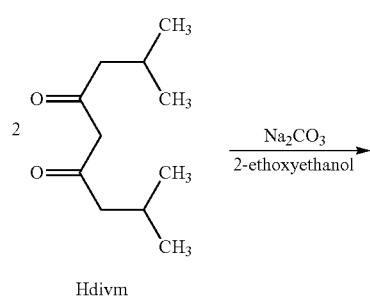

Hdivm

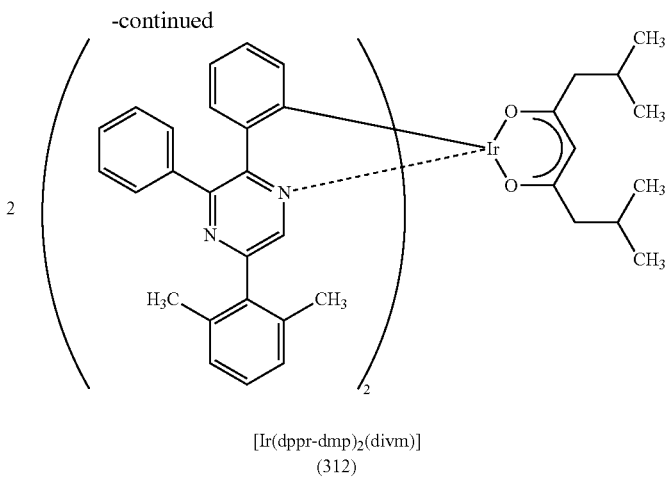

[Ir(dppr-dmp)₂(divm)]
(312)

Figure 13:
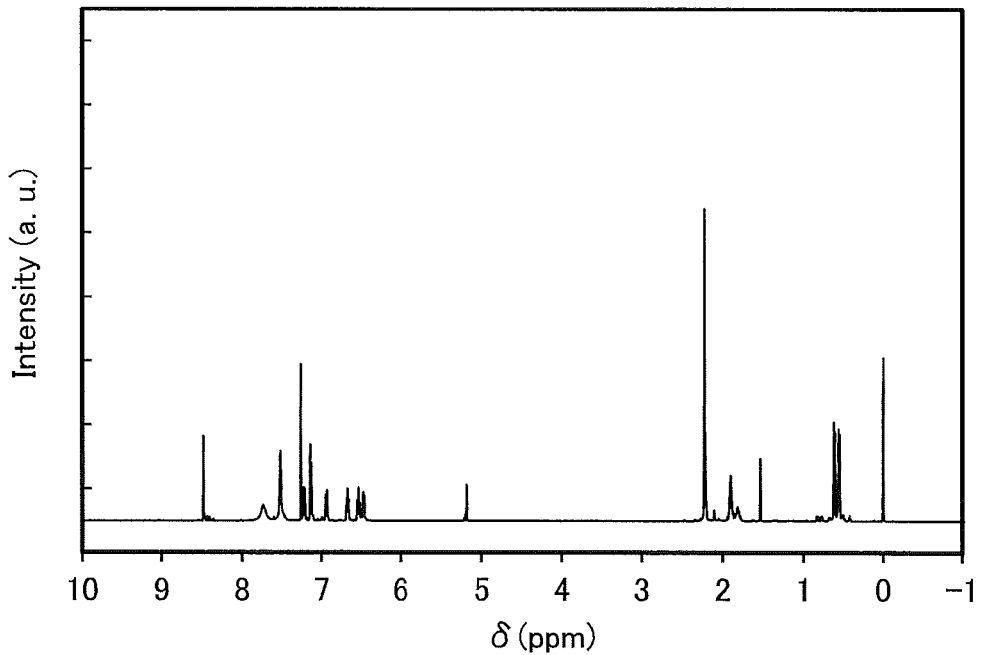
FIG. 13 is a $^1$H-NMR chart of an organometallic complex represented by Structural Formula (312).

Results of analysis of the dark red powder obtained in Step 5 by ¹H-NMR are shown below. A ¹H-NMR chart is shown in FIG. 13. These results show that [Ir(dppr-dmp)₂(divm)] (Structural Formula (312)), which was an organometallic complex of one embodiment of the present invention, was synthesized in Step 5.

¹H NMR (CDCl₃, 500 MHz): δ (ppm)=0.60 (dd, 12H), 1.79-1.84 (m, 2H), 1.92 (s, 4H), 2.22 (s, 12H), 5.19 (s, 1H), 6.47 (d, 2H), 6.53 (dt, 2H), 6.67 (t, 2H), 6.94 (d, 2H), 7.13 (d, 4H), 7.21 (d, 2H), 7.51 (s, 6H), 7.73 (s, 4H), 8.48 (s, 2H).

Next, an ultraviolet-visible absorption spectrum (hereinafter, simply referred to as an "absorption spectrum") of a dichloromethane solution of [Ir(dppr-dmp)₂(divm)] and an emission spectrum thereof were measured. The measurement of the absorption spectrum was conducted on the dichloromethane solution (0.067 mmol/L) in a quartz cell at room temperature with an ultraviolet-visible light spectrophotometer (V550 type manufactured by JASCO Corporation). The measurement of the emission spectrum was conducted on the degassed dichloromethane solution (0.067 mmol/L) in a quartz cell at room temperature with a fluorescence spectrophotometer (FS920 manufactured by Hamamatsu Photonics K.K.).

Figure 14:
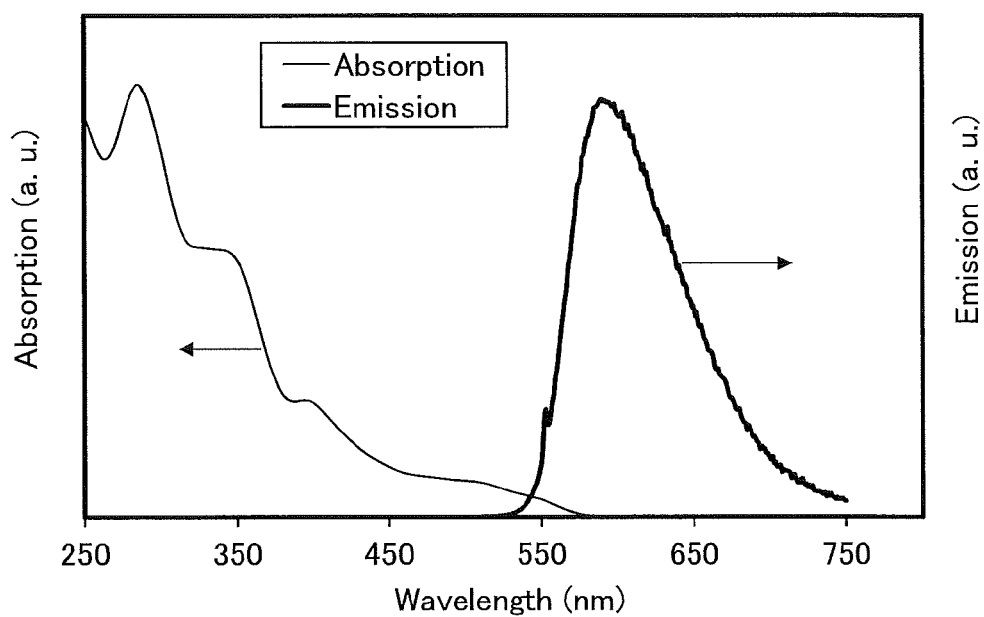
FIG. 14 shows an ultraviolet-visible absorption spectrum and an emission spectrum of an organometallic complex represented by Structural Formula (312).

Analysis results of the obtained absorption and emission spectra are shown in FIG. 14, in which the horizontal axis represents wavelength and the vertical axes represent absorption intensity and emission intensity. FIG. 14 shows two solid lines: the thin solid line represents the absorption spectrum and the thick solid line represents the emission spectrum. Note that the absorption spectrum in FIG. 14 was obtained by subtracting the absorption spectrum of dichloromethane from the absorption spectrum of the dichloromethane solution.

As shown in FIG. 14, the organometallic complex [Ir(dppr-dmp)₂(divm)] has an emission peak at 590 nm, and red-orange light emission was observed from the dichloromethane solution.

Next, [Ir(dppr-dmp)₂(divm)] was subjected to a MS analysis by liquid chromatography mass spectrometry (LC/MS).

In the analysis by LC/MS, liquid chromatography (LC) separation was carried out with ACQUITY UPLC (manufactured by Waters Corporation) and mass spectrometry (MS) analysis was carried out with Xevo G2 TofMS (manufactured by Waters Corporation).

ACQUITY UPLC BEH C8 (2.1×100 mm, 1.7 μm) was used as a column for the LC separation, and the column temperature was 40° C. Acetonitrile was used for Mobile Phase A and a 0.1% aqueous solution of formic acid was used for Mobile Phase B. Further, a sample was prepared in such a manner that [Ir(dppr-dmp)₂(divm)] was dissolved in chloroform at a given concentration and the mixture was diluted with acetonitrile. The injection amount was 5.0 μL.

In the MS analysis, ionization was carried out by an electrospray ionization (ESI) method. At this time, the capillary voltage and the sample cone voltage were set to 3.0 kV and 30 V, respectively, and detection was performed in a positive mode. A component with m/z (mass-to-charge ratio) of 1041.61 which underwent the ionization under the above-described conditions was collided with an argon gas in a collision cell to dissociate into product ions. Energy (collision energy) for the collision with argon was 50 eV. The mass range for the measurement was m/z=100 to 1200. The detection result of the dissociated product ions by time-of-flight (TOF) MS are shown in FIG. 15.

Figure 15:
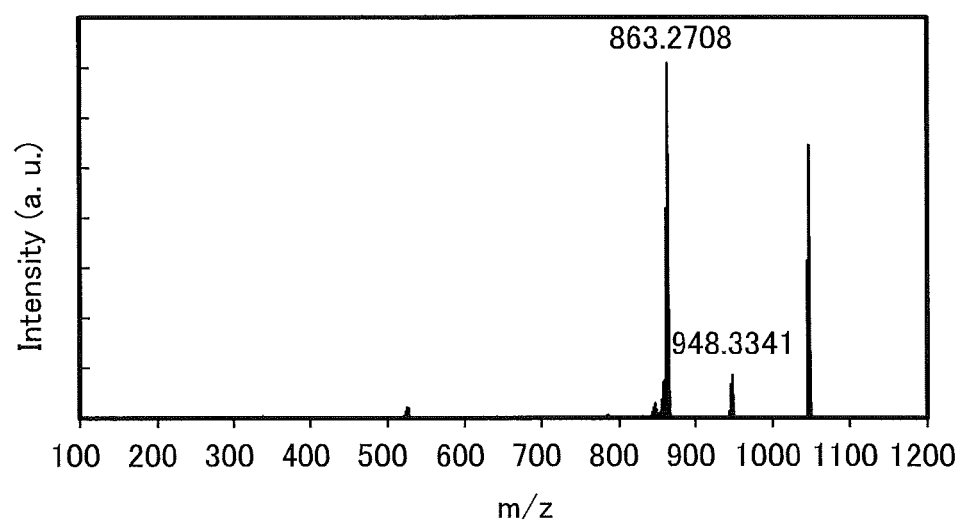
FIG. 15 shows LC/MS measurement results of an organometallic complex represented by Structural Formula (312).

FIG. 15 shows that product ions of [Ir(dppr-dmp)₂(divm)] are mainly detected around m/z=948 and m/z=863. The results in FIG. 15 show characteristics derived from [Ir(dppr-dmp)₂(divm)] and therefore can be regarded as data for identifying [Ir(dppr-dmp)₂(divm)] contained in a mixture.

The product ions around m/z=948 are presumed to be cations in the state where a methyl group is dissociated from [Ir(dppr-dmp)₂(divm)], which means that [Ir(dppr-dmp)₂(divm)] contains an alkyl group. The product ions around m/z=863 are presumed to be cations in the state where Hdivm is dissociated from [Ir(dppr-dmp)₂(divm)], which means that [Ir(dppr-dmp)₂(divm)] contains Hdivm.

Example 4

Synthesis Example 4

Described in this example is a method for synthesizing 5,6-bis(4-methylphenyl)-2-pyrazyl triflate (Structural Formula (105)) which is one embodiment of the present invention. The structure of 5,6-bis(4-methylphenyl)-2-pyrazyl triflate is shown below.

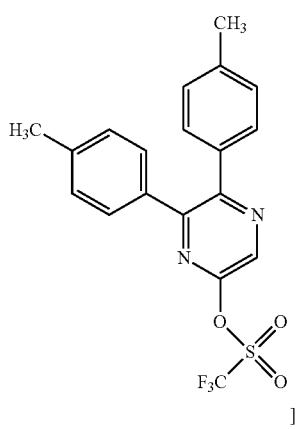

(105)

Step 1: Synthesis of 5,6-bis(4-methylphenyl)pyrazin-2-ol

First, 5.5 g (23 mmol) of 4,4'-dimethylbenzil, 3.1 g (28 mmol) of glycinamide hydrochloride, 2.2 g (55 mmol) of sodium hydroxide, and 120 mL of methanol were put into a three-neck flask equipped with a reflux pipe, the air in the flask was replaced with nitrogen, and the mixture was refluxed for 8.5 hours. Then, stirring was performed until the temperature of the flask was returned to room temperature. After that, 3 mL of 12 M concentrated hydrochloric acid, 2.3 g of potassium bicarbonate, and 58 mL of water were added to this mixture, and filtration was performed.

The obtained solid was dried at 100° C. under reduced pressure and recrystallized with toluene to give 4.8 g of a yellowish white solid in a yield of 75%.

The synthesis scheme of Step 1 is shown in (d-1) below.

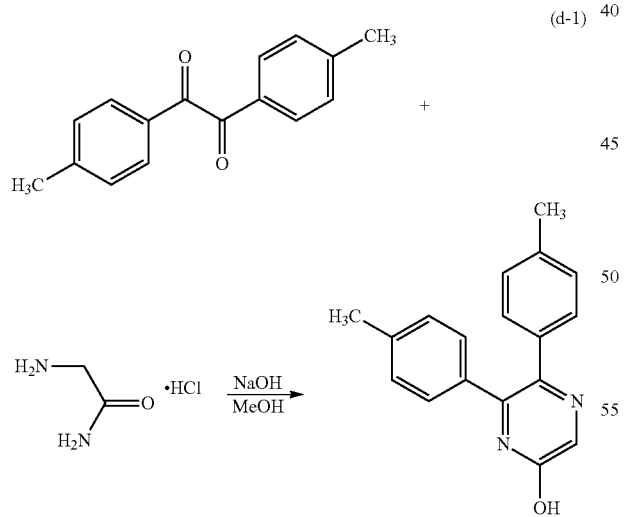

(d-1)

Step 2: Synthesis of 5,6-bis(4-methylphenyl)-2-pyrazyl triflate

Into a three-neck flask were put 4.8 g (17 mmol) of 5,6-bis(4-methylphenyl)pyrazin-2-ol obtained in Step 1, 174 mL of dichloromethane, and 4.9 mL of triethylamine. The air in the flask was replaced with nitrogen, and 4.3 mL of trifluoromethanesulfonic anhydride was added dropwise at 0° C. The mixture was stirred at 0° C. for 1.5 hours, and further stirred at room temperature for 2 hours.

After the reaction, while the flask was cooled with ice, 60 mL of water was added to the mixture, and the organic layer was extracted with dichloromethane. The extract was washed with a saturated aqueous solution of sodium bicarbonate. Magnesium sulfate was added and gravity filtration was performed. The solvent in the filtrate was distilled off, and the resulting residue was purified by silica gel column chromatography using hexane and ethyl acetate in a 1:5 ratio as a developing solvent. Thus, 6.27 g of a yellow solid, which was an objective substance, was obtained in a yield of 88%.

The synthesis scheme of Step 2 is shown in (d-2) below.

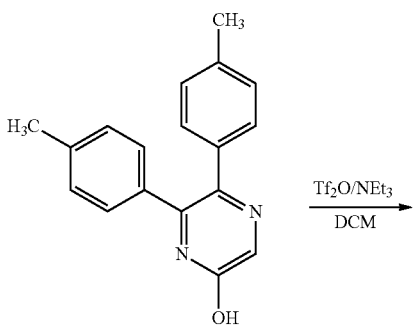

(d-2)

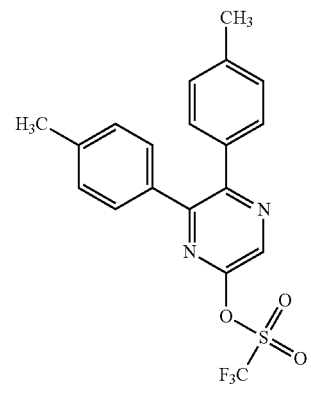

(105)

Figure 16:
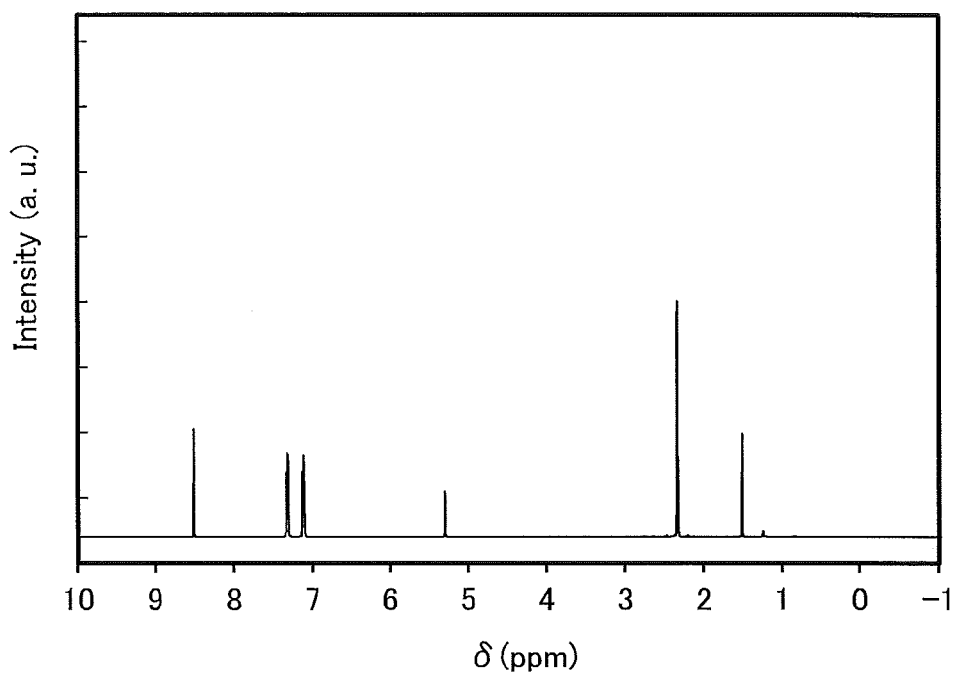
FIG. 16 is a $^1$H-NMR chart of 5,6-bis(4-methylphenyl)-2-pyrazyl triflate represented by Structural Formula (105).

Results of analysis of the yellow solid obtained in Step 2 by $^1$H-NMR are shown below. A $^1$H-NMR chart is shown in FIG. 16. These results show that 5,6-bis(4-methylphenyl)-2-pyrazyl triflate, which was one embodiment of the present invention, was synthesized in Step 2.

$^1$H NMR (CD$_2$Cl$_2$, 500 MHz): δ (ppm)=2.34 (ds, 6H), 7.11-7.14 (t, 4H), 7.31-7.34 (t, 4H), 8.51 (s, 1H).

Example 5

Synthesis Example 5

Described in this example is a synthetic method according to an embodiment of the invention, leading to an organometallic complex, bis{4,6-dimethyl-2-[5-(2,6-dimethylphenyl)-3-(3,5-dimethylphenyl)-2-pyrazinyl-κN]phenyl-κC}(2,4-pentanedionato-κ$^2$O,O')iridium(III) (abbreviation: [Ir(dmdppr-dmp)$_2$(acac)]), represented by Structural Formula (301). The structure of [Ir(dmdppr-dmp)$_2$(acac)] is shown below.

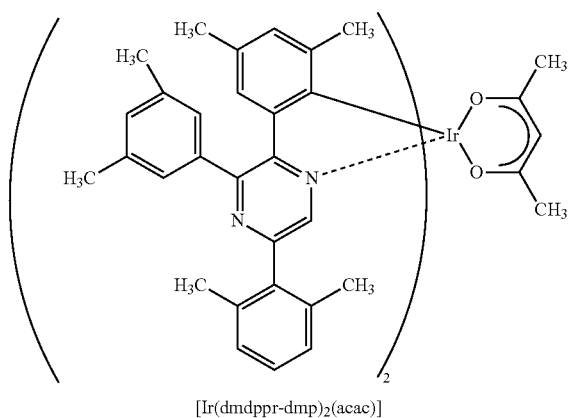

[Ir(dmdppr-dmp)₂(acac)]

Step: Synthesis of Ir(dmdppr-dmp)₂(acac)

Into a round-bottom flask were put 8.77 g (4.3 mmol) of [Ir(dmdppr-dmp)₂Cl]₂ obtained in Step 4 in Synthesis Example 1 of Example 1 above, 1.30 g (13.0 mmol) of 2,4-pentanedione (abbreviation: Hacac), 4.60 g (43 mmol) of sodium carbonate, and 44 mL of 2-ethoxyethanol, and the mixture was bubbled with argon for approximately 15 minutes to replace the air in the flask with argon. After that, irradiation with microwaves (2.45 GHz, 400 W) was performed for 1 hour. The obtained mixture was cooled down to room temperature, and the precipitated solid was obtained by filtration. The obtained solid was washed with water and ethanol to give a red solid. This solid was dried by heating at 100° C. under reduced pressure.

The obtained solid was dissolved in dichloromethane, and filtered through a filter aid in which Celite, alumina, and Celite were stacked in this order. The solvent in the filtrate was distilled off recrystallization was performed using dichloromethane and ethanol, the resulting solid was dried by heating at 100° C. under reduced pressure, so that 7.49 g of the organometallic complex [Ir(dmdppr-dmp)₂(acac)] was obtained as a red powdered solid in a yield of 80%.

By a train sublimation method, 3.0 g of the obtained red powdered solid, which was the objective substance, was purified. The sublimation purification was carried out at 300° C. under a pressure of 3.0 Pa with a flow rate of argon at 13 mL/min. Thus, 2.4 g of the organometallic complex [Ir(dmdppr-dmp)₂(acac)] was obtained as a red crystalline solid in a yield of 80%.

The synthesis scheme of the above step is shown in (e) below.

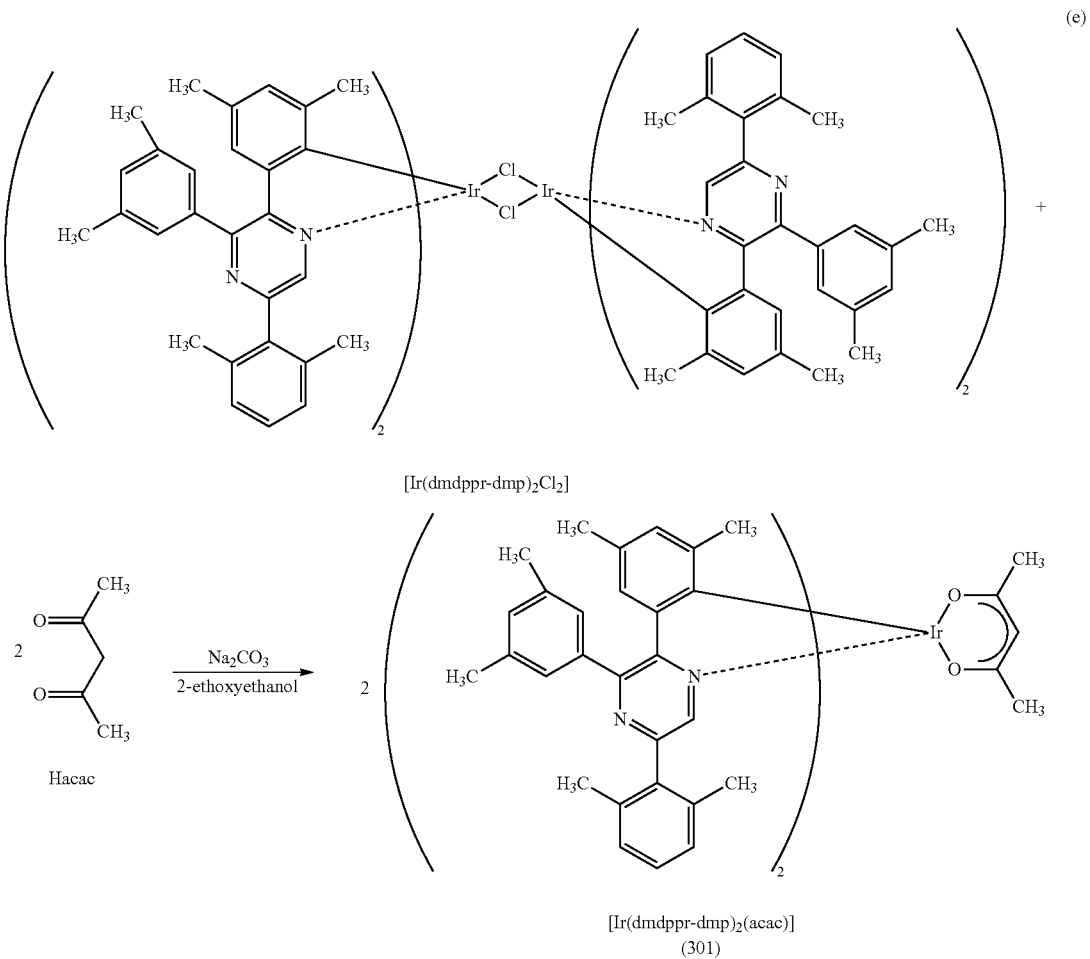

Figure 17:
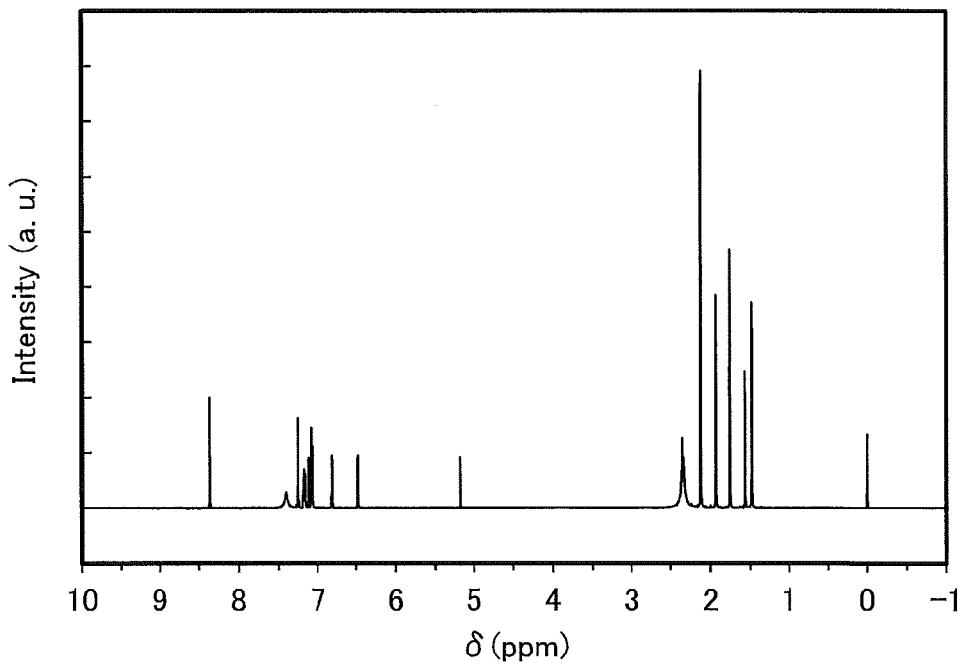
FIG. 17 is a $^1$H-NMR chart of an organometallic complex represented by Structural Formula (301).

Results of analysis of the red solid obtained in the above step by $^1$H-NMR are shown below. A $^1$H-NMR chart is shown in FIG. 17. These results show that an organometallic complex [Ir(dmdppr-dmp)$_2$(acac)](Structural Formula (301)) was synthesized in the above step.

$^1$H NMR (CDCl$_3$, 500 MHz): δ (ppm)=1.48 (s, 6H), 1.75 (s, 6H), 1.94 (s, 6H), 2.12 (s, 12H), 2.26-2.42 (brs, 12H), 5.18 (s, 1H), 6.48 (s, 2H), 6.81 (s, 2H), 7.08 (d, 4H, J=8.0 Hz), 7.12 (s, 2H), 7.18 (t, 2H, J=8.0 Hz), 7.30-7.50 (brs, 4H), 8.37 (s, 2H).

Example 6

In this Example, as a comparison with an embodiment of the present invention, a conventional synthesis method of [Ir(dmdppr-dmp)$_2$(acac)] is described. Specifically, a synthesis via a halogen-containing intermediate is described. The synthesis scheme is shown in (f) below.

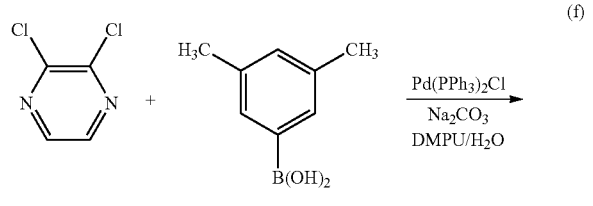

(f)

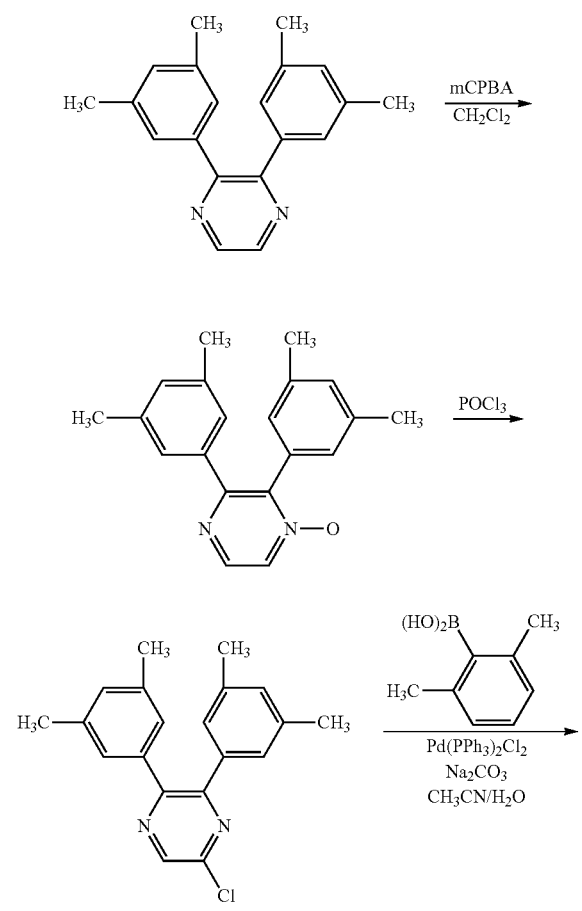

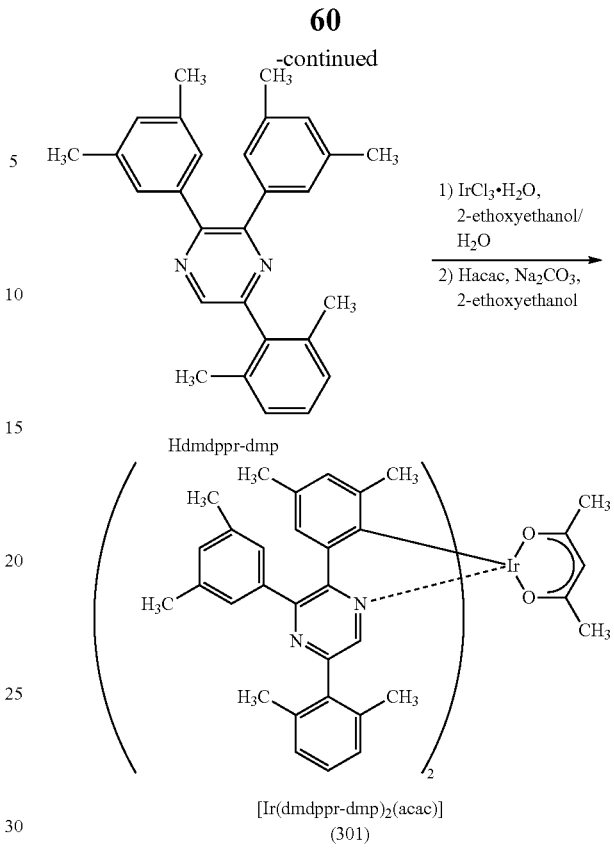

First, a mixture of 5.00 g of 2,3-dichloropyrazine, 10.23 g of 3,5-dimethylphenylboronic acid, 7.19 g of sodium carbonate, 0.29 g of bis(triphenylphosphine)palladium(II) dichloride (PdCl$_2$(PPh$_3$)$_2$), 20 mL of water, and 20 mL of acetonitrile was heated for 60 minutes under argon atmosphere while irradiated with microwaves (2.45 GHz, 100 W). Furthermore, 2.55 g of 3,5-dimethylphenylboronic acid, 1.80 g of sodium carbonate, 0.070 g of PdCl$_2$(PPh$_3$)$_2$, 5 mL of water, and 5 mL of acetonitrile were added, and irradiation with microwaves (2.45 GHz, 100 W) was performed again for 60 minutes so that heating was performed. The mixture was added with water, subjected to extraction with dichloromethane, and purified by column chromatography (developing solvent: hexane:ethyl acetate=5:1 (v/v) and then dichloromethane:ethyl acetate=10:1 (v/v)) to give 2,3-bis(3,5-dimethylphenyl)pyrazine (Hdmdppr) as white powder in 44% yield.

Next, 7.8 g of 3-chloroperoxybenzoic acid (mCPBA) was added to a dichloromethane (90 mL) solution of 6.6 g of Hdmdppr, stirring was conducted at room temperature under nitrogen atmosphere for 24 hours, and the reaction solution was poured into water and subjected to extraction with dichloromethane. The extract solution was washed with a saturated aqueous solution of sodium bicarbonate, dried with magnesium sulfate, filtered, and concentrated to give 2,3-bis(3,5-dimethylphenyl)pyrazin-1-oxide as yellow powder in 100% yield.

Then, to 7.0 g of 2,3-bis(3,5-dimethylphenyl)pyrazine-1-oxide was added phosphoryl chloride, and stirring was performed at 100° C. for 1 hour. The reaction solution was poured into water and extracted with chloroform. The obtained organic layer was washed with a saturated aqueous solution of sodium bicarbonate, water, and then brine, dried with magnesium sulfate, filtered, and concentrated to give 5-chloro-2,3-bis(3,5-dimethylphenyl)pyrazine as gray powder in 90% yield.

Next, a mixture of 1.21 g of 5-chloro-2,3-bis(3,5-dimethylphenyl)pyrazine, 1.10 g of 2,6-dimethylphenylboronic acid, 0.78 g of sodium carbonate, 15 mg of $PdCl_2(PPh_3)_2$, 14 mL of water, and 14 mL of acetonitrile was degassed by bubbling argon for 15 minutes and irradiated with microwaves (2.45 GHz, 100 W) for 3 hours. To the mixture were further added 0.55 g of 2,6-dimethylphenylboronic acid, 0.39 g of sodium carbonate, and 7 mg of $PdCl_2(PPh_3)_2$, and the mixture was degassed by bubbling argon for 15 minutes and heated again by irradiating with microwaves for 6 hours. The mixture was suction-filtered, and the resulting solid was washed with ethanol. The obtained solid was dissolved in dichloromethane, which was followed by filtration through Celite, alumina, and Celite in this order. The filtrate was concentrated to give 5-(2,6-dimethylphenyl)-2,3-bis(3,5-dimethylphenyl)pyrazine as white powder in 89% yield. Explanation of the following reactions is omitted because they are the same as those in Example 5.

Example 7

In this Example, the purity of [Ir(dmdppr-dmp)$_2$(acac)] obtained by the synthesis method of an embodiment of the present invention and that obtained by the conventional synthesis method were estimated by means of the LC/MS analysis. The former was obtained in Example 5, while the latter was obtained in Example 6. The LC/MS analysis was carried out in the same way as that of Example 3.

The purity of the organoiridium complex obtained in Example 5 was calculated to be equal to or higher than 99.9% from the peak area of the LC chromatogram. In contrast, the purity of the organoiridium complex obtained in Example 6 was 99.4%, and 4 chromatogram peaks were observed as impurities. The area ratio of these impurity peaks was approximately 1:1:2:2, and the MS analysis of the peaks gave the m/z of 1107, 1105, 1109, and 1109, respectively. The difference in molecular weight from [Ir(dmdppr-dmp)$_2$(acac)] suggests that these peaks result from chlorine adducts of [Ir(dmdppr-dmp)$_2$(acac)]. Thus, it is concluded that the organoiridium complex obtained by the conventional synthesis method using a halogen-containing intermediate includes halogen adducts as impurities. The attempts of the inventors failed to completely remove the impurities even though the intermediates were purified.

The aforementioned results lead to a conclusion that the synthesis method of an embodiment according to the present invention enables the facile formation of an organometallic complex such as an organoiridium complex in high purity.

Example 8

This Example shows the fabrication and characteristics of a light-emitting element (hereinafter, referred to as Element 1) including the organoiridium complex obtained by applying the synthesis method of an embodiment of the present invention. As a comparative example, the fabrication and characteristics of a comparative light-emitting element (hereinafter, referred to as Reference Element 1) including the organoiridium complex obtained via the halogen-containing intermediate are also demonstrated. The former organoiridium complex was obtained in Example 5, while the latter one was obtained in Example 6. The structure of these elements is the same as that illustrated in FIG. 1. The structures and abbreviations of the compounds used in the element fabrication are shown below.

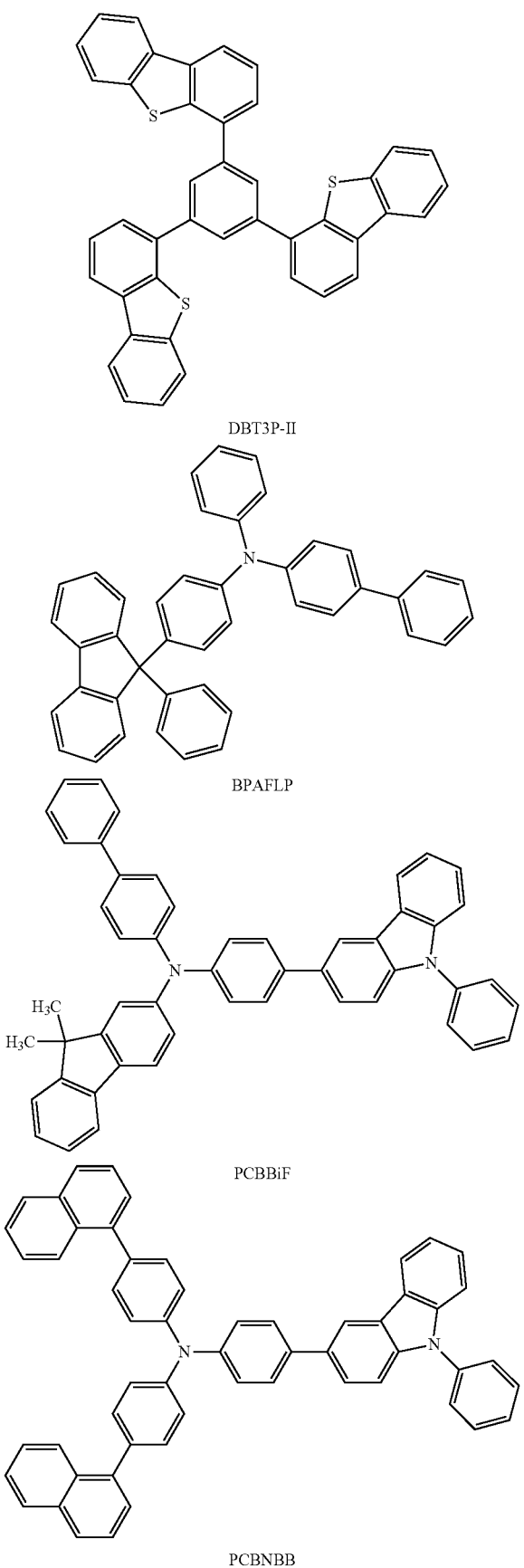

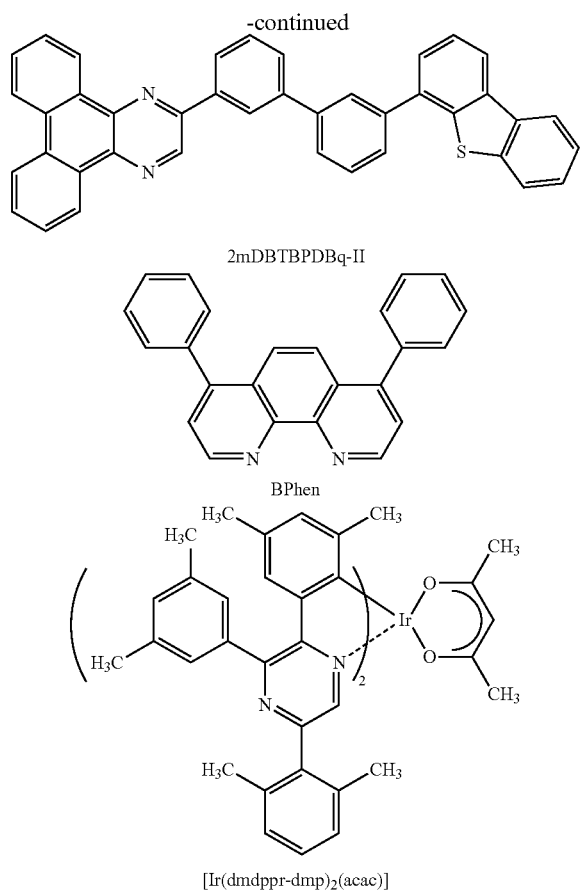

2mDBTBPDBq-II

BPhen

[Ir(dmdppr-dmp)₂(acac)]

<<Fabrication of Element 1>>

Indium tin oxide including silicon oxide (ITSO, thickness: 110 nm, area: 2 mm×2 mm) formed over a glass substrate was employed as the first electrode 101, over which 1,3,5-tri (dibenzothiophen-4-yl)benzene (DBT3P-II) and molybdenum oxide were co-evaporatively deposited to a thickness of 20 nm to form the hole-injection layer 111 where the weight ratio of DBT3P-II:MoO₃ was 2:1.

The hole-transport layer 112 with a thickness of 20 nm was formed over the hole-injection layer 111 by evaporating 4-phenyl-4'-(9-phenylfluoren-9-yl)triphenylamine (BPAFLP).

Over the hole-transport layer 112 was formed the light-emitting layer 113 by co-evaporating 2-[3'-(dibenzothiophen-4-yl)biphenyl-3-yl]dibenzo[f,h]quinoxaline (2mDBTBPDBq-II), N-(1,1'-biphenyl-4-yl)-9,9-dimethyl-N-[4-(9-phenyl-9H-carbazol-3-yl)phenyl]-9H-fluor en-2-amine (PCBBiF), and [Ir(dmdppr-dmp)₂(acac)] to a thickness of 20 nm where the weight ratio of 2mDBTBPDBq-II: PCBBiF:[Ir(dmdppr-dmp)₂(acac)] was 0.8:0.2:0.05.

Over the light-emitting layer 113 was formed the electron-transport layer 114 by sequentially evaporating 2mDBTBPDBq-II and bathophenanthroline (Bphen) to a thickness of 20 nm and 10 nm, respectively. Lithium fluoride and aluminum were evaporated to a thickness of 1 nm and 200 nm to respectively form the electron-injection layer 115 and the second electrode 103 over the electron-transport layer 114. Sealing was carried out by fixing an opposing glass substrate over the glass substrate with a sealing material, by which Element 1 was obtained.

<<Fabrication of Reference Element 1>>

Reference Element 1 was fabricated similarly to Element 1 other than the following points: [Ir(dmdppr-dmp)₂(acac)] prepared via the halogen-containing intermediate was employed; 4,4'-di(1-naphthyl)-4"-(9-phenyl-9H-carbazol-3-yl)triphenylamine (PCBNBB) was used instead of PCBBiF; and the thickness of the Bphen layer was 20 nm. The structures of Element 1 and Reference Element 1 are shown in Table 1. Note that the structures of Element 1 and Reference Element 1 are different from each other in the second host material of the light-emitting layer 113 and the thickness of the Bphen layer. However, the inventors have proven that such a small different does not influence the element reliability.

TABLE 1

Structures of Element 1 and Reference Element 1

| | | Element 1 | | Reference Element 1 | |
|---|---|---|---|---|---|
| Layer | Ref. | thickness (nm) | Material [a] | thickness (nm) | Material [a] |
| 2nd electrode | 103 | 200 | Al | 200 | Al |
| EIL [b] | 115 | 1 | LiF | 1 | LiF |
| ETL [c] | 114 | 10 | Bphen | 20 | Bphen |
| | | 20 | 2mDBTBPDBq-II | 20 | 2mDBTBPDBq-II |
| EmL [d] | 113 | 20 | 2mDBTBPDBq-II:PCBBiF:[Ir(dmdppr-dmp)₂(acac)] (0.8:0.2:0.05) | 40 | 2mDBTBPDBq-II:PCBNBB:[Ir(dmdppr-dmp)₂(acac)] (0.8:0.2:0.05) |
| HTL [e] | 112 | 20 | BPAFLP | 20 | BPAFLP |
| HIL [f] | 111 | 20 | DBT3P-II:MoO$_x$ (2:1) | 20 | DBT3P-II:MoO$_x$ (2:1) |
| 1st electrode | 101 | 110 | ITSO | 110 | ITSO |

[a] Parentheses are weight ratios.
[b] Electron-injection layer.
[c] Electron-transport layer.
[d] Light-emitting layer.
[e] Hole-transport layer.
[f] Hole-injection layer.

Figure 18:
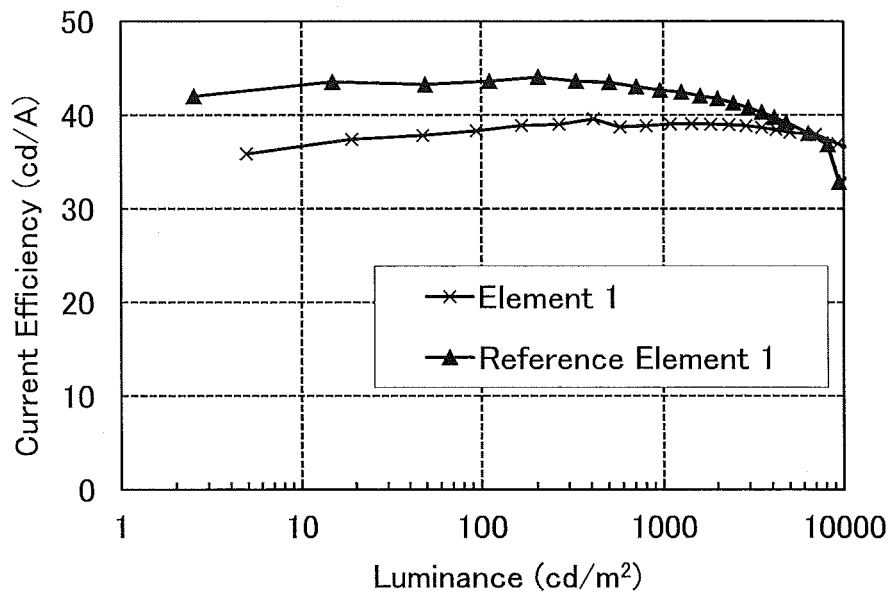
FIG. 18 shows luminance-current efficiency characteristics of Element 1 and Reference Element 1.
Figure 19:
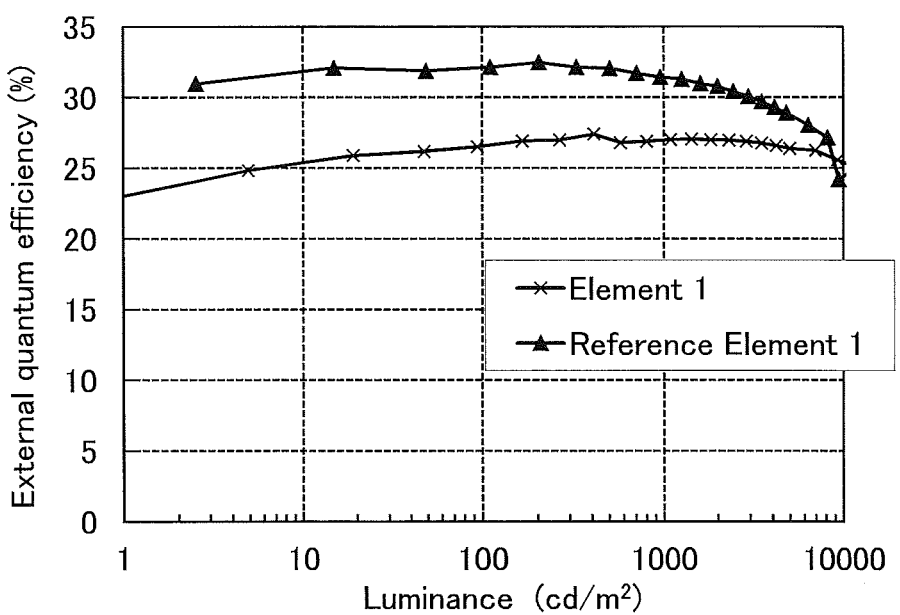
FIG. 19 shows luminance-external quantum efficiency characteristics of Element 1 and Reference Element 1.
Figure 20:
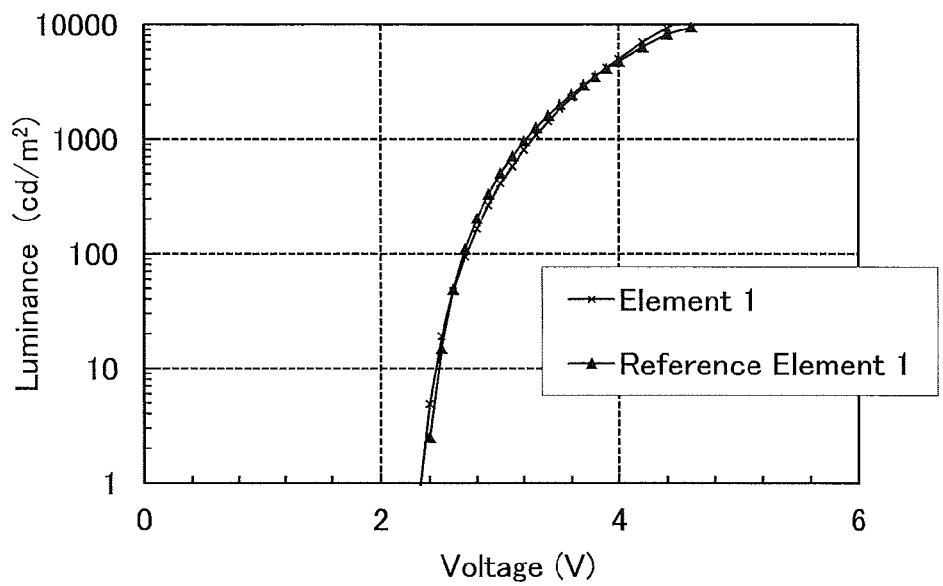
FIG. 20 shows voltage-luminance characteristics of Element 1 and Reference Element 1.
Figure 21:
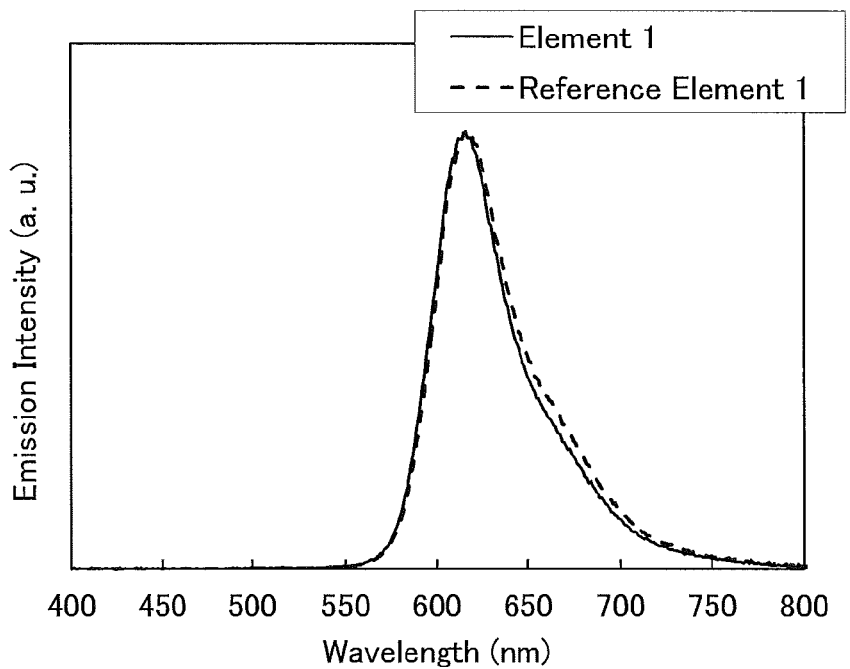
FIG. 21 shows normalized emission spectra of Element 1 and Reference Element 1.

The luminance-current efficiency characteristics, the voltage-luminance characteristics, the luminance-external quantum efficiency characteristics, and the emission spectra of Element 1 and Reference Element 1 are shown in FIGS. 18 to 21, respectively. Almost the same emission spectra were obtained from both elements, which reveals that [Ir(dmdppr-dmp)$_2$(acac)] was confirmed to undergo emission. As shown in FIG. 20, the voltage-luminance characteristics of Element 1 and Reference Element 1 are almost the same. FIGS. 18 and 19 show that Reference Element 1 exhibits higher efficiency than Element 1 to some extent. However, remarkable difference was not observed.

Figure 22:
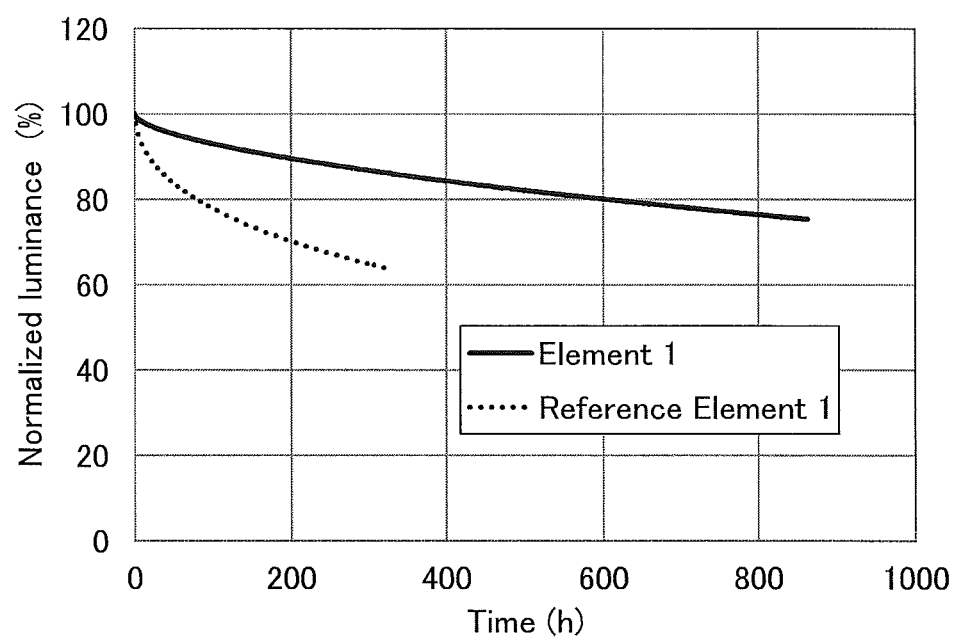
FIG. 22 shows time-normalized luminance curves of Element 1 and Reference Element 1.

In contrast, a large difference in reliability was observed between Element 1 and Reference Element 1. Specifically, as shown in FIG. 22, the constant-current operation of Reference Element 1 with an initial luminance of 5000 cd/m$^2$ at room temperature resulted in a decrease in luminance to less than 70% of the initial value after 300-hour operation. On the other hand, Element 1 maintained more than 70% of the initial luminance even after the operation for 800 hours.

These results lead to a conclusion that the use of the synthesis method of an embodiment according to the present invention allows the formation of an organometallic complex in high purity, which contributes to the fabrication of highly reliable light-emitting elements, light-emitting devices, display devices, and so on.

This application is based on Japanese Patent Application serial no. 2013-245957 filed with Japan Patent Office on Nov. 28, 2013, the entire contents of which are hereby incorporated by reference.

What is claimed is:

1. A synthetic method including:
   coupling a 5,6-diaryl-2-pyrazyl trifluoromethansulfonate with an arylboronic acid derivative to give a 2,5,6-triarylpyrazine.

2. The synthetic method according to claim 1,
   wherein the 5,6-diaryl-2-pyrazyl trifluoromethansulfonate is represented by the following formula:

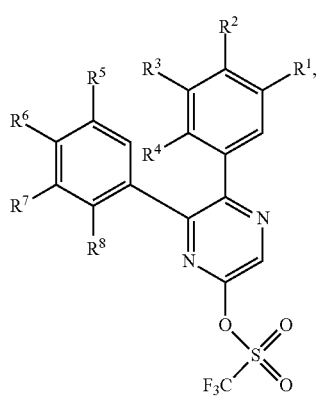

wherein R$^1$ to R$^8$ each independently represent any one of hydrogen, an alkyl group having 1 to 6 carbon atoms, a phenyl group, and a phenyl group having, as a substituent, an alkyl group having 1 to 6 carbon atoms.

3. The synthetic method according to claim 1,
   wherein:
   the arylboronic acid derivative is represented by the following formula:

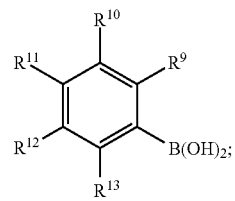

the 2,5,6-triarylpyrazine is represented by the following formula:

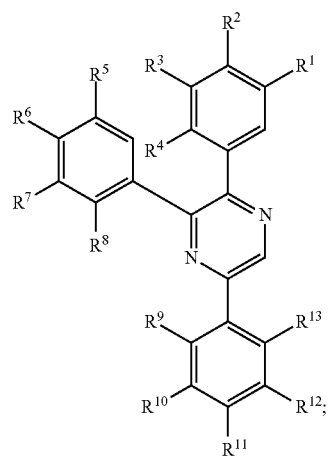

and
   R$^1$ to R$^{13}$ each independently represent any one of hydrogen, an alkyl group having 1 to 6 carbon atoms, a phenyl group, and a phenyl group having, as a substituent, an alkyl group having 1 to 6 carbon atoms.

4. The synthetic method according to claim 1,
   wherein the coupling is conducted in the presence of a palladium catalyst.

5. The synthetic method according to claim 1, further comprising:
   reacting the 2,5,6-triarylpyrazine with a metal compound to give an ortho-metallated complex.

6. The synthetic method according to claim 5,
   wherein the metal compound is iridium chloride.

7. The synthetic method according to claim 3, further comprising:
   reacting the 2,5,6-triarylpyrazine with an iridium compound to give a halogen-bridged complex represented by the following formula:

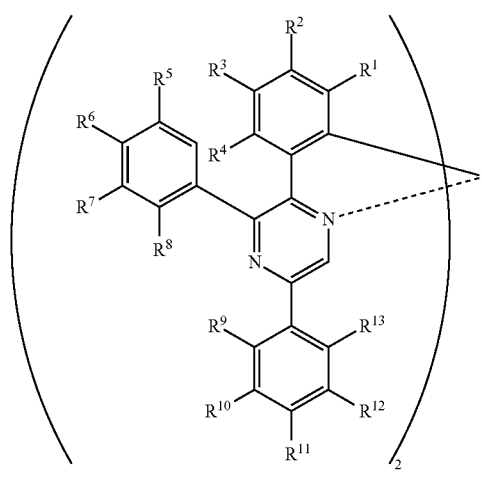

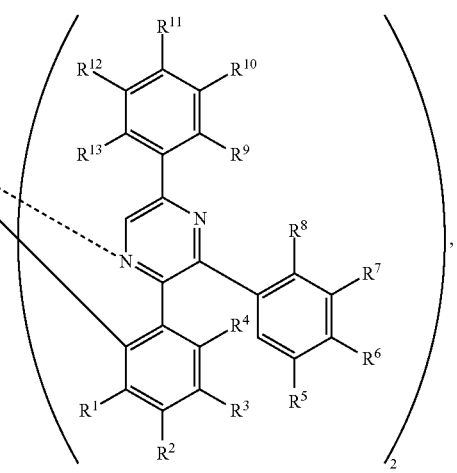

wherein Y is halogen.

8. The synthetic method according to claim 7, further comprising:

reacting the halogen-bridged complex with a ligand to give an ortho-metallated complex.

9. The synthetic method according to claim 8, wherein:

the ortho-metallated complex is represented by the following formula:

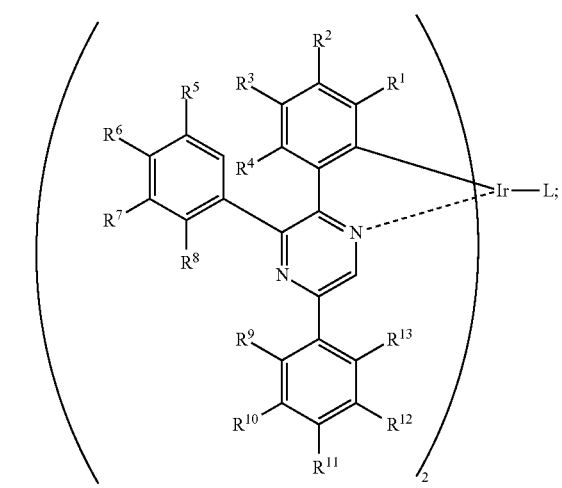

and

L is a monoanionic ligand.

10. A method for manufacturing a light-emitting element, the method comprising:

coupling a 5,6-diaryl-2-pyrazyl trifluoromethansulfonate with an arylboronic acid derivative to give a 2,5,6-triarylpyrazine;

transforming the 2,5,6-triarylpyrazine to an ortho-metallated complex by using a metal compound;

forming a layer including the ortho-metallated complex between a pair of electrodes.

11. The method according to claim 10, wherein the 5,6-diaryl-2-pyrazyl trifluoromethansulfonate is represented by the following formula:

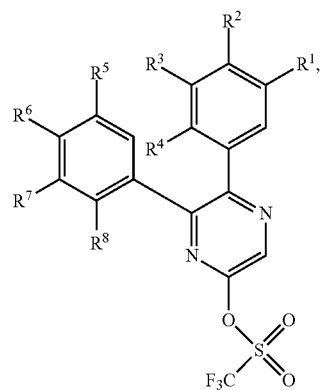

wherein $R^1$ to $R^8$ each independently represent any one of hydrogen, an alkyl group having 1 to 6 carbon atoms, a phenyl group, and a phenyl group having, as a substituent, an alkyl group having 1 to 6 carbon atoms.

12. The method according to claim 10, wherein:

the arylboronic acid derivative is represented by the following formula:

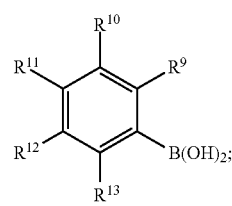

the 2,5,6-triarylpyrazine is represented by the following formula:

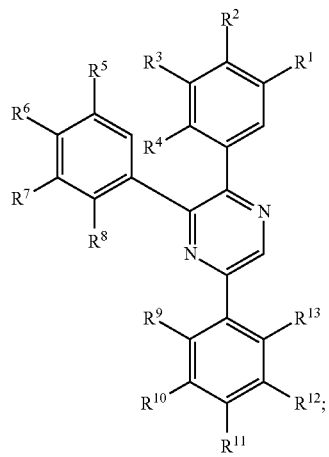

and

R$^1$ to R$^{13}$ each independently represent any one of hydrogen, an alkyl group having 1 to 6 carbon atoms, a phenyl group, and a phenyl group having, as a substituent, an alkyl group having 1 to 6 carbon atoms.

13. The method according to claim 10, wherein the coupling is conducted in the presence of a palladium catalyst.

14. The method according to claim 10, wherein the metal compound is iridium chloride.

15. The method according to claim 12, wherein:
the ortho-metallated complex is represented by the following formula:

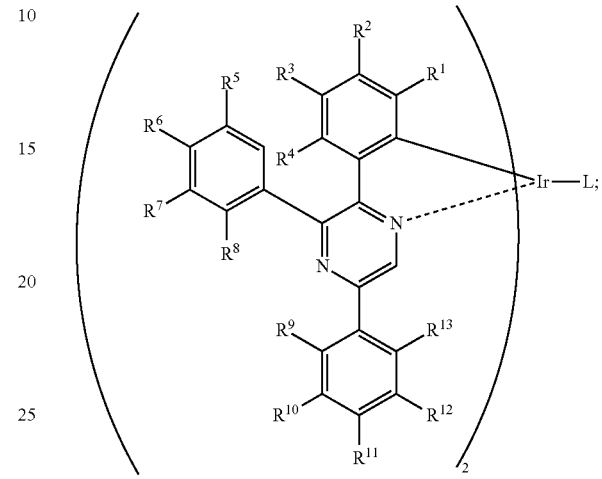

and

L is a monoanionic ligand.

16. The method according to claim 12, wherein:
the transformation of the 2,5,6-triarylpyrazine to the ortho-metallated complex includes a reaction of the 2,5,6-triarylpyrazine with iridium chloride to form a halogen-bridged dinuclear complex represented by the following formula:

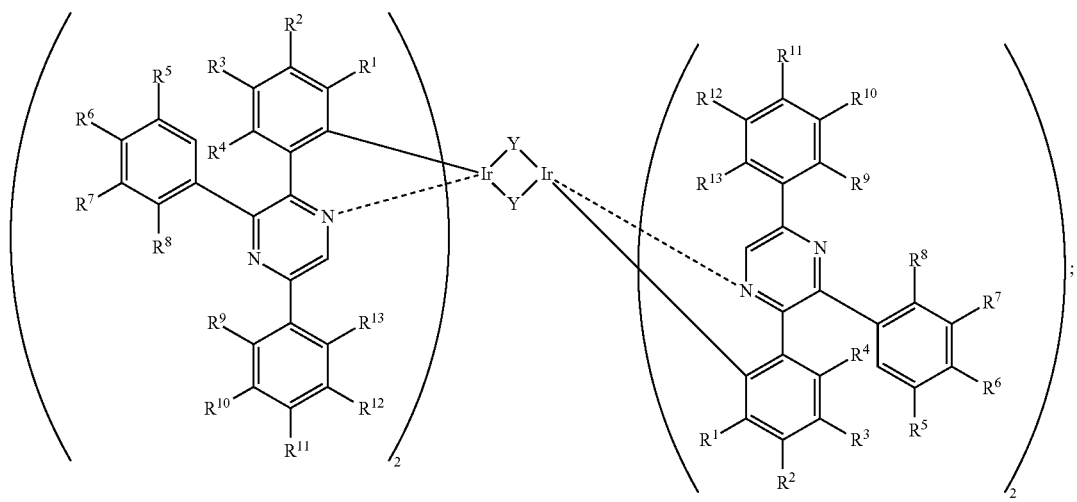

and
Y is halogen.

17. The method according to claim 16, wherein the transformation of the 2,5,6-triarylpyrazine to the ortho-metallated complex includes a reaction of the halogen-bridged dinuclear complex with a ligand.

* * * * *

UNITED STATES PATENT AND TRADEMARK OFFICE
CERTIFICATE OF CORRECTION

| | | |
|---|---|---|
| PATENT NO. | : 9,231,217 B2 | Page 1 of 1 |
| APPLICATION NO. | : 14/551712 | |
| DATED | : January 5, 2016 | |
| INVENTOR(S) | : Hideko Inoue et al. | |

It is certified that error appears in the above-identified patent and that said Letters Patent is hereby corrected as shown below:

In the Specification:

Column 23, Line 40; Change "titanium (Ii)." to --titanium (Ti).--.

Column 25, Line 15; Change "4-yl  idene)" to --4-ylidene--.

Column 25, Line 23; Change "benzo[i]" to --benzo[ij]--.

Column 25, Line 50; Change "terbium(II)" to --terbium(III)--.

Column 25, Line 54 to 55; Change "iridium(II)" to --iridium(III)--.

Column 25, Line 62; Change "Ir(Fdpq)z(acac))," to --Ir(Fdpq)$_2$(acac)),--.

Column 25, Line 65 to 66; Change "[Ir(mppr-iPrh(acac)])," to --[Ir(mppr-iPr)$_2$(acac)],--.

Column 26, Line 8; Change "Eu(TA)$_3$(Phen))." to --Eu(TTA)$_3$(Phen)).--.

Column 31, Line 9; Change "Group II" to --Group III--.

Column 33, Line 11; Change "image; and" to --image, and--.

Column 41, Line 26 to 27; Change "(dd, 121H)," to --(dd, 12H),--.

Column 44, Line 57; Change "iridium(m)" to --iridium(III)--.

Column 47, Line 26; Change "(CDC$_3$," to --(CDCl$_3$,--.

Column 58, Line 13; Change "distilled oft recrystallization" to --distilled off, recrystallization--.

Column 64, Line 13; Change "9F[-fluor en" to --9F[-fluoren--.

Signed and Sealed this
Fifth Day of July, 2016

Michelle K. Lee
*Director of the United States Patent and Trademark Office*